US008592652B2

(12) United States Patent
Frank et al.

(10) Patent No.: US 8,592,652 B2
(45) Date of Patent: Nov. 26, 2013

(54) USE OF SUBTILISIN-LIKE RNR9 POLYNUCLEOTIDE FOR ACHIEVING PATHOGEN RESISTANCE IN PLANTS

(75) Inventors: Markus Frank, Neustadt (DE); Patrick Schweizer, Gatersleben (DE); Dimitar Douchkov, Gatersleben (DE)

(73) Assignee: BASF Plant Science GmbH, Ludwigshafen (DE)

( * ) Notice: Subject to any disclaimer, the term of this patent is extended or adjusted under 35 U.S.C. 154(b) by 972 days.

(21) Appl. No.: 12/523,101

(22) PCT Filed: Jan. 15, 2008

(86) PCT No.: PCT/EP2008/050402
§ 371 (c)(1),
(2), (4) Date: Jul. 14, 2009

(87) PCT Pub. No.: WO2008/087141
PCT Pub. Date: Jul. 24, 2008

(65) Prior Publication Data
US 2010/0170005 A1 Jul. 1, 2010

(30) Foreign Application Priority Data
Jan. 15, 2007 (EP) .................................... 07100564

(51) Int. Cl.
C12N 15/82 (2006.01)
C12N 5/04 (2006.01)
C12N 15/90 (2006.01)

(52) U.S. Cl.
USPC ........... 800/301; 800/279; 800/285; 800/286; 435/468

(58) Field of Classification Search
None
See application file for complete search history.

(56) References Cited

U.S. PATENT DOCUMENTS

| 4,987,071 | A | 1/1991 | Cech et al. |
| 5,116,742 | A | 5/1992 | Cech et al. |
| 7,456,335 | B2 | 11/2008 | Kogel et al. |
| 2003/0017566 | A1* | 1/2003 | Duvick et al. ................ 435/189 |
| 2004/0098769 | A1* | 5/2004 | Mahajan .................... 800/320.1 |
| 2006/0236427 | A1* | 10/2006 | Chiang et al. ................. 800/284 |
| 2008/0047033 | A1 | 2/2008 | Kogel et al. |

FOREIGN PATENT DOCUMENTS

| WO | WO-98/04586 A2 | 2/1998 |
| WO | WO-99/32619 A1 | 7/1999 |
| WO | WO-99/47552 A2 | 9/1999 |
| WO | WO-00/01722 A1 | 1/2000 |
| WO | WO-00/03598 A1 | 1/2000 |
| WO | WO-03/020939 A1 | 3/2003 |
| WO | WO-2004/009820 A1 | 1/2004 |

OTHER PUBLICATIONS

Jordá et al, 1999, J. Bio. Chem., 274:2360-2365.*
Muyanga et al, 2005, S. African J. of Sci., 100:201-204.*
Thomas et al, 2001, Plant J., 25:417-425.*
Ruiz et al, 1998, Plant Cell, 10:937-946.*
Yamagata, H., at al., "Cucumisin, a Serine Protease from Melon Fruits, Shares Structural Homology with Subtilisin and is Generated from a Large Precursor". The Journal of Biological Chemistry, 1994, vol. 269, No. 52, pp. 32725-32731.
Anandalakshmi, R., et al., "A viral suppressor of gene silencing in plants". Proc. Natl. Acad. Sci. USA, 1998, vol. 95, pp. 13079-13084.
Angell, S.M,, et al., "Potato virus X amplicon-mediated silencing of nuclear genes". The Plant Journal, 1999, vol. 20, No. 3, pp. 357-362.
Bolduc, N., et al., "Molecular characterization of two plant B1-1 homologues which suppress Bax-induced apoptosis in human 293 cells". Planta, 2003, vol. 216, pp. 377-386.
Fagard, M., at al., "Systemic silencing signal(s)". Plant Molecular Biology, 2000, vol. 43, pp. 285-293.
Famulok, M., et al., "Aptamers as Tools in Molecular Biology and Immunology". Current topics in microbiology and immunology, 1999, Vol, 243, pp. 123-136.
Franken, E., at al., "Recombinant proteins from transgenic plants". Current Opinion in Biotechnology, 1997, vol. 8, pp. 411-416.
Helene, C., "The anti-gene strategy: control of gene expression by triplex-forming-oligonucleotides". Anti-Cancer Drug Design, 1991, vol. 6, pp. 569-584.
Helene, C., et al., "Control of Gene Expression by Triple Helix-Forming Oligonucleotides". Annals New York Academy of Sciences, 1992, vol. 660, pp. 27-36.
Jorda, L., et al., "A Genomic Cluster Containing Four Differentially Regulated Subtilisin-like Processing Protease Genes is in Tomato Plants". The Journal of Biological Chemistry, 1999, vol. 274, No. 4, pp. 2360-2365.
Maher III, L.J., "DNA Triple-Helix Formation: An Approach to Artificial Gene Repressors?". BioEssays, 1992, vol. 14, No. 12, pp. 807-816.
Meichtry, J., at al., "Characterization of the subtilase gene family in tomato (*Lycopersicon esculentum* Mill.)". Plant Molecular Biology, 1999, vol. 39, pp. 749-760.
Owen, M., at al., "Synthesis of a functional anti-phytochrome single-chain $F_v$ protein in transgenic tobacco". Biotechnology, 1992, vol. 10, pp. 790-794.

(Continued)

*Primary Examiner* — Ashwin Mehta
*Assistant Examiner* — Jason Deveau Rosen
(74) *Attorney, Agent, or Firm* — Novak Druce Connolly Bove + Quigg LLP

(57) ABSTRACT

The invention relates to a method of generating or increasing a pathogen resistance in plants by reducing the expression of at least one subtilisin polypeptide or a functional equivalent thereof. The invention relates to novel nucleic acid sequences coding for a *Hordeum vulgare* subtilisin (HvRNR9) and *Triticum aestivum* subtilisin (TaRNR9) polynucleotide and describes homologous sequences (RNR9) thereof, and to their use in methods for obtaining a pathogen resistance in plants, and to nucleic acid constructs, expression cassettes and vectors which comprise these sequences and which are suitable for mediating a fungal resistance in plants. The invention furthermore relates to transgenic organisms, in particular plants, which are transformed with these expression cassettes or vectors, and to cultures, parts or transgenic propagation material derived therefrom.

16 Claims, 14 Drawing Sheets

(56) References Cited

OTHER PUBLICATIONS

Ratcliff, F., et al., "Tobacco rattle virus as a vector for analysis of gene function by silencing". The Plant Journal, 2001, vol. 25, No. 2, pp. 237-245.

Ribeiro, A., et al., "A Nodule-Specific Gene Encoding a Subtilisin-Like Protease is Expressed in Early Stages of Actinorhizal Nodule Development", The Plant Cell, 1995, vol. 7, pp. 785-794.

Riggs, C.D., et al., "Molecular cloning of an anther specific gene from tomato". Plant Physiology, 1995, vol. 108, p. 117.

Ruiz, M.T., et al., "Initiation and Maintenance of Virus-Induced Gene Silencing", The Plant cell, 1998, vol. 10, pp. 937-946.

Schweizer, P., et al., "Double-stranded RNA interferes with gene function at the single-cell level in cereals". The Plant Journal, 2000, vol. 24, No. 6, pp. 895-903.

Siezen, R.J., et al., "Subtilases: The superfamily of subtilisin-like serine proteases". Protein science, 1997, vol. 6, pp. 501-523.

Whitelam, G.C., et al., "Antibody expression in transgenic plants". Trends in Plant Science, 1996, vol. 1, No. 8, pp. 268-272.

Nelsen, N.S., et al., "Genomic Polymorphism Identifies a Subtilisin-Like Protease Near the *Rhg4* Locus in Soybean", Crop Science, vol. 44, No. 1, (2004), pp. 265-273.

\* cited by examiner

Figure 1

<u>Nucleic acid sequence of subtilisin RNR9 from Triticum aestivum (wheat); TaRNR9</u>

```
TATCGTCGACCCACGCGTCCGCCACCCATCGCTCATTTCCGGCGAGCCACCGCGCGGGGGCCGCCGA
TCTCCGGCGAATCGCGCCGATGCCGCCGCCCGCGATGGCGGCCGAGAAGAGGAGGGCCGCGTACGC
GGCCTTCCTCCCGCTCCTCCTCCTCCTCGCGCTCCGCGCCCTCCTCCCCTCCTCCGACCCCCCGGCCCG
GGGCGGGGAGGAAACCCTAGCCAGCAGCAGGTACGTCGTGCGGTTCCtCGAGTACCGCCCCGCCGAC
GACCACCGGGAGTACCTGGAGGACGGCCTCCCCCGCGAGGCCGGGCCGTGGCGGTGGGTGGAGCGG
CGGAACCCCGCGGCCGCGCACCCGACCGACTTCGCCGTGCTCGAGATCCGCGACGCGCACCGGGACG
CCGTCTCCGAGGCCCTCCGCGCGCTCGCCCGCGTCCGGGACGTGCACCCCGACACCAGCCACTCGCG
GGCCGCCCTGTCCGCAGATCGGGCGCGGGGCAAGCGCTTCACCGCCATGTCGTTCGAGGAGGAGGG
ACGCGGCGGCGACGACGACGCGGTTCCCAGCAATAATGCTAGTTCCTCTTCTGGTGGTCCGAGGCGG
AAGCTTCAAATGCGGAGACCACATGTGACATCTCTATTTGGAGCTGCACAACTATGGGAAAGAGGCT
TCACTGGTAGGAAAGTCAAAATGGCCATTTTTGACACTGGTATTCGGGCAGATCACCCACATTTTCGC
AATATTAAGGAGCGCACAAATTGGACAAATGAAGACACATTAAATGACAACCTTGGACATGGAACA
TTTGTAGCTGGAGTGATTGCTGGTCAAGATCCAGAATGTCCTGGATTTGCACCAAACACTGAGATAT
ATGCATTTCGAGTGTTCACAGATGCTCAGATATCCTACACATCATGGTTCTTGGATGCATTTAATTAT
GCGATGGCAACTGGTATGGATGTATTGAATTTGAGTATTGGTGGACCTGATTACCTGGATCTCCCCTT
TGTGGAAAAGGTCTGGGAGCTCACAGCAAACAACATTATTATGGTATCAGCTATTGGAAATGATGGT
CCTCTCTATGGCACATTAAATAACCCAGCGGACCAAAGCGACGTCATTGGCGTTGGTGGTATTGATT
ACAATAACCACATAGCTTCATTTTCCTCTAGAGGCATGACTACCTGGGAACTTCCCCATGGATATGGC
CGTGTAAAACCTGATGTTGTCGCATACAGTCGTGATATAATGGGTTCTAAGACCAGCACAGGCTGCA
AGACTCTTTCAGGTACAAGTGTTGCAAGCCCGGTGGTTGCTGGAGCAGTATGCTTGCTTGTTAGTGTT
ATACCAGAAGACAAGCGGAAATCCATCCTTAATCCTGCTAGTATGAAACAGGCCCTTGTTGAGGGTG
CTTCTAAGCTTGTGGGGCCGAATATATATGAGCAGGGTGCAGGCAAGCCTGATCTATGGCAATCATA
TGAAATATTGAAAAATTACCAACCACGAGCAAGTGTATTTCCTAACATGCTTGACTTCACCGACTGTC
CCTACTTCTGGCCTTTTTGTCGGCAACCTTTGTATGCTGGAGCCATGCCAGTAGTATTCAATGCTACA
ATTCTTAATGGGATGGGGGTGATTGGTTATGTTAAGGATCCACCTGTATGGCAGCCATCTGAAGATGT
GGGCAATCTTCTCACTGTTCACTTCACCTACTCGGACACCATCTGGCCTTGGACAGGGTACCTTGCCC
TGCACATGCAAGTTAAAGACGAAGgTTCTCAGTTTTCAGGCATAATTAGTGgCAATGTTACcCTGTCG
ATTTACAGCCCAGCTACTGAGGGGGAAAGCAGCCCACGGAGTAGTACGTGTGTTCTTTACCTGAAGG
TCAGGGTGGTTCAAACACCTGTTAGGTCAAGAAGAATACTGTGGGACCAATTTCATAACATCAAGTA
CCCATCTGGATATGTTCCGAGGGATTCACTTAATGTGAATAATGATATCCTTGATTGGCATGGTGACC
ACTTACACACAAATTTTCACATACTGTTCAACATGCTGAGAGATGCAGGATACTATGTTGAGACCCTT
GGGTCACCACTTACCTGCTTTGACGCTAGCAATTATGGTACACTGCTCATGGTTGATCTTGAGGACGA
GTACTTCAGTGAAGAGATTCAGAAACTCAGGGATGATGTTGTACACAAGGGGCTCGGCCTTGCTGTT
TTTGCTGAATGGTATCATGTTGATACCATGGTGAAGATGACATTCTTTGATGAAAATACCCGCAGTTG
GTGGAGTCCGCTTACTGGTGGTGCAAATATTCCTGCGCTTAATGAACTTTTGGCCCCATTTGGCATTG
CTTTTGGGGACAAAATATTGAGTGGTGATTTCTCAATCAATGGTGAGCAGTCCCACTATGCTTCTGGG
ACTGATATAGTGCAATTCCCAGCAGGAGGTTTTTTGCATGGCTTCGAACTCCAGGAAGACCCCAAAA
CTGCACAGAATAGCTCAACTCCAGATACACAGAACTCCCAGTCCCAGGAGAAGAGCAAGGCGAAGG
GCGAATTGCAGTATATGGGGATTCAAATTGTCTTGACAGTAGTCACATGGTAACAAACTGTTATTGG
CTTTTGAGAAAAATTGTGGAGTTTGCTGGCAATGGACTCAGAGATCCTGTCCTTTTCTCAGAAGCAAC
TCGGTTAAAATTTCCAGTTTTTGAGAACATCCAGAAACCCTTGCGTAGACCCGATGTAAATTTTTCAA
TGTTTTCATCTGTCATTGGCAAGGAATTGATATGTCACCAGGATTCCCGATTTGAAGTTTGGGGTACG
AAAGGTTATGGTATCCAACTAACAGGCACAACAAGAAAAGCTGCCAGAATACCAAAAGAATGAAGTT
TCTAGTAGTCCCAATCGATTAATaAAATCTTCTTACAAGAGACAAGATGAAGCTGGCTTGCAAAAATC
CATTTTAGCACCGAGTGCTAATAAATTTGATGATAATAGAGATTATTTTGGCTTTATCAGCCATGAAG
AGGTCGCAAGCCAATGGATGGTACCTGCTTGCTTTGCTGTCACTACTTGCATTCTGGTGTACCTCAGT
TGCAGAGCGCAACAAAGGCGCCGTCGACCAAGGAAAGGGTCCGCAACCGGTCGTCTGTCAAGTTCG
GTATAACATGGAAACTTGTGTGGGGCCAAAGAAGGTTTTGGCTCCAGCGTGTCTGGCCATCTGCCAT
GGTACATGATATAACTGAAGTTACATCGGTCCACTGACTGGACACATAAAAAAGCTCGCAATGGATGTC
AATCGAGGTCCAAGTCGTGGTGGCTCATGTTTAGAATGTGCGAAGAGAGCCCAGTCAAACACCTCTG
CAACTGCGTGGCTATGTTCCAACATTTTGTGTCATGCGCCATCGCCATCGCCATCGCCATCCAGTTGT
AACAAACTCTGTGTCTATAATAATAATAGACTGCTTTGGGACATAATAGGCGAGAGCTAATTCAGTA
GGAAGAGGCTAGGGTTGACGTCTTTCTTTCTTTCTTTCTTTTTCATCTCTTCTTCTTCTTCCTTTTTCTT
TTCTTTTGTGAAAGGATGACTTGCTTCTTGTAGGTCAGTAAGCCATTCTAGTTTTCAGGGTGGCTATG
CTTCAGCTTGTAAGTACTGGACGAGCTCATCTGAAAACAGAGGAAGGCCTCAGCAGTTTATGAGGGT
TTTTTTCTGGAGTAAAAAAAAAAAAAAAA
```

Full length cDNA sequence of the wheat ortholog of RNR9 (Subtilase; 3737 bp): The transcription start is marked by the underlined start-codon (ATG, position 87-89)

Figure 2

Protein sequence of subtilisin RNR9 from Triticum aestivum (wheat); TaRNR9; 1038 aa MPPPAMAAEKRRAAYAAFLPLLLLLALRALLPSSDPPARGGEETLASSRYVVRFLEYRPADDHREYLEDG
LPREAGPWRWVERRNPAAAHPTDFAVLEIRDAHRDAVSEALRALARVRDVHPDTSHSRAALSADRARG
KRFTAMSFEEEGRGGDDDAVPSNNASSSSGGPRRKLQMRRPHVTSLFGAAQLWERGFTGRKVKMAIFDT
GIRADHPHFRNIKERTNWTNEDTLNDNLGHGTFVAGVIAGQDPECPGFAPNTEIYAFRVFTDAQISYTSWF
LDAFNYAMATGMDVLNLSIGGPDYLDLPFVEKVWELTANNIIMVSAIGNDGPLYGTLNNPADQSDVIGV
GGIDYNNHIASFSSRGMTTWELPHGYGRVKPDVVAYSRDIMGSKTSTGCKTLSGTSVASPVVAGAVCLL
VSVIPEDKRKSILNPASMKQALVEGASKLVGPNIYEQGAGKPDLWQSYEILKNYQPRASVFPNMLDFTDC
PYFWPFCRQPLYAGAMPVVFNATILNGMGVIGYVKDPPVWQPSEDVGNLLTVHFTYSDTIWPWTGYLAL
HMQVKDEGSQFSGIISGNVTLSIYSPATEGESSPRSSTCVLYLKVRVVQTPVRSRRILWDQFHNIKYPSGYV
PRDSLNVNNDILDWHGDHLHTNFHILFNMLRDAGYYVETLGSPLTCFDASNYGTLLMVDLEDEYFSEEIQ
KLRDDVVHKGLGLAVFAEWYHVDTMVKMTFFDENTRSWWSPLTGGANIPALNELLAPFGIAFGDKILSG
DFSINGEQSHYASGTDIVQFPAGGFLHGFELQEDPKTAQNSSTPDTQNSQSQEKSKLSSILGMLEAGEGRIA
VYGDSNCLDSSHMVTNCYWLLRKIVEFAGNGLRDPVLFSEATRLKFPVFENIQKPLRRPDVNFSMFSSVIG
KELICHQDSRFEVWGTKGYGIQLTGTTRKLPEYQKNEVSSSPNRLIKSSYKRQDEAGLQKSILAPSANKFD
DNRDYFGFISHEEVASQWMVPACFAVTTCILVYLSCRAQQRRRRPRKGSATGRLSSSV

Figure 3

Nucleic acid sequence of subtilisin RNR9 from Hordeum vulgare (barley); HvRNR9

CGGCACGAGGCTCTGGTGGTCGGAGGCGGAAGCTTCAAATGCGGAGATCACATGTGACATCTCTTTT
TGGAGCTGCACAGCTATGGGAAAGAGGCTTCACTGGTAGGAAAGTCAAAATGGCCATTTTTGACACT
GGTATTCGGGCGGACCACCCACACTTCCGTAATATTAAGGAGCGCACAAATTGGACAAATGAAGACA
CATTAAATGACAACCTTGGTCATGGAACATTCGTAGCTGGAGTGATTGCTGGTCAAGATCCAGAATG
TCTTGGATTTGCACCAGACACTGAGATATATGCATTTCGAGTGTTCACAGATGCTCAGTGCAGATATC
CTACACATCATGGTTCTTGGATGCATTTAATTATGCTATGGCTACTGGTATGGATGTATTGAATTTGA
GTATTGGTGGACCTGATTACCTGGATCTCCCCTTTGTGGAAAAGG

Figure 4

Protein sequence of subtilisin RNR9 from Hordeum vulgare (barley); HvRNR9

ARGSGGRRRKLQMRRSHVTSLFGAAQLWERGFTGRKVKMAIFDTGIRADHPHFRNIKERTNWTNEDTLN
DNLGHGTFVAGVIAGQDPECLGFAPDTEIYAFRVFTDAQCRYPTHHGSWMHLIMLWLLVWMY*I*VLVD
LITWISPLWKR

Wherein an asterisk (*) may indicate a frameshift in the corresponding nucleotide sequence, and an alternatively translated, shifted amino acid sequence should be taken into consideration.

Figure 5

Nucleic acid sequence of SUB1_6_neu from Arabidopsis thaliana

```
ATGGGGATGA CCGTCGTAAT TATTCTGGTG TTCTCATTTT TCGTAGCGAT
TGTAACGGCGGAGACCTCTC CTTACATCAT CCACATGGAC TTATCCGCTA AACCGTTGCC
ATTTTCCGATCATCGGAGCT GGTTTTCCAC AACTCTTACT TCAGTTATAA CCAATAGAAA
ACCAAAGATTATCTACGCTT ATACCGATTC GGTTCACGGG TTTAGCGCGG TTCTCACCAA
CTCTGAGCTC AACGTCTTA AACACAAACC CGGGTATGTC TCGTTCACCA AAGATTTACC
GGTTAAGCTTCATACCACTT TCTCTCCAAA GTTTATCGGT TTAAATTCGA CATCCGGTAC
ATGGCCGGTCTCGAATTATG GAGCTGGTAT AGTAATCGGT ATTATAGATA CCGGAATTTG
GCCCGATAGTCCCAGCTTTC ACGACGATGG GGTTGGTTCG GTTCCGTCTA AATGGAAAGG
AGCATGTGAATTCAATTCTT CTTCCTTGTG CAACAAGAAA CTAATCGGTG CTAAGGTATT
CAACAAGGGTTTGTTCGCCA ACAACCCTGA TTTGAGAGAA ACCAAGATTG GCCAATACTC
TTCACCGTACGATACAATCG GACACGGCAC TCATGTTGCA GCCATTGCAG CTGGGAATCA
TGTTAAGAACGCGTCTTACT TCTCTTACGC CCAAGGAACC GCCTCAGGAA TCGCACCACA
CGCGCATCTAGCAATCTACA AAGCCGCGTG GGAAGAAGGG ATTTACTCAT CAGATGTAAT
CGCAGCGATTGATCAAGCGA TTCGAGATGG AGTCCATGTG ATATCTCTGT CGCTAGGATT
GAGTTTTGAGGATGATGACG ACAATGATGG TTTCGGTCTA GAAAATGATC CAATCGCAGT
CGCATCTTTTGCAGCGATTC AAAAAGGCGT TTTCGTGGTT ACTTCCGGCG GTAACGACGG
GCCATATTACTGGAGTTTGA TTAACGGAGC GCCGTGGATT ATGACGGTTG GAGCGGGAAC
AATTGGTAGGCAATTTCAAG GAACCCTAAC GTTTGGAAAC AGAGTTAGTT TCAGTTTTCC
ATCTCTGTTTCCTGGAGAGT TCCCTTCGGT TCAGTTTCCA GTAACTTACA TCGAATCTGG
CAGCGTTGAAAACAAGACTC TCGCAAACAG AATTGTTGTC TGTAACGAAA ACATAAACAT
CGGTAGCAAACTTCATCAAA TCAGATCCAC CGGAGCTGCA GCAGTAGTTT AATAACAGA
TAAGTTACTT GAGGAGCAAG ACACAATAAA ATTCCAGTTT CCAGTAGCAT TCATCGGCTC
AAAACACCGAGAAACTATTG AAAGCTACGC ATCAAGCAAC AAAAACAACG CGACCGCAAA
GCTGGAGTTTCGTAAAACGG TAATCGGGAC AAAACCAGCG CCAGAAGTTG GCACATACAG
CTCAAGGGGTCCATTCACAA GCTTCCCTCA AATCCTGAAA CCAGACATTC TAGCTCCTGG
GACACTTATACTCTCTGCTT GGCCGTCGGT TGAGCAAATC ACCGGAACTC GAGCACTACC
GTTATTCAGCGGATTCAATC TCTTAACCGG GACATCAATG GCTGCACCTC ATGTAGCTGG
AGTCGCTGCGCTTATAAAGC AAGTCCATCC AAATTGGAGT CCATCGGCTA AAAATCTGC
AATTATGACAACGGCTTTGA CTTTAGACAA CCCATTAGCC GTTGGAGCAG GCATGTGAG
TACGAACAAAGTCTTAAACC CTGGCCTAAT CTATGATACA ACTCCACAAG ATTTCATAAA
CTTCCTTTGTCACGAGGCAA ACAATCAAG AAAATTGATC AATATCATCA CGAGATCGAA
TATCTCCGACGCTTGTAAAA AGCCATCTCC ATATCTCAAT TACCCTTCAA TCATTGCCTA
CTTCACGTCTGATCAAAGCA GTCCCAAGAT CTTTAAGAGG ACATTGACAA ACGTGGGAGA
AGCAAAGAGAAGCTACATCG TGAGAGTGAG AGGCTTGAAG GGTCTAAACG TCGTCGTAGA
GCCAAAGAAACTAATGTTCA GCGAGAAAAA CGAGAAGCTA AGCTACACTG TGAGATTGGA
GAGTCCAAGAGGGTTACAAG AGAACGTGGT TTATGGATTG GTGAGTTGGG TTGATGAAGA
TGAAGCTGAGTTTGAAGTGA GCTGTTCTGT GGTGGCCACG AGCCTTGTCC AAGAGTCTTG A
```

Figure 6

Protein sequence of SUB1_6_neu from Arabidopsis thaliana

MGMTVVIILVFSFFVAIVTAETSPYIIHMDLSAKPLPFSDHRSWFSTTLTSVITNRKPKIIYAYTDSVHGFSA
VLTNSELQRLKHKPGYVSFTKDLPVKLHTTFSPKFIGLNSTSGTWPVSNYGAGIVIGIIDTGIWPDSPSFHD
DGVGSVPSKWKGACEFNSSSLCNKKLIGAKVFNKGLFANNPDLRETKIGQYSSPYDTIGHGTHVAAIAAG
NHVKNASYFSYAQGTASGIAPHAHLAIYKAAWEEGIYSSDVIAAIDQAIRDGVHVISLSLGLSFEDDDDND
GFGLENDPIAVASFAAIQKGVFVVTSGGNDGPYYWSLINGAPWIMTVGAGTIGRQFQGTLTFGNRVSFSFP
SLFPGEFPSVQFPVTYIESGSVENKTLANRIVVCNENINIGSKLHQIRSTGAAAVVLITDKLLEEQDTIKFQFP
VAFIGSKHRETIESYASSNKNNATAKLEFRKTVIGTKPAPEVGTYSSRGPFTSFPQILKPDILAPGTLILSAW
PSVEQITGTRALPLFSGFNLLTGTSMAAPHVAGVAALIKQVHPNWSPSAIKSAIMTTALTLDNPLAVGAGH
VSTNKVLNPGLIYDTTPQDFINFLCHEAKQSRKLINIITRSNISDACKKPSPYLNYPSIIAYFTSDQSSPKIFKR
TLTNVGEAKRSYIVRVRGLKGLNVVVEPKKLMFSEKNEKLSYTVRLESPRGLQENVVYGLVSWVDEDEA
EFEVSCSVVATSLVQES

Figure 7

Nucleic acid sequence of SUB1_8_neu) from Arabidopsis thaliana

```
ATGGTTAGAG TAATGTTGGT GAGGTTTGGG TTTTTATTAC TTATGATCTC
TTTTGTGTTTTTGTCTAATA ACACTTTGGG ACAACAACAA GACGATGATG ATGATTCTGC
TGTGTACATTGTCACACTTA AACAACCTCC TATTGTCCAT CTCTTTGAAG AACAAGAGCT
TAAACACAAAAAGTCAAAGT TTACACCAAA ATTGCGACCA AGGAACAATT CAAGGAAACG
TCATGGGAAGTCAAAGATAC CATCTGTTGT TCAATCTCAT GACTCTTTCT TGAGAAAGAC
TCTAAAAGGAGAGAAGTATA TAAAGCTTTA TAGTTACCAT TATCTTATCA ATGGATTTGC
TCTGTTTATTAACTCACAAC AGGCTGAGAA GCTTTCAATG AGAAAAGAAG TAGCAAACAT
AGTGTTGGATTACTCTGTTA GGACAGCAAC AACTTATACT CCACAGTTTA TGGGTTTACC
ACAAGGAGCATGGGTCAAAG AAGGTGGATT TGAGATTGCT GGAGAAGGAG TTATAATCGG
TTTTATCGATACTGGGATCG ATCCGAATCA TCCTAGTTTC AATGACAATGACTCTAAGCG
TTCATATCCAATCCCTAAGC ATTTCTCAGG TGTTTGTGAA GTTACACCGG ATTTTCCATC
AGGATCTTGCAATAAGAAGC TTATTGGAGC ACGGCATTTC GCGCAATCCG CTGTAACCAG
AGGAATCTTTAACTCATCTG AAGATTACGC TTCTCCTTTC GATGGAGATG GACATGGAAC
ACACACAGCTTCGGTTGCAG CGGGTAACCA CGGAGTTCCA GTGATAGTTT CTAACCATAA
CTTTGGATACGCTAGTGGAA TCGCTCCTCG TGCATTTATT TCTGTTTACA AGGCATTGTA
TAAGAGTTTTGGAGGTTTTG CTGCAGATGT TGTAGCAGCT ATAGATCAGG CAGCTCAAGA
TGGAGTAGATATATTAAGCC TATCAATTAC ACCGAATCGG AAACCTCCCG GTGTTGCCAC
TTTCTTTAATCCTATCGACA TGGCATTACT TTCCGCTGTA AAAGCCGGAA TCTTCGTAGT
CCAAGCTGCGGGAAATACCG GTCCAGCGCC TAAAACCATG TCTTCTTTTA GTCCTTGGAT
ATTCACCGTTGGTGCTTCTT CTCATGATAG AGTTTACTCT AATTCTTTAA CCTTAGGAAA
CAATGTAACTATTCCAGGCA TGGGATTCGC AATTCCTACA GATAGTGGAA AAATGTACAA
GATGATATCTGCTTTTCATG CCTTGAACAA TAGTACTTCT GTAGATAAAG ATATGTATGT
AGGTGAATGTCAAGATTATG AAAACTTCGA TCAAGATCGT GTCTCAGGGA AACTTTTGAT
ATGTAGCTACTCTGCTCGTT TTGTTCTCGG GCTTTCGACT ATAAAACAAG CTTTAGATGT
TGCCAAGAATCTATCCGCGA CTGGTGTGAT ATTCTATATA GACCCGTATG TTCTTGGTTT
TGAGATCAATCCAACACCGA TGGATATGCC CGGGATCATA ATTCCATCTG TAGAAGATTC
CAAGACTTTACTCAAGTACT ATAACTCTTC TATTCAAAGA GATGTAACCA CTAAAGAAAT
TGTTAGTTTTGGAGCGGTTG CAGCCATAGA AGGCGGTTTA AATGCTAACT TTAGTAACAG
AGCTCCTAAGGTAATGTATT ACTCAGCAAG AGGACCTGAT CCTGAAGACA ACTCTTTTAA
CGACGCAGACGTATTAAAAC CGAACCTCGT AGCACCTGGA AACTCTATTT GGGGTGCTTG
GAGTTCTGCTTCAACGGATT CTACCGAGTT TGAAGGTGAG AAATTTGCGA TGATGTCCGG
TACAAGTATGGCTGCTCCTC ATGTAGCTGG TGTGGCTGCA TTAATCAAAC AAAGTTATCC
ACAGTTTACTCCTTCAACAA TCTCATCCGC GCTTTCAACA ACGGCTCTCC TAAATGATAA
TAAAGGCAGTCCGATAATGG CTCAGCGAAC TTATTCCAAT CCCGATCAAA GCCTCTATAC
CGCAACACCGTCTGATATGG GGAGCGGTTT TGTTAACGCA ACGGCAGCTT TAGACCCTGG
TCTAGTTTTTGATACAAGTT TTGAAGATTA TATATCATTT CTTTGTGGGA TCAACGGCTC
GGATACGGTGGTATTCAACT ACACCGGATT CCGCTGTCCC GCTAACAACA CACCAGTCAG
TGGTTTTGACCTCAATTTGC CATCAATTAC AGTATCGACA CTTAGTGGCA CACAAACTTT
CCAAAGATCGATGAGAAACA TAGCCGGCAA TGAGACATAC AATGTTGGTT GGAGTCCTCC
TTATGGTGTTTCAATGAAAG TATCACCTAC TCAATTTTCT ATTGCTATGG GAGAAAATCA
AGTACTTAGCGTAACCCTCA CGGTGACAAA GAACAGTTCC AGTTCTAGTT TTGGCAGAAT
CGGATTGTTTGGAAATACAG GACACATTGT TAATATTCCT GTAACTGTCA TAGCGAAAAT
CGCTTCGAGCTGA
```

Figure 8

Protein sequence of SUB1_8_neu) from Arabidopsis thaliana

MVRVMLVRFGFLLLMISFVFLSNNTLGQQQDDDDDSAVYIVTLKQPPIVHLFEEQELKHKKSKFTPKLRP
RNNSRKRHGKSKIPSVVQSHDSFLRKTLKGEKYIKLYSYHYLINGFALFINSQQAEKLSMRKEVANIVLDY
SVRTATTYTPQFMGLPQGAWVKEGGFEIAGEGVIIGFIDTGIDPNHPSFNDNDSKRSYPIPKHFSGVCEVTP
DFPSGSCNKKLIGARHFAQSAVTRGIFNSSEDYASPFDGDGHGTHTASVAAGNHGVPVIVSNHNFGYASGI
APRAFISVYKALYKSFGGFAADVVAAIDQAAQDGVDILSLSITPNRKPPGVATFFNPIDMALLSAVKAGIF
VVQAAGNTGPAPKTMSSFSPWIFTVGASSHDRVYSNSLTLGNNVTIPGMGFAIPTDSGKMYKMISAFHAL
NNSTSVDKDMYVGECQDYENFDQDRVSGKLLICSYSARFVLGLSTIKQALDVAKNLSATGVIFYIDPYVL
GFEINPTPMDMPGIIIPSVEDSKTLLKYYNSSIQRDVTTKEIVSFGAVAAIEGGLNANFSNRAPKVMYYSAR
GPDPEDNSFNDADVLKPNLVAPGNSIWGAWSSASTDSTEFEGEKFAMMSGTSMAAPHVAGVAALIKQSY
PQFTPSTISSALSTTALLNDNKGSPIMAQRTYSNPDQSLYTATPSDMGSGFVNATAALDPGLVFDTSFEDYI
SFLCGINGSDTVVFNYTGFRCPANNTPVSGFDLNLPSITVSTLSGTQTFQRSMRNIAGNETYNVGWSPPYG
VSMKVSPTQFSIAMGENQV

Figure 9

Nucleic acid sequence of SUB RNR9 from Zea mays (maize); ZmSubtilisin RNR9

GATATATCCA ACAACCACGC AGTGCATACA TGCTTGATTT TCCTGCCCAT
CGATCATATCGTCAACTGGT CCGGCAGTTC TCCGACACCA TGAGCTCCTC GGAGTGCGGC
GGCGGCGGCGGTCGGCGCCA ANACGTCGTG GCCGGAGGTG GTCGGGCTGA GCGTGGAGGA
CGCCAAGAAGGTGATCCTCA AGGACAAGCC GGACGCCGAC ATCGTGGTGC TGCCCGTCGG
CTCCGTGGTGACCGTGGATT ATCGCCCTAA CCGTGTCCGC ATCTTC

Figure 10

Protein sequence of SUB RNR9 from Zea mays (maize); ZmSubtilisin RNR9

DISNNHAVHTCLIFLPIDHIVNWSGSSPTP*APRSAAAAAVGAXTSWPEVVGLSVEDAKKVILKDKPDADI
VVLPVGSVVTVDYRPNRVRIF

Wherein an asterisk (*) may indicate a frameshift in the corresponding nucleotide sequence, and an alternatively translated, shifted amino acid sequence should be taken into consideration.

Figure 11

Nucleic acid sequence of SUB RNR9 from Oryza sativa (rice)

ATGGCGCCAG ATGAGGGCGA CGGCTATCGA TCTACACCAG CATACGTCGG
GTTACAGATCGAACTGGCAA CCGGCGGCGC TGCGTGCAGA CAACGGTTGC TACCGATCTA
CATCAACAAATATCGTCGGG CTACGGATCA GATCGGCGAC CGGCGGCCTC ACGGTGCGGT
CTCCGCCCCGGACTCCGGGA TTGCACCGTG GATTAGGGTT CTGGGAGGTG TGATGGACAA
AGGGGGAAAGAAGAAGGGGG TGGACCTGGA AGGCCTCTTC CTAGGTCTTA AGCTGTCCCG
GGAGGAATTGAGAGGCATGA AAGGATCTTG GTGCTTGGAG GAGAAGGATG GCGGAAAAGT
TCAACAGGCAGTGGGGAAGT TATTCTCTCC ACGAGCAGGG GTGTACAATC TGCCGTTCGG
CTTGATGAAT      GTGGATACTG GCCGGGTAAT TGGGAATAAA ATTGGGAAAG CATTGGAGGT
TGATACGGATGAGGATGGGT CAGCCGTGGG AGGTTATCTG CTGGTGAAGG TGCTCATGGA
TGCCCGCAAAGCCCTAATCG GCGGGGTGAT GATGGAGGGT GTCGCCGGTG AGAAGGAGAA
TTGGTGTGGAGTGAAGTACG AGTTCCTGCC AAATTTTTGT TATTCCTGCG GCGTTCTGGG
TCATGTGGAGGAGTGTGATG ATAAGGTATG GAAGGAGGAA GAGCAGCAAT TCGGGGACTG
GTTGCGAGTCCTACCGATGA AACAGCGGGA TGTGCGAGGC TGGAGCTCGG AAGGGGGCAG
TTCTGGGGGTTCGTTTCAGC ACAGGAGTGT CGTATCCTGG AGGAAAAGTG GAGTTGAGAA
AGGAGGTAGC      AGCGGTGTAG GTGGAAAATC TGCTAGCCGG GATGACCCTG AACTAAGGGA
TGATGCTGAAAGCCCGGGTA AAGGGCATCC CAAGATCCGG ATGGGCGGTG CTCCGAAGAA
GCTGACCTTTGTCGGTGATG GTAGTTCGGG GAGTTTGACT GAGGAGAGAG GGCATAAAAA
GCTGCTGGAGATTACGGCTC CCTCGGAGCC GCAACTAGTT CCGACCACGG GTGAAGTAGC

Figure 11 of 18 (Continued)

```
TAGTGGGTTAGATGGAGAGG ACGCTCGGGG GAAGGAGCAC AGTACCATGC AGGTTCCTGT
GGGGGGAGGAGTAAAGGACA AACACACTCT CCCGTTGGCT GCTGAAAGTG GTACTTTGGA
TACTGGGCACTCGGGGACGG GAGATAAGAG GAAGGCCACT TTCAAGCGGC GTCCGCGAGT
GATGGATAAG   GAAGTCGGCG CCAAGGAGAG CGCGATTGCT GATACTCGAA AGTGCTCTGT
AACGGAGGAGATGGTTGTGA CCGAAGAACG GAAGAAACAG AATGCTCAGG TGGCTGTGAG
TGATGACGCTTCCAAGTTCG TGGCCTTCTG GATATCCAGA GGGAGGAGGA TCCCGATGTT
CTGTTTATTTCGGAGACGAA AAAAGGTGGA AGGGGGAGCT CCTCGGTCCG AAAGTTGTAT
GGCCAAGTTTCGACAGGCTT TGGAGGACTG CCAGCTGCAT GATCTGGGTT TTGTTGGGGA
TGCCTTCACGTGGAGGAATC ACCATCACCT GGCGTCCAAC TACATAAAGG AAAGACTTGA
TAGAGCAGTGGCCAATGGTG CCTGGCGAGC ACGCTTCCCG CTTGTTCGCG TAATCAATGG
GGATCCGCGC   CACTCAGAC ATCGTTCGGT CATTGTGGAA ACCGGTGCCA CTGAAAAACA
ACAATGGGGGCAACCTTTGG AGATTATGCA GAAGTTTGAG GCTCGTTGGC TGGAGGAAGA
AGAATGCCAGGCCAGAGTGG AGGAAGCGTG GGAGAATGCA TTGGAAGGTG GTCAAACTCG
GCTAATGGAGATCCAAAGCC GGGTCCTGAA GGAATTATGG GCTTGGGACC GCACTGTCCT
GGGTGAGTTGAAGAAGAGGG TTAAAAATCT AAGGAAGGAA TTGGAGAAGT GCAGGAGGGA
GCCAATCTCTAACCGGCAAG TTAACAGAGA ACATTTGTTG CGGTACAAGT GAGGCGGCT
GCTGGATCAACAACATATTT ACTGGAAGCA GCGAGCACAT TCTACCTGGT TAACCAAGGG
CGACCGGAAC   ACAAAGTTT TCCATGCCCA AGCATCGGAG AAGAAGAAAA GAAATACAAT
ACAGAAGTTGCAGGATGGCC ACGGTGGTTT GGTTGCTGGA AATCAACTAA AAAGCTTCAT
TTCGAACCAGTACCAACAAC TCTTTAGGTC GAATGGGTGC TCTCAGATGG ATGCAGTATT
ACAATGTGTCCAAGCGCGTG TGACCCCGGA GATGAGAGAA GGCCTTGCTG CTCCTTATCA
GAGAGAGGAAGTTTGGGTGG CTTTAAAGGA TATGGGGGAT TTAAAGGCAC CAGGCGCAGA
TGGTATTCCAGCAATCTTCT ACAAAAAATT TTTGTCACTA GCTGGCGATA AGGTGAAGGA
TGAGGTGCTGGCGGTTCTTA ATGGTGGGGA TATGCCACAG GGATGGAACG ATACAGTTGT
GGTATTAATA   CCAAAGACGA AACAGCCGGA CACATTGAAA GACTTGAGAC CGATAAGTTT
ATGCAATGTGGCATATAAAC TGATCTCCAA GGTGATAGTC AATCGGTTGA AAGTTGTGCT
GCTGGAAATAATCTCTCCGT CCCAAAGTGC GTTTGTCCCG AGGAGGTTGA TCACATACAA
TGTATTACTGGCATATGAGC TCACACACTA CTTGAATCAA AGGAAGAAGG GGAAGAATGG
AGTGGCTGCGATCAAGCTGG ACATGAGCAA GCTTACGAT AGGGTGGAAT GGGATTTCCT
GCGACACATGATGCTGAGGT TGGGCTTCCA TGATCAGTGG GTTAACTTAG TCATGAAGTG
TGTAACTTCTGTGACTTACC GGATCAAGAT CAATGGGGAG CACTCAGATC AAATATACCC
ACAGAGGGGG   CTGAGGCAGG GAGATCCACT TTCCCCTTAC TTGTTCATTA TTTGTGCGGA
AGGCCTTTCAGCGCTATTAC AGAAAGCACA AGCTGATGGA AAGATAGAGG GTATTAAAGT
TTGCAGGGACACGCCAAGAA TAAACCATCT CTTTTTCGCC GATGATTCCC TTGTCCTGAT
GCGAGCTGGCCAGAATGATG CGCAAGAGTT GAGAAGGGTT CTTAACATAT ACGAAGTGGC
ATCAGGCCAAGTCATAAACA AGGACAAATC ATCTGTCCTC TTCAGCCAA ACACACTTCA
GAGTGATAGGATGGAAGTTA GATCAGCGCT ATGTATTAAT CAGGAGGCAA AAAATGAAAG
ATATCTTGGCCTGCCTGTCT CTATTGGGAA GTCAAGGAGG AAAGCTTTTG AGTATATTAA
GAGGAAGGTG   TGGCTCCGGA TCCAGGGTTG GCAGGAGAAA TTACTATCAA AGCAGGGAA
GGAAATCCTTGTCAAAGCTG TGGCCCAAGC TATTCCTACC TATGCGATGT CATGTTTTGA
TTTGACTAAAGGTTTATGTG ATGAAATCAA TTCCATGATT AGCAAGTGGT GGTGGAGCCA
GAATGACAAGGAAAATAAAA TACACTGGCT GTCGTGGGAG AAGATGACGC TCCCTAAAAA
GCTTGGCGGGGCCAGGATTCC GGGATCTTCA TCTGTTCAAC ATGCGATGC TTGCTCGGCA
GGCATGGCGGCTCCTCCTAA ATGTAGACTC GCTCTGTGGG CAAGTCTTTG TTGACGAAAA
AATCGAACACACCGGCCTGG GAGATCTGCT TAGCTCCTGT GCAAGTCCAA AGATTGATGA
GATGCGGGCG   TGCCAGTCG TTTGA
```

Figure 12 of 18

Protein sequence of SUB RNR9 from Oryza sativa (rice)

```
MAPDEGDGYRSTPAYVGLQIELATGGAACRQRLLPIYINKYRRA
TDQIGDRRPHGAVSAPDSGIAPWIRVLGGVMDKGGKKKGVDLEGLFLGLKLSREELRG
MKGSWCLEEKDGGKVQQAVGKLFSPRAGVYNLPFGLMNVDTGRVIGNKIGKALEVDTD
EDGSAVGGYLLVKVLMDARKALIGGVMMEGVAGEKENWCGVKYEFLPNFCYSCGVLGH
VEECDDKVWKEEEQQFGDWLRVLPMKQRDVRGWSSEGGSSGGSFQHRSVVSWRKSGVE
KGGSSGVGGKSASRDDPELRDDAESPGKGHPKIRMGGAPKKLTFVGDGSSGSLTEERG
HKKLLEITAPSEPQLVPTTGEVASGLDGEDARGKEHSTMQVPVGGGVKDKHTLPLAAE
SGTLDTGHSGTGDKRKATFKRRPRVMDKEVGAKESAIADTRKCSVTEEMVVTEERKKQ
NAQVAVSDDASKFVAFWISRGRRIPMFCLFRRRKKVEGGAPRSESCMAKFRQALEDCQ
LHDLGFVGDAFTWRNHHHLASNYIKERLDRAVANGAWRARFPLVRVINGDPRHSDHRS
VIVETGATEKQQWGQPLEIMQKFEARWLEEEECQARVEEAWENALEGGQTRLMHIQSR
VLKELWAWDRTVLGELKKRVKNLRKELEKCRREPISNRQVNREHLLRYKLERLLDQQH
```

Figure 12 of 18 (Continued)

IYWKQRAHSTWLTKGDRNTKFFHAQASEKKKRNTIQKLQDGHGGLVAGNQLKSFISNQ
YQQLFRSNGCSQMDAVLQCVQARVTPEMREGLAAPYQREEVWVALKDMGDLKAPGADG
IPAIFYKKFLSLAGDKVKDEVLAVLNGGDMPQGWNDTVVVLIPKTKQPDTLKDLRPIS
LCNVAYKLISKVIVNRLKVVLLEIISPSQSAFVPRRLITYNVLLAYELTHYLNQRKKG
KNGVAAIKLDMSKAYDRVEWDFLRHMMLRLGFHDQWVNLVMKCVTSVTYRIKINGEHS
DQIYPQRGLRQGDPLSPYLFIICAEGLSALLQKAQADGKIEGIKVCRDTPRINHLFFA
DDSLVLMRAGQNDAQELRRVLNIYEVASGQVINKDKSSVLFSPNTLQSDRMEVRSALC
INQEAKNERYLGLPVSIGKSRRKAFEYIKRKVWLRIQGWQEKLLSKAGKEILVKAVAQ
AIPTYAMSCFDLTKGLCDEINSMISKWWWSQNDKENKIHWLSWEKMTLPKKLGGPGFR
DLHLFNMAMLARQAWRLLLNVDSLCGQVFVDFKIFHTGLGDLLSSCASPKIDEMRACQSV

Figure 13 of 18

Consensus sequence 1 comprising the amino acids with color code (a) [see page 62 of the description] from the sequence alignment as shown in Figure 16

```
XXXXXXXXXXRXXXXXXXXXXXXXXXXXXXXXXXXXXXXXXXXXXXFXXXXXXXXXXXXXX
XXXXXXXXXXXXXXXXXXXXXXXXXXXLXXXXXXXXXXXXXXXXXXGXXDXXXXXXXXSXXX
XXXXXXXXXXXXXXXXXXXXXXXXXXXXXXXXXXXXXFXXXXXXXXXXXXXXXXXXXXXXX
XDXXGHGTXXAXXXAGXXXXXXXXXXXXXXXXXGXAPXXXXXXXXXXXXXXXXXXXXXXAXXX
AXXXGXXXXXLSXXXXXXXXXXXXXXXXXXXXXXXXXXXXXXXXVXXXGNXGPXXXXXXXX
XXXXXXXGXXXXXXXXXXXXXXXXXXXXXXXXXXXXXXXXXXXXXXXXXXXXXXXXXXXXX
XXXXXXXXXXXXXXXXXXXXXXXXXXXXXXXXXXXXXXXXXXXXXXXXXXXXXXXXXXXXX
XXXXXXXXXXXXXXXXXXXXXXXXXXXXXXXXXXXXXXXXXXXXXXXXXXXXXXXXXXXXX
XXXXXXXXVXXXXXXXXPXXXXXXXXXXXXXXXXXXPXXXXXXXXXXXXXXXXXXXXXXXX
XXXXXSXXXPXXXGXXXXXXXXXXXXXXXXXXXXXXXXXXXXXXXXXXXXXXXXXXXXXXX
XXXXXXXXXXXXXXXXXXXXXDXXXXXXXXXXXXXXXXXXXXXXXXXXXXXXXXXXXXXXX
XXXXXXXXXXXXXXXXXXXXXXXXXXXXXXXXXXXXXXXXXXXXXXXXXXXXPXXXXXXXX
XXXXXXXXXXXXXXXXXXXXXXXXXXXXXXXXGXXXXXXXXXXXXXXXXXXXXXXXXXX
```

Figure 14 of 18

Consensus sequence 2 comprising the amino acids with color code (a) and (b) [see page 62 of the description] from the sequence alignment as shown in Figure 16

```
LXPRPXSDHRXXXSXXLXXVXXXXXXXXXXXXXXXXXXXXXYXYXXXXXGFAXXXXXXXXXXXLXHRX
XVXXXXXDLXVXXXXHTTXSPXFXGLXXXXXXXXXXXXXXXGEGXXIGXIDTGLXPNXPSFXDXGXXRX
XXXPXXXXGXCEXXXXXXXXXXCNKKLIGAXXFXXGXXAXXXXXXXIXXXXXXXXXXSPXDXXGHGT
HVAXVAAGNHXXXXXXXXXXXXGXASGIAPXAXIXXYKAXXXXXXXXYXSDVXAAIDQAXXDGVDVLS
LSIGXXXXXDXXXXXFXXXNXPIXXAXXXAXXXGIFVVXAXGNDGPXYXTLXNXAPWIXTVGAGXIDR
XXXXXLTXGNXVTXXXXXXXXGXXXXXVXXXXXXIXXXXSTXXXXXXXXXXXXXXXVXXXXVA
GXXXXCXXXIXXXXXXSXIXXALXXXXXXXAAXVXXXXDXYXXGXXXXEXXXXXXXXPXXXIXSXX
XXXXXXXXXXXXXXXYXSSXXXXXTXKXXFXXTXXXXXXXXXXXXXXXAPXVXXYSXRGPXXXX
XXXXXXXXXLKPDXXAPGTXILXAWXSVXXXXXXXFXGXXXXXFXXXXGTSMAAPHVAGVAALIKQXXP
XXXPSXIXSAXXTTALXLDNXXXXIXXXXXYXXXDXXXXXXXPLDXGXGHVXTNXXLXPGLXXDTXX
XDXIXFLCXXXXXXXXXXXXNXXXXXXXXXXXXXXXXXXXXXXXXXLXXXXXSXXSXXXTFXRXXX
NXXXXXXXXSYXVGXXXXXGLNXXVXPXXXXFXXKXXXXXXXXXXEXXXXXXXXXXXXXXXXXX
XXGXXXXXDXXXAXXXXXXVXAXXXXXXS
```

Figure 15

Primer Sequences as given on page 68 (in 5'-3'-direction)

Upper Primer: CGGCACGAGGCTCTGGTGGT

Lower Primer: CCTTTTCCACAAAGGGGAGA

Figure 16 of 18
Protein sequence alignment

Wheat ortholog of RNR9

```
                              1                                                                           80
Wheat ortholog of RNR9 (Subtilase)  (1) ----------------MPPPAMAEKRRAAYAAFLPLLLLLATRAALPSSDPPARGGEETASSRYVVRFLEYRADDHREYL
                       SUB1_8_neu  (1) MVRVMLVRFGFLLLMISFVFLSNNTLGQQDDDDDSAVYIVTLKQPPAVHLFEEQELKKKSKFTPKLRPNNSRKEHGK
                       SUB1_6_neu  (1) ----------------------------------MGMTVVIIFVSFFVAVTMETSPYIIEMDL----SAKPEFSDERSWF
                        Consensus  (1)                                              LV L     IV A       E H      L PRP SDER 81                                                                          160
Wheat ortholog of RNR9 (Subtilase) (68) EDGIPREAGPWRW----------VERRNPAAAHPTDAVLEIR-D---AHRDAVSEAIRAIARVRDVHPDTSHSRAATSA
                       SUB1_8_neu (81) SKIPSVWQSHDSFLRKTLKGEKYIKLMSHYLINCELFINSQQAEKISMRKEVANIVIDYSMR--TATYTPQFMGLPQ
                       SUB1_6_neu (46) STTLTSVITNRK--------PKIIVATDSVHCESAVLTNSELQRKEKPGYVSFTKDPVK--LHTVFSPKFICENS
                        Consensus (81) S L V                             Y Y  GFA          L HR  V      DL V     HTI SP F GL 161                                                                          240
Wheat ortholog of RNR9 (Subtilase)(134) DRARGKRFTAMSFEEGRGGDSDAVPSNNASSSSGGPRRKLQMRRPHVTSLFGAAQLWERGFTGRKVKMAIDTCIRADH
                       SUB1_8_neu(159) GAWVKEGGFEIAGCVITFIKTGIDPNHPSFNDSKRSYPIPKHFSCCEVTPDFPSGG---LCNKKLIGAKRHFAQSAVTRG
                       SUB1_6_neu(114) TSGTWFV--SNYCACIVKSIIBTGIMDSPSFHDDGVG---SVPSKWKCACEFNSSS----LCNKKLIGAKVNKGLFANN
                        Consensus(161)              GEG  IG IDTGI FN PSF D G  R        P     P   G CE     CNKKLIGA F G   A 241                                                                          320
Wheat ortholog of RNR9 (Subtilase)(214) PHFRNIKERTNWTNEDTLNDNLGHCSFYAGVIAG-------------QDPECGFAANTEIYAFRVFTDAQISTWFLDAF
                       SUB1_8_neu(239) ----IFNSSEDYA---SPFLGDGSHCETASVAAGNHGVPVIVSNHECYASCIRERAFISVYGLYKSFGFAADVVPAHI
                       SUB1_6_neu(186) -PDLRETKIGQYS---SPIBTICHLHVKAIDACNHVKNASYFSYAQCTASCIRPHLHLAIYCAAWEEG-LSDVIARI
                        Consensus(241)     I           SP D GHGTHVA VAAGNH               G ASGIAP A I   YKA    Y SDV AAI 321                                                                          400
Wheat ortholog of RNR9 (Subtilase)(283) NYRMATCSDVIANISIGGPDYLDLPFV------EKV-WELTANNIIIMSAIGNDPFLCIINNPADQSDVIGVGGIDY
                       SUB1_8_neu(312) DCRAODAVDILSRITPNRKPPGVATFN---N-PIDMALLSAVKAGIFVCAAGHTCEAPKHMSSFSPWIFTVCASSHDR
                       SUB1_6_neu(261) DCHIRDAVFIVISIIGLSFEDDDNDGGLENDPIAVASFARIQKCVENTSGGNDSPYWSHINGAPWIKNEAGTIGR
                        Consensus(321) DQA     DGVDVLSLSIG     D   F  N PI A   A    GIFVV     A   GNDGP Y TL N APWI TVGAG IDR 401                                                                          480
Wheat ortholog of RNR9 (Subtilase)(353) NNHIASFSSSRGMTTWELPHGYGRVKPDTWGSKTISTGC-------KTLSGTSVASPVVAGAVCLLVSVIPEDKR
                       SUB1_8_neu(388) VYSNSTLGNNVIIPGMGFAIPTDSGKMYKMISAFHALNNSTSVDKDMVGECQDYENFQDRVSGKLLICSYSARFVLG
                       SUB1_6_neu(341) QFQGTLIFGRVSFSFPSLFPGEFP-SMQFPVTYIESGS-------VENKTLANRIVVCNEMI-
                        Consensus(401)                                       G   V   I     ST              V    VAG   C  I
```

Figure 16 of 18 (Continued)

```
                          481                                                                                                      560
Wheat ortholog of RNR9  (426) KSILNP SMKQALVEG SKLVGPNI EQ AGKPDLWQSYEILKNYQPRASVFPNMLDFTDCPYFWPFCRQPLYAGAMPVV
              SUB1_8_neu (468) LST KCA DVAKNLSATG IFYIDP YLC---FE INPTPMDM GII F VEDSK------TLLKY NSSIQRDVT KEI
              SUB1_6_neu (396) --NIGSKI HQIRSTGFAA AVLITDKLL----EE QTIKFQFF VAFI GSKHR------ETIESY ASSNKNNAT A LE
                Consensus (481) S  I   AL           AA V    D Y G       E     P  I S                            Y SS   T  K 561                                                                                                      640
Wheat ortholog of RNR9  (506) FNA ILNG-------MGVIGY KDPPVWQF SEDVGNLLLTVHFTYSD TIW WT GY ALHMQ KDEGSQ FSG I----ISG
              SUB1_8_neu (538) VSFGAVAAIEGGLNANFSNRA F MYYSARG DPEDNSFNDADVL KPNLVA GNS IWGA W SASTDSTEF E EK----GAM
              SUB1_6_neu (460) FRK IVIG------TKFA E GTYSS RG F----TSFPQI LKPD ILA GTI L IS WPS VEQITGTRALPLFSGFNL
                Consensus (561) F  T                 AP  V   YS RGP            LKPD  APGT IL AW  SV         FG       F 641                                                                                                      720
Wheat ortholog of RNR9  (573) NVTLIKIYSFATEGESSPRSSTCVLYLKVRVQTPVRSRRIL WDQFHN KYPSG VPRD SLNVNNDIL WHGD LH N FHI
              SUB1_8_neu (615) MSGI MAA HVA VAALIKQSY FQFTPSTI SSAL STTAL NDN KGSP MAQRTY SNPD QSLYTATP SD MGS GF  NATAAL
              SUB1_6_neu (525) LTGT MAA HVA VAALIKQ VHPNWSPSAI K SAIMTTAL TLDN---------------I  Y  D       PLAV GA GH ST NKVL
                Consensus (641) GTSMAAPHVAGVAGVAALIKQ  P   PS I  SA   TTAL LDN               I    Y   D         PLD  G GHV TN  L 721                                                                                                      800
Wheat ortholog of RNR9  (653) LFNMLRIAGYVETLGSPLTCFDASNYGTLLMVDLEDEYFSEEIQKLRDDVVHKG LAVFAEWYHVD TMVKMTFFDENT
              SUB1_8_neu (695) DPG VF E T SFEDYI SFLC GINGSDTVVF NYTGFRCPANNTPVSGF------DLNL PSITV STLSGTF QRSMRN IAGN
              SUB1_6_neu (583) NPG II NTPQD FIN T CHEFAKQSRKLI II TRSNISDACKKPSP------YLNYPSIIAYFT SDQSPKIEKR TLT VGEA
                Consensus (721) PGL  DT    D  I   FLC                  N                          L         S   TF R      N 801                                                                                                      880
Wheat ortholog of RNR9  (733) RSWW SPLT GANIPA NELLAS FGIAF GDK ILSGDFSINGE QSHYASGTDIVQFPAGGF LH FELQF D PKT QNSSTPDT
              SUB1_8_neu (768) E---T NVG WSPPY GVSMKV SF TQFSIAMGENQYLSVTLIVTKN----------SSSSSF RIGLFGNTGHIVNIPVT V
              SUB1_6_neu (659) K--RSY IV RVRGLK LNV VEFKKLMF SEK NEKLSYTVRLE SPR--------GLQENVV Y LVSWV DEDA EFEVSCSV
                Consensus (801)     SY  VG            GLN    V P       F  K        E                               G     D A             V 881                                                                                                      960
Wheat ortholog of RNR9  (813) QNSQSQEK SKLSSILGMLEAGEGRIAVYGDSNCLDSSHMVTNCYWLLRKIVEFAGNGLRDPVLFSEATRLKFPVFENIQK
              SUB1_8_neu (834) IN KIASS--
              SUB1_6_neu (728) VA TSLVQES
                Consensus (881) A          S
```

Figure 16 of 18 (Continued)

```
                            961                                                                        1041
Wheat ortholog of RNR9 (Subtilase)  (893) PLRRPDVNFSMFSSVIGKELICHQDSRFEVWGTKGYGIQLTGTTRKLPEYQKNEVSSSPNRLIKSSYKRQDEAGLQKSI
                       SUB1_8_neu   (841) --------------------------------------------------------------------------------
                       SUB1_6_neu   (737) --------------------------------------------------------------------------------
                        Consensus   (961) --------------------------------------------------------------------------------

1041                                                           1106
Wheat ortholog of RNR9 (Subtilase)  (973) APSANKFDDNRDYFGFISHEEVASQWMVPACFAVTTCILVYLSCRAQQRRRRPRKGSATGRLSSSV
                       SUB1_8_neu   (841) -----------------------------------------------------------------
                       SUB1_6_neu   (737) -----------------------------------------------------------------
                        Consensus  (1041) -----------------------------------------------------------------
```

Sequence alignment from wheat RNR9 protein sequence with polypeptides from Arabidopsis thaliana.
Color code (see page 62 of the description):

(a) red against yellow background:          all positions identical (therefore also identical to the consensus) (e.g. position 64 Wheat ortholog of RNR9 (Subtilase))
(b) dark blue against light blue background: this position in this sequence is identical to the consensus (e.g. position 63 Wheat ortholog of RNR9 (Subtilase))
(e) black against white background:          this position in this sequence differs from the consensus (e.g. position 1 Wheat ortholog of RNR9 (Subtilase))

Increasing the host resistance by subtilisin RNR9 RNAi

| Vector | Function | Screen 1 | Screen

Figure 17 of 18 (Continued)

Increase in the mildew resistance of barley by RNAi from subtilisin RNR9 gene in 5 independent experiments. Barley leaf segments were bombarded with an RNAi construct against subtilisin RNR9, the leaf segments were inoculated with barley mildew of the isolate Bgh-A6 and the frequency of fungal haustoria in transformed epidermal cells was determined in relation to the vector control ("relative HAU formation"). An RNAi against subtilisin RNR9 reduced the number of penetrated epidermal cells by more than 45%. SNAP34 RNAi has been employed as a positive control. Its RNAi has been shown to increase the host resistance to Bgh-A6.

Carrying out the transient single-cell RNAi analysis

USE OF SUBTILISIN-LIKE RNR9 POLYNUCLEOTIDE FOR ACHIEVING PATHOGEN RESISTANCE IN PLANTS

RELATED APPLICATIONS

This application is a national stage application (under 35 U.S.C. §371) of PCT/EP2008/050402, filed Jan. 15, 2008, which claims benefit of European application 07100564.9, filed Jan. 15, 2007.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Revised_Sequence_List__13987__00105_US. The size of the text file is 82 KB, and the text file was created on Feb. 1, 2010.

FIELD OF THE INVENTION

The invention relates to a method of generating or increasing a pathogen resistance in plants by reducing the expression of at least one subtilisin polypeptide or a functional equivalent thereof. The invention relates to novel nucleic acid sequences coding for a *Hordeum vulgare* subtilisin (HvRNR9, see FIG. 3) and *Triticum aestivum* subtilisin (TaRNR9, see FIG. 1) polynucleotide and describes homologous sequences (RNR9) thereof, and to their use in methods for obtaining a pathogen resistance in plants, and to nucleic acid constructs, expression cassettes and vectors which comprise these sequences and which are suitable for mediating a fungal resistance in plants. The invention furthermore relates to transgenic organisms, in particular plants, which are transformed with these expression cassettes or vectors, and to cultures, parts or transgenic propagation material derived therefrom.

BACKGROUND OF THE INVENTION

There are only few approaches, which confer a resistance to pathogens, mainly fungal pathogens, to plants. This shortcoming can partly be attributed to the complexity of the biological systems in question. Another fact which stands in the way of obtaining resistances to pathogens is that little is known about the interactions between pathogen and plant. The large number of different pathogens, the infection mechanisms developed by these organisms and the defence mechanisms developed by the plant phyla, families and species interact with one another in many different ways.

Fungal pathogens have developed essentially two infection strategies. Some fungi enter into the host tissue via the stomata (for example rusts, *Septoria* species, *Fusarium* species) and penetrate the mesophyll tissue, while others penetrate via the cuticles into the epidermal cells underneath (for example *Blumeria* species).

The infections caused by the fungal pathogens lead to the activation of the plant's defence mechanisms in the infected plants. Thus, it has been possible to demonstrate that defence reactions against epidermis-penetrating fungi frequently start with the formation of a penetration resistance (formation of papillae, strengthening of the cell wall with callose as the main constituent) underneath the fungal penetration hypha (Elliott et al. Mol Plant Microbe Interact. 15: 1069-77; 2002).

In some cases, however, the plant's defence mechanisms only confer an insufficient protection mechanism against the attack by pathogens.

The formation of a penetration resistance to pathogens whose infection mechanism comprises a penetration of the epidermal cells or of the mesophyll cells is of great importance both for monocotyledonous and for dicotyledonous plants. In contrast to the described mlo-mediated resistance, it can probably make possible the development of a broad-spectrum resistance against obligatory biotrophic, hemibiotrophic and necrotrophic fungi.

The present invention was therefore based on the object of providing a method for generating a resistance of plants to penetrating pathogens.

The object is achieved by the embodiments characterized in the claims.

SUMMARY OF THE INVENTION

The invention therefore relates to a method of increasing the resistance to penetrating pathogens in a monocotyledonous or dicotyledonous plant, or a part of a plant, for example in an organ, tissue, a cell or a part of a plant cell, for example in an organelle, which comprises lessening or reducing the activity or amount of a subtilisin protein (RNR9) in the plant, or a part of the plant, for example in an organ, tissue, a cell or a part of a cell, for example in a cell compartment, for example in an organelle, in comparison with a control plant or a part of a control plant, for example its organ, tissue, cell or part of a cell, for example in a cell compartment, for example in an organelle.

Preferably, a race-unspecific resistance is obtained in the method according to the invention. Thus, for example, a broad-spectrum resistance against obligatorily biotrophic and/or hembiotrophic and/or necrotrophic fungi of plants, in particular against mesophyll-penetrating pathogens, can be obtained by the method according to the invention.

Surprisingly, it has been observed that the gene silencing via dsRNAi of a gene which codes for the subtilisin protein HvRNR9 results in an increase in the resistance of monocotyledonous and dicotyledonous plants to fungal pathogens. Thus, this negative control function in the event of attack by fungal pathogens has been demonstrated for the subtilisin protein HvRNR9 from barley (*Hordeum vulgare*) (HvRNR9), wheat (*Triticum aestivum*) and thale cress (*Arabidopsis thaliana*).

It has been found within the scope of a TIGS (=Transient Induced Gene Silencing) analysis in barley by the method of Schweizer et al. (2001) that a dsRNAi-mediated silencing of the gene HvRNR9 greatly increases the resistance to *Blumeria graminis* f. sp. *hordei* (synonym: *Erysiphe graminis* DC. f. sp. *hordei*). This effect has also been obtained in dicotyledonous species such as, for example, *Arabidopsis thaliana* by inducing the post-transcriptional gene silencing (PTGS). This emphasizes the universal importance of the loss-of-function of HvRNR9-homologous genes for the development of a broad-spectrum pathogen resistance of the plant.

BRIEF DESCRIPTION OF THE FIGURES

FIG. 1 shows the nucleic acid sequence of subtilisin RNR9 from *Triticum aestivum* (wheat); TaRNR9 (SEQ ID NO: 1).

FIG. 2 shows the protein sequence of subtilisin RNR9 from *Triticum aestivum* (wheat); TaRNR9 (SEQ ID NO: 2).

FIG. 3 shows the nucleic acid sequence of subtilisin RNR9 from *Hordeum vulgare* (barley); HvRNR9 (SEQ ID NO: 3).

FIG. 4 shows the protein sequence of subtilisin RNR9 from *Hordeum vulgare* (barley); HvRNR9 (SEQ ID NO: 4).

FIG. 5 shows the nucleic acid sequence of SUB1_6_neu from *Arabidopsis thaliana* (SEQ ID NO: 5).

FIG. 6 shows the protein sequence of SUB1_6_neu from *Arabidopsis thaliana* (SEQ ID NO: 6).

FIG. 7 shows the nucleic acid sequence of SUB 1_8_neu from *Arabidopsis thaliana* (SEQ ID NO: 7).

FIG. 8 shows the protein sequence of SUB 1_8_neu from *Arabidopsis thaliana* (SEQ ID NO: 8).

FIG. 9 shows the nucleic acid sequence of SUB RNR9 from *Zea mays* (maize); ZmSubtilisin RNR9 (SEQ ID NO: 9).

FIG. 10 shows the protein sequence of SUB RNR9 from *Zea mays* (maize); ZmSubtilisin RNR9 (SEQ ID NO: 10).

FIG. 11 shows the nucleic acid sequence of SUB RNR9 from *Oryza sativa* (rice) (SEQ ID NO: 11).

FIG. 12 shows the protein sequence of SUB RNR9 from *Oryza sativa* (rice) (SEQ ID NO: 12).

FIG. 13 shows the consensus sequence from the sequence alignment as shown in FIG. 16 (SEQ ID NO: 13).

FIG. 14 shows the consensus sequence 2 from the sequence alignment as shown in FIG. 16 (SEQ ID NO: 14).

FIG. 15 shows the primer sequences as given on page 68 (in 5'-3"-direction). The sequences shown are Upper Primer (SEQ ID NO: 15) and Lower Primer (SEQ ID NO: 16).

FIG. 16 shows a sequence alignment from wheat RNR9 protein sequence with polypeptides from *Arabidopsis thaliana*. The sequences shown are: wheat ortholog of RNR9 (Subtilase) (SEQ ID NO: 1); SUB1_8_neu (SEQ ID NO: 8); and SUB1_6_neu (SEQ ID NO: 6). Color code (see page 62 of the description): (a) red against yellow background (boxed text): all positions identical; (b) dark blue against light blue background (white text against black background): this position in this sequence is identical to the consensus; (c) black against white background: this position in this sequence differs from the consensus.

DETAILED DESCRIPTION OF THE INVENTION

Figure 17:
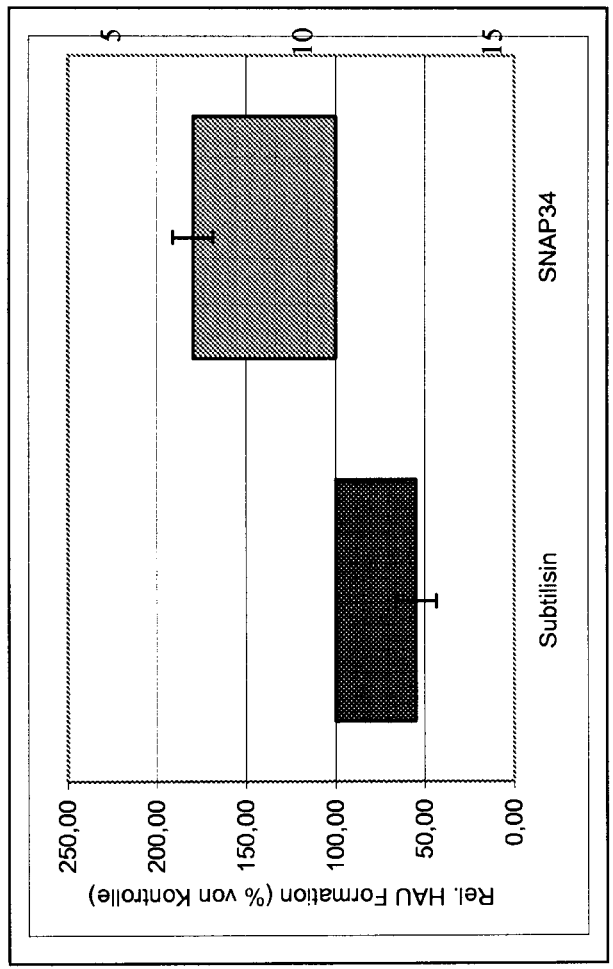
FIG. 17 shows the increase in the mildew resistance of barley by RNAi from subtilisin RNR9 gene in 5 independent experiments.
Figure 18:
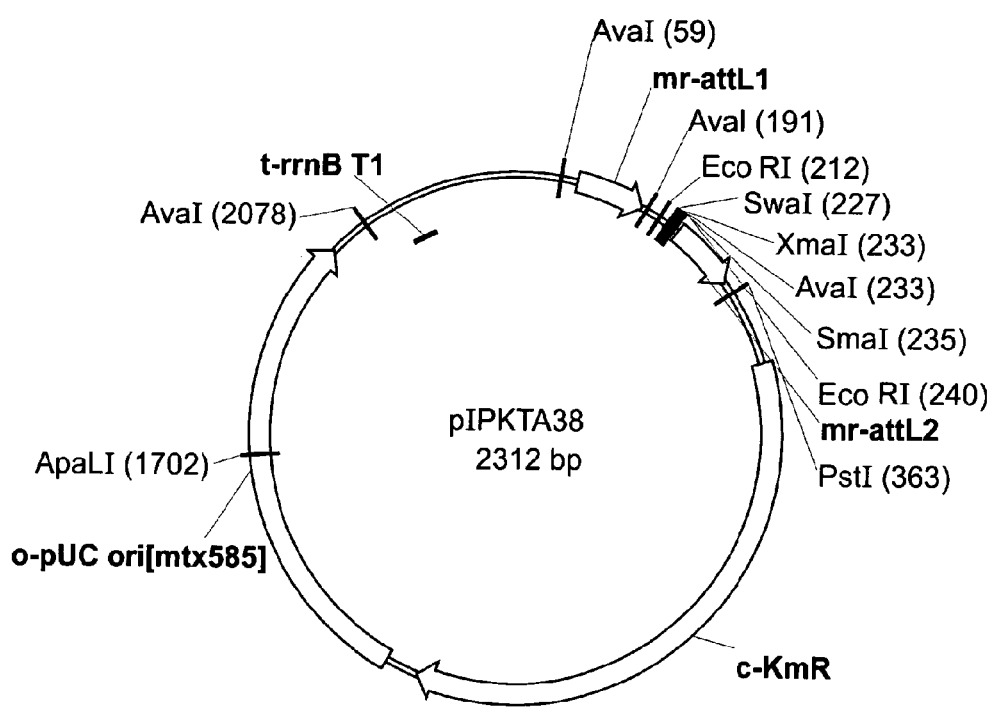
FIG. 18 shows the vector map for pIPKTA38.

Ser proteinases are of extremely widespread occurrence. One of the largest families of this type of enzymes is that represented by the subtilisin-like (subtilase) family (EC 3.4.21.14). This family represents an ancient family of proteins with homologs in such diverse organisms as Archae, bacteria, fungi, yeast, and higher eukaryotes including plants. The subtilisin-like Ser proteases are distinguished by the characteristic arrangement of the catalytic His, Asp, and Ser residues that conform the catalytic triad (Siezen and Leunissen (1997) Protein Sci 6: 501-523). This active site signature has been used to classify these enzymes into five families: subtilisin, thermitase, kexin, pyrolysin, proteinase K, and lantibiotic peptidases (Siezen and Leunissen (1997) Protein Sci 6: 501-523). Although more than 200 subtilisin-like enzymes are presently known, our information on the existence and role of this type of protease in plants is still scant. So far, subtilisinlike proteases have been identified and the genes cloned in only a few plant species, including *Arabidopsis* (Ribeiro et al. (1995) Plant Cell 7: 785-794), cucumber (*Cucumis sativus*) (Yamagata et al. (1994) J Biol Chem 269: 32725-32731), *Alnus glutinosa* (Ribeiro et al. (1995) Plant Cell 7: 785-794), and tomato (*Lycopersicon esculentum*) (Riggs and Horsch (1995) Plant Physiol 108: 117).

The plant proteinases can be grouped within the pyrolysin family (Siezen and Leunissen (1997) Protein Sci 6: 501-523). In tomato, recent sequence comparison revealed that the subtilase genes fall into five distinct subfamilies (Meichtry et al. (1999) Plant Mol Biol 39: 749-760), with the P69 subfamily members the best characterized so far. The P69 subtilisin-like proteases are represented by different protein isoforms of approximately 69 kD (P69). The P69 family is represented by 4 genes in *Arabidopsis*. In contrast to the expression pattern of P69A and P69D, the P69B and P69C genes do not appear to be constitutively expressed at any stage of normal plant development. Instead, they are coordinately and systemically induced de novo by salicylic acid treatment or following infection with the pathogen *Pseudomonas syringae* (Jorda et al. (1999) J Biol Chem 274: 2360-2365). This mechanism of gene regulation suggests that both, P69B and P69C, may play roles as active defense weapons against the attacking pathogen. As it has been shown for other PR genes such as PR-1, PR-2, and PR-3, these expression patterns could imply an increased pathogen resistance by overexpression of a subtilase gene.

The finding that a reduction in the expression of subtilisin leads to a significant increase in the pathogen resistance in plants was all the more surprising.

In a further embodiment, the invention therefore relates to a method of generating a plant with an increased resistance to plant pathogens, preferably with a broad-spectrum resistance, in particular to fungal pathogens, for example from the classes Ascomycetes, Basidiomycetes, Chytridiomycetes or Oomycetes, for example of mildews of the family Erysiphaceae, genus *Blumeria*, by interfering with the cell wall structure, in particular by reducing the membrane permeability, for example for singly charged cations, in particular by modifying the ion concentration in the cell, preferably by increasing the concentration of singly charged cations, such as, for example, sodium, for example by mutation of an ion channel or of a protein which interacts with, or regulates, an ion channel.

In an embodiment, the invention therefore relates to a method of generating a plant with an increased resistance to plant pathogens, preferably with a broad-spectrum resistance, in particular to fungal pathogens, for example from the classes Ascomycetes, Basidiomycetes, Chytridiomycetes or Oomycetes, for example of mildews of the family Erysiphaceae, genus *Blumeria*, by reducing the expression or by mutation of a subtilisin RNR9 protein.

In a further embodiment, the activity of a subtilisin-like polypeptide is reduced, for example blocked or eliminated, in the method according to the invention.

In a further embodiment, in the method according to the invention the activity of a polypeptide is reduced or eliminated, which is encoded by a polynucleotide comprising at least one nucleic acid molecule selected from the group consisting of:

(a) nucleic acid molecule which codes for at least one polypeptide comprising the sequences as shown in FIG. 2, 4, 6, 8, 10, 12, 13 or 14;

(b) nucleic acid molecule which comprises at least one polynucleotide of the sequences as shown in FIG. 1, 3, 5, 7, 9 or 11;

(c) nucleic acid molecule which codes for a polypeptide whose sequence has at least 35%, 40%, 45%, 50%, 55% or 60%, 70%, 75%, 80%, 85%, 90%, 95%, 97%, 98% or 99% identity to the sequence as shown in FIG. 2, 4, 6, 8, 10, 12, 13 or 14;

(d) nucleic acid molecule according to (a) to (c) which codes for a functional fragment or an epitope of the sequences as shown in FIG. 1, 3, 5, 7, 9 or 11;
(e) nucleic acid molecule which codes for a polypeptide which is recognized by a monoclonal antibody directed against a polypeptide which is encoded by the nucleic acid molecules as shown in (a) to (c);
(f) nucleic acid molecule which hybridizes under stringent conditions with a nucleic acid molecule as shown in (a) to (c); and
(g) nucleic acid molecule which can be isolated from a DNA library using a nucleic acid molecule as shown in (a) to (c) or their fragments of at least 15 nt, preferably 20 nt, 30 nt, 50 nt, 100 nt, 200 nt, 500 nt, 750 nt, 1000 nt, 1250 nt, 1500 nt, 1750 nt or 2000 nt, as probe under stringent hybridization conditions;
or the complementary sequence thereof.

In the method according to the invention, it is in particular the resistance to mesophyll-cell-penetrating pathogens, which is preferably increased.

In one embodiment, the resistance is obtained by lessening, reducing or blocking the expression of a polypeptide, preferably of a polypeptide which is encoded by the above-described nucleic acid molecule, for example that of a subtilisin RNR9 from barley as shown herein in FIG. 3, or from wheat as shown herein in FIG. 1 or from *Arabidopsis thaliana* as shown herein in FIG. 5 or 7 or from *Zea mays* as shown herein in FIG. 9 or from or from *Oryza sativa* as shown herein in FIG. 11 or from
SUB1_6_neu (*Arabidopsis thaliana*)=SUB1_5_neu
LOCUS NP_569044 736 aa linear PLN 9 Jun. 2006
DEFINITION peptidase/subtilase [*Arabidopsis thaliana*].
ACCESSION NP_569044
VERSION NP_569044.1 GI:18425150
DBSOURCE REFSEQ: accession NM_126109.1
or,
SUB1_8 neu (*Arabidopsis thaliana*)
LOCUS NP_568634 840 aa linear PLN 9 Jun. 2006
DEFINITION peptidase/subtilase [*Arabidopsis thaliana*].
ACCESSION NP_568634
VERSION NP_568634.1 GI:18422451
DBSOURCE REFSEQ: accession NM_123820.1

On the other hand, it is also possible to reduce, lessen or block the endogenous activity of one of these polypeptides by methods known to the skilled worker, for example by mutating a genomically coding region for the active center, for binding sites, for localization signals, for domains, clusters and the like, such as, for example, of coding regions for coiled coil, HEAT, FBOX, LRR, IBIB, C2, WD40, beach, U-box or UND domains. The activity can be reduced in accordance with the invention by mutations, which affect the secondary, tertiary or quaternary structure of the protein.

Mutations can be inserted for example by an EMS mutagenesis. Domains can be identified by suitable computer programs such as, for example, SMART or InterPRO, for example as described in P. Andersen (The Journal of Biol. Chemistry, 279, 38, pp. 40053-40061, 2004) or Y. Mudgil (Plant Physiology, 134, 59-66, 2004) and literature cited therein. The suitable mutants can then be identified for example by tilling.

In one embodiment, the lessening of the polypeptide quantity, activity or function of a subtilisin RNR9 protein in a plant is combined with increasing the polypeptide quantity, activity or function of other resistance factors, preferably of a Bax inhibitor 1 protein (BI-1), preferably of the Bax inhibitor 1 protein from *Hordeum vulgare* (GENBANK® Accession No.: AJ290421), from *Nicotiana tabacum* (GENBANK® Accession No.: AF390556), rice (GENBANK® Accession No.: AB025926), *Arabidopsis* (GENBANK® Accession No.: AB025927) or tobacco and oilseed rape GENBANK® Accession No.: AF390555, Bolduc N et al. (2003) Planta 216:377-386) or of ROR2 (for example from barley (GENBANK® Accession No.: AY246906)), SNAP34 (for example from barley (GENBANK® Accession No.: AY247208)) and/or of the lumenal binding protein BiP for example from rice (GENBANK® Accession No.: AF006825). An increase can be achieved for example by mutagenesis or overexpression of a transgene, inter alia.

In one embodiment, the lowering of the polypeptide quantity, activity or function of a subtilisin RNR9 protein in a plant is combined with decreasing the protein quantity, activity or function of other resistance factors, preferably of the proteins RacB (for example from barley (GENBANK® Accession No.: AJ344223), CSL1 (for example from *Arabidopsis* (GENBANK® Accession No.: NM116593)), HvNaOX (for example from barley (GENBANK® Accession No.: AJ251717)), MLO (for example from barley (GENBANK® Accession No.: Z83834)), ARM1 (armadillo repeat protein; application number 05110468.5).

The activity or function of MLO, BI-1 and/or NaOX can be reduced or inhibited analogously to what has been described for MLO in WO 98/04586; WO 00/01722; WO 99/47552 and the further publications mentioned hereinbelow, whose content is herewith expressly incorporated by reference, in particular in order to describe the activity and inhibition of MLO. The description of the abovementioned publications describes processes, methods and especially preferred embodiments for lessening or inhibiting the activity or function of MLO; the examples indicate specifically how this can be realized.

The reduction of the activity or function, if appropriate of the expression of BI-1 is described in detail in WO 2003020939, which is herewith expressly incorporated into the present description. The description of the abovementioned publication describes processes and methods for lessening or inhibiting the activity or function of BI-1; the examples indicate specifically how this can be realized. The reduction or inhibition of the activity or function of BI-1 is especially preferably carried out in accordance with the embodiments especially preferred in WO 2003020939 and the examples and in the organisms shown therein as being especially preferred, in particular in a plant, for example constitutively, or a part thereof, for example in a tissue, but especially advantageously at least in the epidermis or in a considerable part of the epidermal cells. The reduction of the activity or function, if appropriate of the expression, of BI-1 is described extensively in WO 2003020939. The skilled worker finds in WO 2003020939 the sequences which code for BI-1 proteins and can also identify BI-1 with the method provided in WO 2003020939.

The reduction of the activity or function, if appropriate of the expression, of NaOX is described extensively in PCT/EP/03/07589, which is herewith expressly incorporated into the present description. The description of the abovementioned publication describes processes and methods for lessening or inhibiting the activity or function of NaOX, and the examples indicate specifically how this can be realized. The reduction or inhibition of the activity or function of NaOX is especially preferably carried out in accordance with the embodiments especially preferred in PCT/EP/03/07589 and the examples and in the organisms shown therein as being especially preferred, in particular in a plant, for example constitutively, or a part thereof, for example in a tissue, but especially advantageously at least in the epidermis or in a considerable part of the epidermal cells. The skilled worker finds in PCT/EP/03/07589 the sequences, which code for NaOX proteins and can also identify NaOX with the method provided in PCT/EP/03/07589.

The terms "to lessen", "to reduce" or "to repress" or their substantives are used synonymously in the present text.

"Lessening", "reduction" or "repression" or their verbs are understood as meaning, in accordance with the invention, that the activity in the plant is lower than in a control plant or is lower in a part of a plant than in the same part of a control plant, for example in an organ, an organelle, a tissue or a cell. In one embodiment, the activity of the abovementioned polypeptide is 10%, 20%, 30%, 40%, 50%, 60%, 70%, 75%, 80%, 85%, 90%, 93%, 95%, 96%, 97%, 98%, 99% or more lower than in the control. In one embodiment, no expression of the abovementioned polypeptide takes place. As a consequence, these terms also comprise the complete inhibition or blocking of an activity, for example by the knock-out of a gene or the use of RNAi.

"Reduction", "to reduce", "lessening" or "to lessen", "repression" or "to repress" comprise the partial or essentially complete inhibition or blocking of the functionality of a protein, based on a variety of cell-biological mechanisms.

Lessening within the purpose of the invention also comprises a quantitative reducing of a protein down to an essentially complete absence of the protein (i.e. lack of detectability of activity or function or lack of immunological detectability of the protein). Here, the expression of a certain protein or the activity or function in a cell or an organism is reduced by preferably more than 50%, 60%, 70%, especially preferably by more than 80%, 85%, very especially preferably by more than 90%, 95%.

For example, the expression of a nucleic acid molecule for a subtilisin RNR9 protein, for example in combination with a tissue-specific increase in the activity of a Bax inhibitor-1 protein may take place in the mesophyll tissue. The reduction of the subtilisin RNR9 protein quantity in a transgenic plant which for example overexpresses BI-1 in the mesophyll tissue offers the possibility of generating a complete and comprehensive fungal resistance in the plant.

In a further embodiment, the increase in the polypeptide quantity, activity or function of a Bax Inhibitor 1 protein from *Hordeum vulgare* (GENBANK® Accession No.: AJ290421), from *Nicotiana tabacum* (GENBANK® Accession No.: AF390556), rice (GENBANK® Accession No.: AB025926), *Arabidopsis* (GENBANK® Accession No.: AB025927) or tobacco and oilseed rape (GENBANK® Accession No.: AF390555, Bolduc N et al. (2003) Planta 216:377-386) or of ROR2 (for example from barley (GENBANK® Accession No.: AY246906), SnAP34 (for example from barley (GENBANK® Accession No.: AY247208) and/or of the lumenal binding protein BiP for example from rice (GENBANK® Accession No.: AF006825) is effected in combination with the reduction in the protein quantity or activity or function of the proteins RacB (for example from barley (GENBANK® Accession No.: AJ344223), CSL1 (for example from *Arabidopsis* (GENBANK® Accession No.: NM116593)), HvNaOX (for example from barley (GENBANK® Accession No.: AJ251717)), and/or MLO (for example from barley (GENBANK® Accession No.: Z83834)). As a consequence, in one embodiment, at least one of the abovementioned genes which are suitable for overexpression or increased activity is activated or overexpressed and/or at least one of the abovementioned genes which is suitable for reduction is reduced.

An increase in the expression can be obtained as described herein. An increase in the expression or function is understood as meaning herein both the activation or enhancement of the expression or function of the endogenous protein, including a de novo expression, and an increase or enhancement by expression of a transgenic protein or factor.

For the purposes of the invention, "organism" means "non-human organisms" as long as the term relates to a viable multi-celled organism.

For the purposes of the invention, "plants" means all dicotyledonous or monocotyledonous plants. Preferred are plants which can be subsumed under the class of the Liliatae (Monocotyledoneae or monocotyledonous plants). The term includes the mature plants, seeds, shoots and seedlings, and parts, propagation material, plant organs, tissue, protoplasts, callus and other cultures, for example cell cultures derived from the above, and all other types of associations of plant cells which give functional or structural units. Mature plants means plants at any developmental stage beyond the seedling stage. Seedling means a young, immature plant in an early developmental stage.

"Plant" also comprises annual and perennial dicotyledonous or monocotyledonous plants and includes by way of example, but not by limitation, those of the genera *Bromus, Asparagus, Pennisetum, Lolium, Oryza, Zea, Avena, Hordeum, Secale, Triticum, Sorghum* and *Saccharum*.

In a preferred embodiment, the method according to the invention is applied to monocotyledonous plants, for example from the family Poaceae, especially preferably to the genera *Oryza, Zea, Avena, Hordeum, Secale, Triticum, Sorghum* and *Saccharum*, very especially preferably to agriculturally important plants such as, for example, *Hordeum vulgare* (barley), *Triticum aestivum* (wheat), *Triticum aestivum* subsp. *spelta* (spelt), Triticale, *Avena sativa* (oats), *Secale cereale* (rye), *Sorghum bicolor* (sorghum), *Zea mays* (maize), *Saccharum officinarum* (sugar cane) or *Oryza sativa* (rice). Thus, in a preferred embodiment, the expression or activity of the subtilisin RNR9 protein or polynucleotide is reduced in one of these plants.

"Epidermal tissue" or epidermis means the external tissue layers of the plants. It can be single layered or multiple layered; and there is epidermis-"enriched" gene expression, such as, for example, Cer3, which can act as marker, exists; Hannoufa, A. (1996) Plant J. 10 (3), 459-467.

By "epidermis", the skilled worker preferably means the predominant dermal tissue of primary aerial plant parts, such as of the shoots, the leaves, flowers, fruits and seeds. The epidermal cells excrete a water-repellent layer, the cuticle, towards the outside. The roots are surrounded by the rhizodermis, which resembles the epidermis in many ways, but also differs substantially therefrom. The epidermis develops from the outermost layer of the apical meristem. The origin of the rhizodermis, in contrast, is less clear. Phylogenetically speaking, it can be assigned either to the calyptra or to the primary bark, depending on the species. A large number of functions can be ascribed to the epidermis: it protects the plant from dehydration and regulates the transpiration rate. It protects the plant from a wide range of chemical and physical external factors and against feeding animals and attack by parasites. It is involved in the gas exchange, in the secretion of certain metabolites and in the absorption of water. It contains receptors for light and mechanical stimuli. It therefore acts as signal transformer between the environment and the plant. In accordance with the various functions, the epidermis comprises a number of differently differentiated cells. Other aspects are species having specific variants and different organization of the epidermides in the individual parts of a plant. Essentially, it consists of three categories of cells: the "actual" epidermal cells, the cells of the stomata and of the trichomes (Greek: trichoma, hair), which are epidermal appendages with different shapes, structures and functions.

The "actual", i.e. the least specialized epidermal cells, account for most of the bulk of the cells of the epidermal tissue. In topview, they appear either polygonal (slab or plate shaped) or elongated. The walls between them are often wavy or sinuate. It is not known what induces this shape during development; existing hypotheses only offer unsatisfactory explanations herefor. Elongated epidermal cells can be found in organs or parts of organs that are elongated themselves, thus, for example, in stems, petioles, leaf veins and on the leaves of most monocots. The upper surface and undersurface of laminae can be covered in epidermides with different structures, it being possible for the shape of the cells, the wall thickness and the distribution and number of specialized cells (stomata and/or trichomes) per unit area to vary. A high degree of variation is also found within individual families, for example in the Crassulaceae. In most cases, the epidermis consists of a single layer, though multi-layered water-storing epidermides have been found among species from a plurality of families (Moraceae: most *Ficus* species; Piperaceae: *Peperonia*, Begoniaceae, Malvaceae and the like). Epidermal cells secrete a cuticle to the outside which covers all epidermal surfaces as an uninterrupted film. It may either be smooth or structured by bulges, rods, folds and furrows. However, the folding of the cuticle, which can be observed when viewing the surface, is not always caused by the formation of cuticular rods. Indeed, there are cases where cuticular folding is merely the expression of the underlying bulges of the cell wall. Epidermal appendages of various form, structure and function are referred to as trichomes and, in the present context, likewise come under the term "epidermis". They occur in the form of protective hairs, supportive hairs and gland hairs in the form of scales, different papillae and, in the case of roots, as absorbent hairs. They are formed exclusively by epidermal cells. Frequently, a trichome is formed by only one such cell, however, occasionally, more than one cell is involved in its formation.

The term "epidermis" likewise comprises papillae. Papillae are bulges of the epidermal surface. The textbook example thereof is the papillae on flower surfaces of the pansy (*Viola tricolor*) and the leaf surfaces of many species from tropical rain forests. They impart a velvet-like consistency to the surface. Some epidermal cells can form water stores. A typical example is the water vesicles at the surfaces of many *Mesembryanthemum* species and other succulents. In some plants, for example in the case of campanula (*Campanula persicifolia*), the outer walls of the epidermis are thickened like a lens.

The main biomass of all tissues is the parenchyma. The parenchymatic tissues include the mesophyll which, in leaves, can be differentiated into palisade parenchyma and spongy parenchyma. Accordingly the skilled worker understands, by mesophyll, a parenchymatic tissue. Parenchymatic cells are always alive, in most cases isodiametric, rarely elongated. The pith of the shoots, the storage tissues of the fruits, seeds, the root and other underground organs are also to be considered as parenchymas, as is the mesophyll. "Mesophyll tissue" means the foliar tissue between the epidermal layers, and consists of pallisade tissue, spongy tissue and the vascular bundles of the leaf.

In the leaves of most ferns and phanerogams, especially in the case of the dicots and many monocots, the mesophyll is subdivided into palisade parenchymas and spongy parenchymas. A "typical" leaf is of dorsiventral organization. In most cases, the palisade parenchyma is at the upper surface of the leaf immediately underneath the epidermis. The spongy parenchyma fills the underlying space. It is interspersed by a voluminous intercellular system whose gas space is in direct contact with the external space via the stomata.

The palisade parenchyma consists of elongated cylindrical cells. In some species, the cells are irregular, occasionally bifurcate (Y-shaped: arm palisade parenchyma). Such variants are found in ferns, conifers and a few angiosperms (for example in some Ranunculaceae and Caprifoliaceae species (example: elder)). Besides the widest-spread organization form which has just been described, the following variants have been found:

Palisade parenchyma at the leaf undersurface. Particularly conspicuously in scaly leaves. (For example *arbor vitae* (thuja), and in the leaves of wild garlic (*Allium ursinum*)).

Palisade parenchyma at both leaf surfaces (upper surface and undersurface). Frequently found in plants of dry habitats (xerophytes). Example: prickly lettuce (*Lactuca serriola*);

Ring-shaped closed palisade parenchyma: in cylindrically organized leaves and in needles from conifers.

The variability of the cells of the spongy parenchyma, and the organization of the spongy parenchyma itself, are even more varied than that of the palisade parenchyma. It is most frequently referred to as aerenchyma since it comprises a multiplicity of interconnected intercellular spaces.

The mesophyll may comprise what is known as the assimilation tissue, but the terms mesophyll and assimilation tissue are not to be used synonymously. There are chloroplast-free leaves whose organization differs only to a minor extent from comparable green leaves. As a consequence, they comprise mesophyll, but assimilation does not take place; conversely, assimilation also takes place in, for example, sections of the shoot. Further aids for characterizing epidermis and mesophyll can be found by the skilled worker for example in: v. Guttenberg, H.: Lehrbuch der Allgemeinen Botanik [Textbook of general botany]. Berlin: Akademie-Verlag 1955 (5th Ed.), Haberlandt, G.: Physiologische Pflanzenanatomie [Physiological plant anatomy]. Leipzig: W. Engelmann 1924 (6th Ed.); Troll, W.: Morphologie der Pflanzen [Plant morphology]. Volume 1: Vegetationsorgane [Vegetation organs]. Berlin: Gebr. Borntraeger, 1937; Troll, W.: Praktische Einführung in die Pflanzenmorphologie [Practical introduction to plant morphology]. Jena: VEB G. Thieme Verlag 1954/1957; Troll, W., Höhn, K.: Allgemeine Botanik [General botany]. Stuttgart: F. Enke Verlag, 1973 (4th Ed.)

As a consequence, epidermis or epidermal cells can be characterized in histological or biochemical, including molecular-biochemical, terms. In one embodiment, the epidermis is characterized in biochemical terms. In one embodiment, the epidermis can be characterized by the activity of one or more of the following promoters:

(1) WIR5 (=GstA1), acc. X56012, Dudler & Schweizer, unpublished.

(2) GLP4, acc. AJ310534; Wei, Y. (1998); Plant Molecular Biology 36, 101-112.

(3) GLP2a, acc. AJ237942, Schweizer, P. (1999); Plant J 20, 541-552.

(4) Prx7, acc. AJ003141, Kristensen B K (2001); Molecular Plant Pathology, 2(6), 311-317.

(5) GerA, acc. AF250933, Wu S. (2000); Plant Phys Biochem 38, 685-698.

(6) OsROC1, acc. AP004656.

(7) RTBV, acc. AAV62708, AAV62707, Klöti, A. (1999); PMB 40, 249-266.

(8) Cer3; Hannoufa, A. (1996); Plant J. 10 (3), 459-467.

In another embodiment, the epidermis is characterized in that only some of the promoters are active, for example 2, 3, 5 or 7 or more, but at least one of the abovementioned promoters is active. In one embodiment, the epidermis is characterized in that all of the above-mentioned promoters are active in the tissue or the cell.

In one embodiment, the expression or activity of the subtilisin RNR9 protein or polynucleotide in the epidermis is reduced by the expression of an inhibitory molecule under the control of an epidermis-specific promoter, in particular under the control of one of the above-mentioned promoters. Examples of inhibitory molecules are listed hereinbelow, for example RNAi, antisense-RNA, microRNA, cosuppression, antibodies and other methods which are known to the skilled worker. The epidermis-specific expression of an inhibitory molecule in the epidermis is particularly advantageous for increasing the resistance of a plant to mildew.

As a consequence, mesophyll or mesophyll cells can be characterized in biochemical, including molecular-biological, or histological terms. In one embodiment, the mesophyll is characterized in biochemical terms. In one embodiment, the mesophyll can be characterized by the activity of one or more of the following promoters:

(1) PPCZm1 (=PEPC); Kausch, A. P. (2001); Plant Mol. Biol. 45, 1-15.
(2) OsrbcS, Kyozuka et al PlaNT Phys: (1993) 102: Kyozuka J, 1993. Plant Phys 102, 991-1000.
(3) OsPPDK, acc. AC099041.
(4) TaGF-2.8, acc. M63223; Schweizer, P. (1999); Plant J 20, 541-552.
(5) TaFBPase, acc. X53957.
(6) TaWIS1, acc. AF467542; US 200220115849.
(7) HvBIS1, acc. AF467539; US 200220115849.
(8) ZmMIS1, acc. AF467514; US 200220115849.
(9) HvPR1a, acc. X74939; Bryngelsson et al. Molecular Plant-Microbe Interactions (1994).
(10) HvPR1b, acc. X74940; Bryngelsson et al. Molecular Plant-Microbe Interactions (1994).
(11) HvB1,3gluc; acc. AF479647.
(12) HvPrx8, acc. AJ276227; Kristensen et al MPP (2001) (see above).
(13) HvPAL, acc. X97313; Wei, Y. (1998); Plant Molecular Biology 36, 101-112.

In another embodiment, the mesophyll is characterized in that only some of the promoters are active, for example 2, 3, 5 or 7 or more, but at least one of the abovementioned promoters is active. In one embodiment, the mesophyll is characterized in that all the above-mentioned promoters are active in the tissue or the cell.

In one embodiment, all of the abovementioned promoters are active in the epidermis of a plant which is used or generated in accordance with the invention or of a plant according to the invention in the epidermis and in the mesophyll. In one embodiment, only some of the abovementioned promoters are active, for example 2, 5, 7 or more, but at least one of the promoters enumerated above is in each case active.

In one embodiment, the expression or activity of the subtilisin RNR9 protein or polynucleotide in the mesophyll is reduced by the expression of an inhibitory molecule under the control of a mesophyll-specific promoter, in particular under the control of one of the above-mentioned promoters. Examples of inhibitory molecules are listed hereinbelow, for example RNAi, antisense-RNA, microRNA, cosuppression, antibodies and other methods which are known to the skilled worker. The epidermis-specific expression of an inhibitory molecule in the mesophyll is particularly advantageous for increasing the resistance of a plant to *Septoria* and/or rusts.

In one embodiment, the expression or activity of the subtilisin RNR9 protein or polynucleotide in the mesophyll and in the epidermis is reduced by the expression of inhibitory molecules under the control of mesophyll- and/or epidermis-specific promoters, in particular under the control of the abovementioned promoters. Examples of inhibitory molecules are mentioned hereinbelow, for example RNAi, antisense-RNA, antibodies and others.

"Nucleic acids" means biopolymers of nucleotides which are linked with one another via phosphodiester bonds (polynucleotides, polynucleic acids). Depending on the type of sugar in the nucleotides (ribose or desoxyribose), one distinguishes the two classes of the ribonucleic acids (RNA) and the desoxyribonucleic acids (DNA).

The term "crop" means all plant parts obtained by growing plants agriculturally and collected within the harvesting process.

"Resistance" means the preventing, the repressing, the reducing or the weakening of disease symptoms of a plant as the result of infection by a pathogen. The symptoms can be manifold, but preferably comprise those which directly or indirectly lead to an adversely affect on the quality of the plant, on the quantity of the yield, on the suitability for use as feed or foodstuff, or else which make sowing, growing, harvesting or processing of the crop more difficult.

In a preferred embodiment, the following disease symptoms are weakened, reduced or prevented: formation of pustules and hymenia on the surfaces of the affected tissues, maceration of the tissues, spreading necroses of the tissue, accumulation of mycotoxins, for example from *Fusarium graminearum* or *F. culmorum*.

"Conferring", "existing", "generating" or "increasing" a pathogen resistance means that the defence mechanisms of a certain plant or in a part of a plant, for example in an organ, a tissue, a cell or an organelle, have an increased resistance to one or more pathogens as the result of using the method according to the invention in comparison with a suitable control, for example the wildtype of the plant ("control plant", "starting plant"), to which the method according to the invention has not been applied, under otherwise identical conditions (such as, for example, climatic conditions, growing conditions, type of pathogen and the like). Preferably, at least the epidermis and/or mesophyll tissue in a plant, or the organs which have an epidermis and/or mesophyll tissue, have an increased resistance to the pathogens. For example, the resistance in the leaves is increased. In one embodiment, the resistance in lemma, palea and/or glume (anther primordium) is increased.

In one embodiment, the activity of the protein according to the invention, subtilisin RNR9, is therefore reduced in the abovementioned organs and tissues.

In this context, the increased resistance preferably manifests itself in a reduced manifestation of the disease symptoms, where disease symptoms—in addition to the abovementioned adverse effects—also comprises for example the penetration efficiency of a pathogen into the plant or the plant cell, or the proliferation efficiency in or on the same. In this context, the disease symptoms are preferably reduced by at least 10% or at least 20%, especially preferably by at least 40% or 60%, very especially preferably by at least 70%, 75%, 80% or 85%, most preferably by at least 90% or 95%.

For the purposes of the invention, "pathogen" means organisms whose interactions with a plant lead to the above-described disease symptoms; in particular, pathogens means organisms from the Kingdom Fungi. Preferably, pathogen is understood as meaning a pathogen which penetrates epidermis or mesophyll cells, especially preferably pathogens which penetrate plants via stomata and subsequently penetrate mesophyll cells. Organisms which are preferably mentioned in this context are those from the phyla Ascomycota and Basidiomycota. Especially preferred in this context are the families Blumeriaceae, Pucciniaceae, Mycosphaerellaceae and Hypocreaceae.

Especially preferred are organisms of these families which belong to the genera *Blumeria, Puccinia, Fusarium* or *Mycosphaerella*.

Very especially preferred are the species *Blumeria graminis, Puccinia triticina, Puccinia striiformis, Mycosphaerella graminicola, Stagonospora nodorum, Fusarium graminearum, Fusarium culmorum, Fusarium avenaceum, Fusarium poae* and *Microdochium nivale*.

However, it is to be assumed that the reduction in the expression of subtilisin RNR9, its activity or function also brings about a resistance to further pathogens.

Especially preferred are Ascomycota such as, for example, *Fusarium oxysporum* (fusarium wilt on tomato), *Septoria nodorum* and *Septoria tritici* (glume blotch on wheat), Basidiomycetes such as, for example, *Puccinia graminis* (stem rust on wheat, barley, rye, oats), *Puccinia recondita* (leaf rust on wheat), *Puccinia dispersa* (leaf rust on rye), *Puccinia hordei* (leaf rust on barley), *Puccinia coronata* (crown rust on oats).

In one embodiment, the method according to the invention leads to a resistance in barley to the pathogen:

*Rhynchosporium secale* (barley scald),
*Puccinia graminis* f. sp. *hordei* (barley stem rust), in wheat to the pathogens:

*Fusarium graminearum,*
*Fusarium avenaceum,*
*Fusarium culmorum,*
*Puccinia graminis* f. sp. *tritici,*
*Puccinia recondita* f. sp. *tritici,*
*Puccinia striiformis,*
*Septoria nodorum,*
*Septoria tritici,*
*Septoria avenae* or
*Puccinia graminis* f. sp. *tritici* (wheat stem rust), in maize to the pathogens:

*Fusarium moniliforme* var. *subglutinans,*
*Puccinia sorghi* or
*Puccinia polysora,* in sorghum to the pathogens:

*Puccinia purpurea,*
*Fusarium monilifonne,*
*Fusarium graminearum* or
*Fusarium oxysporum,* in soybean to the pathogens

*Phakopsora pachyrhizi* or
*Phakopsora meibromae.*

In a preferred embodiment, the invention relates to a subtilisin RNR9 polypeptide which has the activity shown in the examples.

In one embodiment, a subtilisin RNR9 protein is understood as meaning a protein with a homology to one of the amino acid sequences shown in FIG. 2, 4, 6, 8, 10, 12, 13 or 14, for example a subtilisin RNR9 polypeptide from maize (ZmSubtilisin RNR9) as shown in FIG. 10, from rice (*Oryza sativa*) as shown in FIG. 12 and/or from *A. thaliana* as shown in FIGS. 6 and 8, or according to one of the consensus sequences as shown in FIG. 13 or 14, or a functional fragment thereof. In one embodiment, the invention relates to functional equivalents of the abovementioned polypeptide sequences.

"Polypeptide quantity" means for example the number of molecules, or moles of subtilisin RNR9 polypeptide molecules in an organism, a tissue, a cell or a cell compartment. "Reducing" the polypeptide quantity means the molar reduction in the number of subtilisin RNR9 polypeptides, in particular of those shown in FIGS. 2, 4, 6, 8, 10, 12, in an organism, a tissue, a cell or a cell compartment—for example by one of the methods described hereinbelow—in comparison with a suitable control, for example the wildtype (control plant) of the same genus and species to which this method has not been applied, under otherwise identical conditions (such as, for example, culture conditions, age of the plants and the like). The reduction in this context amounts to at least 5%, preferably at least 10% or at least 20%, especially preferably at least 40%, 50% or 60%, very especially preferably at least 70% or 80%, most preferably at least 90%, 95%, 97% or 99%.

The present invention furthermore relates to the generation of a pathogen resistance by reducing the function or activity of a Subtilase polypeptide comprising the sequences shown in FIG. 2, 4, 6, 8, 10, 12 or of a homolog thereof and/or a polypeptide which has a homology of at least 35%, 40%, 45%, 50%, 60%, 70%, 75%, 80%, 85%, 90%, 92%, 95%, 97% or 99% with the above, and/or of a functional equivalent of the abovementioned polypeptides.

Homology between two nucleic acid sequences is understood as meaning the identity of the nucleic acid sequence over in each case the entire sequence length, in a preferred embodiment over the entire expressed sequence length, preferably cDNA, yet more preferably over the coding sequence, preferably CDS, which is calculated by comparison with the aid of the program algorithm GAP (Wisconsin Package Version 10.0, University of Wisconsin, Genetics Computer Group (GCG), Madison, USA; Altschuh et al. (1997) Nucleic Acids Res. 25:3389ff), setting the following parameters:

| | |
|---|---|
| Gap weight: 50 | Length weight: 3 |
| Average match: 10 | Average mismatch: 0 |

For example, a sequence which has at least 80% homology with the sequence as shown in FIG. 1 at the nucleic acid level is understood as meaning a sequence which, upon comparison with the sequence as shown in FIG. 1 by the above program algorithm with the above parameter set, has at least 80% homology.

"Identity between two proteins" is understood as meaning the identity of the amino acids over a specific protein region, preferably the entire length of the protein, in particular the identity which is calculated by comparison with the aid of software, for example the Lasergene software from DNA Star Inc. (Madison, Wis. (USA) using the CLUSTAL methods (Higgins et al., 1989), Comput. Appl. Biosci., 5 (2), 151). Homologies can also be calculated with the aid of the Lasergene software from DNA Star Inc. (Madison, Wis. (USA) using the CLUSTAL method (Higgins et al., 1989), Comput. Appl. Biosci., 5 (2), 151).

For the alignments shown herein (for example as in FIG. 16), the preset parameters from the webpage clustalw/ (Last updated: Oct. 17, 2005 11:27:35) were used with the following programs from FTP DIRECTORY:

ftp.ebi.ac.uk/pub/software/unix/clustalw/:
ParClustal0.1.tar.gz [Nov. 28, 2001] 823975
ParClustal0.2.tar.gz [Jun. 27, 2002] 2652452
README [Jun. 13, 2003] 673
clustalw1.8.UNIX.tar.gz [Jul. 4, 1999] 4725425
clustalw1.8.mp.tar.gz [May 2, 2000] 174859
clustalw1.81.UNIX.tar.gz [Jun. 7, 2000] 555655
clustalw1.82.UNIX.tar.gz [Feb. 6, 2001] 606683
clustalw1.82.mac-osx.tar.gz [Oct. 15, 2002] 669021
clustalw1.83.UNIX.tar.gz [Jan. 30, 2003] 166863

Homology between two polypeptides is preferably understood as meaning the identity of the amino acid sequence over the indicated entire sequence length which is calculated by comparison with the aid of the program algorithm GAP (Wisconsin Package Version 10.0, University of Wisconsin, Genetics Computer Group (GCG), Madison, USA), setting the following parameters:

| | |
|---|---|
| Gap weight: 8 | Length weight: 2 |
| Average match: 2.912 | Average mismatch: −2.003 |

For example, a sequence which has at least 80% homology at the polypeptide level with the sequence as shown in FIG. 2 is understood as meaning a sequence which, upon comparison with the sequence as shown in FIG. 2 by the above program algorithm with the above parameter set has at least 80% homology.

In a preferred embodiment of the present invention, the subtilisin RNR9 protein activity, function or polypeptide quantity is reduced in the plant or in a part of the plant, for example in a plant organ, plant tissue, a plant cell or a part of a plant cell, for example a plant-specific organelle. For example, the subtilisin RNR9 protein is encoded by a nucleic acid molecule comprising a nucleic acid molecule selected from the group consisting of:
(a) nucleic acid molecule which codes for a polypeptide which comprises the sequence shown in FIG. 2, 4, 6, 8, 10, 12, 13 or 14;
(b) nucleic acid molecule which comprises at least one polynucleotide of the sequence according to FIGS. 1, 3, 5, 7, 9, 11;
(c) nucleic acid molecule which codes for a functional polypeptide whose sequence has 40%, 50%, 60%, 65%, 70%, 75%, 80%, 85%, 90%, 95%, 97%, 98%, 99% or more identity to the sequences shown in FIG. 13 or 14;
nucleic acid molecule according to (a) to (c) which codes for a functional fragment or an epitope of the sequences as shown in FIG. 13 or 14;
nucleic acid molecule which codes for a polypeptide which is recognized by a monoclonal antibody directed against a polypeptide which is encoded by the nucleic acid molecules as shown in (a) to (c); and
nucleic acid molecule which hybridizes under stringent conditions with a nucleic acid molecule as shown in (a) to (c); or their part-fragments of at least 15 nucleotides (nt), preferably 20 nt, 30 nt, 50 nt, 100 nt, 200 nt, 500 nt, 750 nt, 1000 nt, 1250 nt, 1500 nt, 1750 nt or 2000 nt;
nucleic acid molecule which can be isolated from a DNA library using a nucleic acid molecule as shown in (a) to (c) or their part-fragments of at least 15 nt, preferably 20 nt, 30 nt, 50 nt, 100 nt, 200 nt, 500 nt, 750 nt, 1000 nt, 1250 nt, 1500 nt, 1750 nt or 2000 nt, as probe under stringent hybridization conditions;
or comprises a complementary sequence thereof or constitutes a functional equivalent thereof.

Preferably, the activity of the abovementioned polypeptides is reduced in the epidermal and/or mesophyll cells of a plant as detailed above.

In one embodiment, the activity of subtilisin RNR9 is reduced in lemma, palea and/or glume.

"Epitope" is understood as meaning the regions of an antigen which determine the specificity of the antibodies (the antigenic determinant). Accordingly, an epitope is the portion of an antigen which actually comes into contact with the antibody. Such antigenic determinants are those regions of an antigen to which the T-cell receptors react and, as a consequence, produce antibodies which specifically bind the antigenic determinant/epitope of an antigen. Accordingly, antigens, or their epitopes, are capable of inducing the immune response of an organism with the consequence of the formation of specific antibodies which are directed against the epitope. Epitopes consist for example of linear sequences of amino acids in the primary structure of proteins, or of complex secondary or tertiary protein structures. A hapten is understood as meaning a epitope which is dissociated from the context of the antigen environment. Although haptens have by definition an antibody directed against them, haptens are, under certain circumstances, not capable of inducing an immune response in an organism, for example after an injection. To this end, haptens are coupled with carrier molecules. An example which may be mentioned is dinitrophenol (DNP), which, after coupling to BSA (bovine serum albumine), has been used for generating antibodies which are directed against DNP (Bohn, A., König, W.; 1982).

Haptens are therefore substances (frequently small molecules) which, while they themselves do not trigger immune response, will indeed trigger such a response when coupled to a large molecular carrier.

The antibodies generated thus also include those which can bind to the hapten as such.

In one embodiment, the present invention relates to an antibody against a polypeptide characterized herein. In particular to a monoclonal antibody which binds a polypeptide which comprises an amino acid (AA) sequence or consists thereof, as shown in the sequences shown in FIG. 2, 4, 6, 8, 10, 12, 13 or 14.

Antibodies within the scope of the present invention can be used for identifying and isolating polypeptides disclosed in accordance with the invention from organisms, preferably plants, especially preferably monocotyledonous plants. The antibodies can either be monoclonal, polyclonal or synthetic in nature or else consist of antibody fragments such as Fab, Fv or scFv fragments, which are formed by proteolytic degradation. "Single chain" Fv (scFv) fragments are single-chain fragments which, linked via a flexible linker sequence only comprise the variable regions of the heavy and light antibody chains. Such scFv fragments can also be produced as recombinant antibody derivatives. A presentation of such antibody fragments on the surface of filamentous phages makes possible the direct selection, from combinatory phage libraries, of scFv molecules which bind with high affinity.

Monoclonal antibodies can be obtained in accordance with the method described by Köhler and Milstein (Nature 256 (1975), p. 495).

"Functional equivalents" of a subtilisin RNR9 protein preferably means those polypeptides which have at least 40% homology with the polypeptides described by the sequences as shown in FIG. 13 or 14 and which have essentially the same properties and/or function as the polypeptides shown in FIGS. 2, 4, 6, 8, 10, 12. Preferably, the homology amounts to 50%, 60%, 65%, 70%, 75, 80%, 85%, 90%, 95%, 97%, 98%, 99% or more.

The functional equivalence can be determined for example by comparing the phenotypes of test organisms after expression of the polypeptides in question, under the most identical conditions possible, or after reduction of the expression or activity of the polypeptides to be compared, in the source organisms in question.

"Essentially identical properties" of a functional equivalent means above all imparting a pathogen-resistant phenotype or imparting or increasing the pathogen resistance to at least one pathogen when reducing the polypeptide quantity, activity or function of said functional subtilisin RNR9 protein equivalent in a plant, organ, tissue, part or cells, in particular in epidermal or mesophyll cells of same, preferably measured by the penetration efficiency of a pathogen, as shown in the examples.

"Analogous conditions" means that all basic conditions such as, for example, culture or growth conditions, assay conditions (such as buffers, temperature, substrates, pathogen concentration and the like) between the experiments to be compared are kept identical and that the set-ups only differ by the sequence of the subtilisin RNR9 polypeptides to be compared, by their source organism and, if appropriate, by the pathogen.

"Functional equivalents" also means natural or artificial mutation variants of the subtilisin RNR9 polypeptides as shown in FIGS. 2, 4, 6, 8, 10, 12 and homologous polypeptides from other monocotyledonous and dicotyledonous plants which furthermore have essentially identical properties. Preferred are homologous polypeptides from preferred plants described herein. The sequences from other plants, which sequences are homologous to the subtilisin RNR9 protein sequences disclosed within the scope of the present invention, can be found readily for example by database search or by screening gene libraries using the subtilisin RNR9 protein sequences as search sequence or probe.

Functional equivalents can also be derived for example from one of the polypeptides according to the invention as shown in FIG. 2, 4, 6, 8, 10, 12, 13 or 14 by substitution, insertion or deletion and can have at least 60%, 70% preferably at least 80%, by preference at least 90%, especially preferably at least 95%, very especially preferably at least 98% homology with these polypeptides and are distinguished by essentially identical properties to the polypeptides as shown in FIG. 2, 4, 6, 8, 10, 12, 13 or 14.

Functional equivalents are also nucleic acid molecules which are derived from the nucleic acid sequences according to the invention as shown in FIG. 1, 3, 5, 7, 9 or 11 by substitution, insertion or deletion and have at least 60%, 70% preferably 80%, by preference at least 90%, especially preferably at least 95%, very especially preferably at least 98% homology with one of the polynucleotides according to the invention as shown in FIG. 1, 3, 5, 7, 9 or 11 and code for polypeptides with essentially identical properties to polypeptides as shown in FIG. 2, 4, 6, 8, 10, 12, 13 or 14.

Examples of the functional equivalents of the subtilisin RNR9 proteins as shown in FIG. 2, 4, 6, 8, 10, 12, 13 or 14 which are to be reduced in the method according to the invention can be found by homology comparisons from databases, from organisms whose genomic sequence is known.

Screening cDNA libraries or genomic libraries of other organisms, preferably of the plant species mentioned further below, which are suitable as transformation hosts, using the nucleic acid sequence as shown in FIG. 1, 3, 5, 7, 9 or 11 or parts of the same as probe is also a method known to the skilled worker for identifying homologs in other species. In this context, the probes derived from the nucleic acid sequence as shown in FIG. 1, 3, 5, 7, 9 or 11 have a length of at least 20 bp, preferably at least 50 bp, especially preferably at least 100 bp, very especially preferably at least 200 bp (bp=pasepair), most preferably at least 400 bp. The probe can also be one or more kilobases (kb) in length, for example 1 kb, 1.5 kb or 3 kb. A DNA or RNA strand which is complementary to the sequences as shown in FIG. 1, 3, 5, 7, 9 or 11 or a fragment of same strand with a length of between 20 bp and several kilobases may also be employed for screening the libraries.

In the method according to the invention, those DNA or RNA molecules which hybridize under standard conditions with the nucleic acid molecules as shown in FIG. 1, 3, 5, 7, 9 or 11 and which code for subtilisin RNR9 protein, with the nucleic acid molecules which are complementary to the above or with parts of the above and which, as complete sequences, code for polypeptides which have identical properties to the polypeptides as shown in FIGS. 2, 4, 6, 8, 10, 12 may also be used.

"Standard hybridization conditions" is to be understood in the broad sense and means, depending on the application, stringent or else less stringent hybridization conditions. Such hybridization conditions are described, inter alia, in Sambrook J, Fritsch E F, Maniatis T et al., (Molecular Cloning (A Laboratory Manual), 2nd edition, Cold Spring Harbor Laboratory Press, 1989, pages 9.31-9.57)) or in Current Protocols in Molecular Biology, John Wiley & Sons, N.Y. (1989), 6.3.1-6.3.6.

The skilled worker would choose hybridization conditions which allow him to differentiate between specific and unspecific hybridizations.

For example, the conditions during the wash step can be selected from among low-stringency conditions (with approximately 2×SSC at 50° C.) and high-stringency conditions (with approximately 0.2×SSC at 50° C., preferably at 65° C.) (20×SSC: 0.3M sodium citrate, 3M NaCl, pH 7.0). Moreover, the temperature during the wash step can be raised from low-stringency conditions at room temperature, approximately 22° C., to higher-stringency conditions at approximately 65° C. The two parameters, salt concentration and temperature can be varied simultaneously or else singly, keeping in each case the other parameter constant. During the hybridization, it is also possible to employ denaturant agents such as, for example, formamide or SDS. In the presence of 50% formamide, the hybridization is preferably carried out at 42° C. Some examples of conditions for hybridization and wash step are detailed hereinbelow:

(1) Hybridization conditions can be selected for example among the following conditions:
  a) 4×SSC at 65° C.,
  b) 6×SSC at 45° C.,
  c) 6×SSC, 100 µg/ml denatured fragmented fish sperm DNA at 68° C.,
  d) 6×SSC, 0.5% SDS, 100 µg/ml denatured salmon sperm DNA at 68° C.,
  e) 6×SSC, 0.5% SDS, 100 µg/ml denatured fragmented salmon sperm DNA, 50% formamide at 42° C.,
  f) 50% formamide, 4×SSC at 42° C., or
  g) 50% (vol/vol) formamide, 0.1% bovine serum albumin, 0.1% Ficoll, 0.1% polyvinylpyrrolidone, 50 mM sodium phosphate buffer pH 6.5, 750 mM NaCl, 75 mM sodium citrate at 42° C., or
  h) 2× or 4×SSC at 50° C. (low-stringency condition),
  i) 30 to 40% formamide, 2× or 4×SSC at 42° C. (low-stringency condition),
  j) 500 mM sodium phosphate buffer pH 7.2, 7% SDS (g/V), 1 mM EDTA, 10 µg/ml single stranded DNA, 0.5% BSA (g/V) (Church and Gilbert, Genomic sequencing. Proc. Natl. Acad. Sci. U.S.A. 81:1991. 1984)

(2) Wash steps can be selected for example among the following conditions:
  a) 0.015 M NaCl/0.0015 M sodium citrate/0.1% SDS at 50° C.,
  b) 0.1×SSC at 65° C.,
  c) 0.1×SSC, 0.5% SDS at 68° C.,
  d) 0.1×SSC, 0.5% SDS, 50% formamide at 42° C.,
  e) 0.2×SSC, 0.1% SDS at 42° C.,
  f) 2×SSC at 65° C. (low-stringency condition)

In one embodiment, the hybridization conditions are selected as follows:

A hybridization buffer comprising formamide, NaCl and PEG 6000 is chosen. The presence of formamide in the hybridization buffer destabilizes double-strand nucleic acid molecules, whereby the hybridization temperature can be lowered to 42° C. without thereby reducing the stringency. The use of salt in the hybridization buffer increases the renaturation rate of a duplex, in other words the hybridization efficiency. Although PEG increases the viscosity of the solution, which has a negative effect on the renaturation rates, the presence of the polymer in the solution increases the concentration of the probe in the remaining medium, which increases the hybridization rate. The composition of the buffer is as follows:

| Hybridization buffer |
| --- |
| 250 mM sodium phosphate buffer pH 7.2 |
| 1 mM EDTA |
| 7% SDS (g/v) |
| 250 mM NaCl |
| 10 µg/ml ssDNA |
| 5% polyethylene glycol (PEG) 6000 |
| 40% formamide |

The hybridizations are carried out overnight at 42° C. On the following morning, the filters are washed 3× with 2×SSC+ 0.1% SDS for in each case approximately 10 minutes.

In a further preferred embodiment of the present invention, an increase in the resistance in the method according to the invention is achieved by (a) reducing the expression of at least one subtilisin RNR9 protein;
(b) reducing the stability of at least one subtilisin RNR9 protein or of the mRNA molecules which correspond to this subtilisin RNR9 protein;
(c) reducing the activity of at least one subtilisin RNR9 protein;
(d) reducing the transcription of at least one gene which codes for subtilisin RNR9 protein by expressing an endogenous or artificial transcription factor;
(e) adding, to the food or to the medium, an exonogous factor which reduces the subtilisin RNR9 protein activity; or
(f) reducing the expression and/activity by spraying a chemical inhibitor on plants.

"Gene expression" and "expression" are to be understood as being synonymous and mean the realization of the information which is stored in a nucleic acid molecule. Reducing the expression of a gene therefore comprises the reduction of the polypeptide quantity of the encoded protein, for example of the subtilisin RNR9 polypeptide or of the subtilisin RNR9 protein function. The reduction of the gene expression of a subtilisin RNR9 protein gene can be realized in many different ways, for example by one of the methods listed hereinbelow.

"Reduction", "reducing" or "to reduce" in the context of a subtilisin RNR9 protein or subtilisin RNR9 protein function is to be interpreted in the broad sense and comprises the partial or essentially complete inhibition or blockage of the functionality of a subtilisin RNR9 polypeptide in a plant or a part, tissue, organ, cells or seeds derived therefrom, based on different cell-biological mechanisms.

Reducing within the meaning of the invention also comprises a quantitative reduction of a subtilisin RNR9 polypeptide down to an essentially complete absence of the subtilisin RNR9 polypeptide (i.e. lack of detectability of subtilisin RNR9 protein function or lack of immunological detectability of the subtilisin RNR9 protein). Here, the expression of a certain subtilisin RNR9 polypeptide or the subtilisin RNR9 protein function in a cell or an organism is preferably reduced by more than 50%, especially preferably by more than 80%, very especially preferably by more than 90%, in comparison with a suitable control, i.e. to the wildltype of the same type, for example of the same genus, species, variety, cultivar and the like ("control plants"), to which this method has not been applied, under otherwise identical conditions (such as, for example, culture conditions, age of the plants and the like).

In accordance with the invention, there are described various strategies for reducing the expression of a subtilisin RNR9 protein or a subtilisin RNR9 protein function. The skilled worker recognizes that a series of further methods is available for influencing the expression of a subtilisin RNR9 polypeptide or of the subtilisin RNR9 protein function in the desired manner.

In one embodiment, a reduction in the subtilisin RNR9 protein function is achieved in the method according to the invention by applying at least one method selected from the group consisting of:

a) Introducing a nucleic acid molecule coding for ribonucleic acid molecules suitable for forming double-strand ribonucleic acid molecules (dsRNA), where the sense strand of the dsRNA molecule has at least 20%, 30%, 40% homology with the nucleic acid molecule according to the invention, for example with one of the nucleic acid molecules as shown in FIG. 1, 3, 5, 7, 9, 11, or coding for a consensus sequence as shown in FIG. 13 or 14, or comprises a fragment of at least 17 base pairs, which has at least 40%, 50%, 60% homology with a nucleic acid molecule according to the invention, for example as shown in FIG. 1, 3, 5, 7, 9, 11, or coding for a consensus sequence as shown in FIG. 13 or 14, or with a functional equivalent of same, or introducing (an) expression cassette(s) which ensure(s) their expression.

b) Introducing a nucleic acid molecule coding for an antisense ribonucleic acid molecule which has at least 20%, 30%, 40% homology with the noncoding strand of one of the nucleic acid molecules according to the invention, for example a nucleic acid molecule as shown in FIG. 1, 3, 5, 7, 9, 11, or coding for a consensus sequence as shown in FIG. 13 or 14, or comprising a fragment of at least 15 base pairs with at least 40%, 50%, 60% homology with a noncoding strand of a nucleic acid molecule according to the invention, for example as shown FIG. 1, 3, 5, 7, 9, 11, or coding for a consensus sequence as shown in FIG. 13 or 14, or with a functional equivalent thereof. Comprised are those methods in which the antisense nucleic acid sequence against a subtilisin RNR9 protein gene (i.e. genomic DNA sequences) or a subtilisin RNR9 protein gene transcript (i.e. RNA sequences). Also comprised are α-anomeric nucleic acid sequences.

c) Introducing a ribozyme which specifically cleaves, for example catalytically, the ribonucleic acid molecules encoded by a nucleic acid molecule according to the invention, for example as shown in FIG. 1, 3, 5, 7, 9, 11, or coding for a consensus sequence as shown in FIG. 13 or 14, or by their functional equivalents, by introducing an expression cassette which ensures the expression of such a ribozyme.

d) Introducing an antisense nucleic acid molecule as specified in b), in combination with a ribozyme or with an expression cassette which ensures the expression of the ribozyme.

e) Introducing nucleic acid molecules coding for sense ribonucleic acid molecules of a polypeptide according to the invention, for example as shown in FIGS. 2, 4, 6, 8, 10, 12, for polypeptides with at least 30%, 40%, 50% homology with the amino acid sequence of a protein according to the invention, or is a functional equivalent thereof.
f) Introducing a nucleic acid sequence coding for a dominant-negative polypeptide suitable for suppressing the subtilisin RNR9 protein function, or introducing an expression cassette which ensures the expression of this nucleic acid sequence.
g) Introducing a factor which can specifically bind subtilisin RNR9 polypeptides or the DNA or RNA molecules coding for these polypeptides, or introducing an expression cassette which ensures the expression of this factor.
h) Introducing a viral nucleic acid molecule which brings about a degradation of mRNA molecules which code for a subtilisin RNR9 protein, or introducing an expression cassette which ensures the expression of this nucleic acid molecule.
i) Introducing a nucleic acid construct suitable for inducing a homologous recombination on genes coding for a subtilisin RNR9 protein.
j) Introducing one or more mutations into one or more coding gene(s) coding for a subtilisin RNR9 protein for generating a loss of function (for example generation of stop codons, reading-frame shifts and the like).

These and modified methods, and further methods, are known to the skilled worker and extensively described, for example also in PCT/EP2005/003297, which is explicitly included herein by reference with regard to these methods.

Each one of these methods can bring about a reduction in the subtilisin RNR9 protein expression or subtilisin RNR9 protein function for the purposes of the invention. A combined use is also feasible. Further methods are known to the skilled worker and can comprise the hindering or prevention of the processing of the subtilisin RNR9 polypeptide, of the transport of the subtilisin RNR9 polypeptide or its mRNA, inhibition of the ribosome attachment, inhibition of the RNA splicing, induction of a subtilisin-RNR9-protein-RNA-degrading enzyme and/or inhibition of the translational elongation or termination.

A reduction in the subtilisin RNR9 protein function or subtilisin RNR9 polypeptide quantity is preferably achieved by a reduced expression of an endogenous subtilisin RNR9 protein gene.

The individual preferred processes shall be described briefly hereinbelow:
a) Introducing a double-stranded subtilisin RNR9 protein RNA nucleic acid sequence (subtilisin RNR9 protein dsRNA).

The method of regulating genes by means of double-stranded RNA ("double-stranded RNA interference"; dsRNAi) has been described many times for animal and plant organisms (e.g. Matzke M A et al. (2000) Plant Mol Biol 43:401-415; Fire A. et al (1998) Nature 391:806-811; WO 99/32619; WO 99/53050; WO 00/68374; WO 00/44914; WO 00/44895; WO 00/49035; WO 00/63364). Efficient gene suppression can also be demonstrated in the case of transient expression, or following the transient transformation, for example as the result of a biolistic transformation (Schweizer P et al. (2000) Plant J 2000 24: 895-903). dsRNAi processes are based on the phenomenon that simultaneously introducing the complementary strand and counterstrand of a gene transcript suppresses the expression of the corresponding gene in a highly efficient manner. The phenotype caused is very similar to that of a corresponding knock-out mutant (Waterhouse P M et al. (1998) Proc Natl Acad Sci USA 95:13959-64).

The dsRNAi method has proved to be particularly efficient and advantageous when reducing the subtilisin RNR9 protein expression (WO 99/32619).

With regard to the double-stranded RNA molecules, subtilisin RNR9 nucleic acid sequence preferably means one of the sequences as shown in FIG. 1, 3, 5, 7, 9 or 11, or coding for a consensus sequence as shown in FIG. 13 or 14, or sequences which are essentially identical to those, preferably which have at least 50%, 60%, 70%, 75%, 80%, 85% or 90% or more identity to these, for example approximately 95%, 96%, 97%, 98%, 99% or more identity to these, or functional fragments of these with a length of at least 17 base pairs. "Essentially identical" means here that the dsRNA sequence may also have insertions, deletions and individual point mutations in comparison with the subtilisin RNR9 protein target sequence while still bringing about an efficient reduction in the expression. In one embodiment, the homology as defined above is at least 50%, 60%, for example approximately 70%, 80%, or approximately 90%, or approximately 100%, between the "sense" strand of an inhibitory dsRNA and a subsection of a subtilisin RNR9 nucleic acid sequence (or between the "antisense" strand and the complementary strand of a subtilisin RNR9 nucleic acid sequence). The length of the subsection is approximately 17 bases or more, for example approximately 25 bases, or approximately 50 bases, approximately 100 bases, approximately 200 bases or approximately 300 bases. Alternatively, an "essentially identical" dsRNA can also be defined as a nucleic acid sequence which is capable of hybridizing under stringent conditions with a part of a subtilisin RNR9 protein gene transcript.

The "antisense" RNA strand, too, can have insertions, deletions and individual point mutations in comparison with the complement of the "sense" RNA strand. The homology is preferably at least 80%, for example approximately 90%, or approximately 95%, or approximately 100%, between the "antisense" RNA strand and the complement of the "sense" RNA strand.

"Subsection of the "sense" RNA transcript" of a nucleic acid molecule coding for a subtilisin RNR9 polypeptide or a functional equivalent thereof means fragments of an RNA or mRNA transcribed by a nucleic acid molecule coding for a subtilisin RNR9 polypeptide or a functional equivalent thereof, preferably by a subtilisin RNR9 protein gene. In this context, the fragments preferably have a sequence length of approximately 20 bases or more, for example approximately 50 bases, or approximately 100 bases, or approximately 200 bases, or approximately 500 bases. Also comprised is the complete transcribed RNA or mRNA.

The dsRNA can consist of one or more strands of polymerized ribonucleotides. Modifications both of the sugar-phosphate backbone and of the nucleosides may also be present. For example, the phosphodiester bonds of the natural RNA can be modified in such a way that they comprise at least one nitrogen or sulfur heteroatom. Bases can be modified in such a way that the activity of, for example, adenosine-deaminase is restricted. Such and further modifications are described hereinbelow in the methods of stabilizing antisense RNA.

To achieve the same purpose, it is, of course, also possible to introduce, into the cell or the organism, a plurality of individual dsRNA molecules, each of which comprises one of the above-defined ribonucleotide sequence segments.

The dsRNA can be prepared enzymatically or fully or partially by chemical synthesis.

If the two strands of the dsRNA are to be combined in one cell or plant, this can be accomplished in various ways:

a) transformation of the cell or plant with a vector which comprises both expression cassettes, b) cotransformation of the cell or plant with two vectors, where one comprises the expression cassettes with the "sense" strand while the other one comprises the expression cassettes with the "antisense" strand, and/or c) hybridization of two plants which have been transformed with in each case one vector, where one comprises the expression cassettes with the "sense" strand, while the other one comprises the expression cassettes with the "antisense" strand.

The formation of the RNA duplex can be initiated either externally or internally of the cell. As described in WO 99/53050, the dsRNA can also comprise a hairpin structure, by linking "sense" and "antisense" strand by means of a "linker" (for example an intron). The autocomplementary dsRNA structures are preferred since they only require the expression of a construct and always comprise the complementary strands in an equimolar ratio.

The expression cassettes coding for the "antisense" or "sense" strand of a dsRNA or for the autocomplementary strand of the dsRNA are preferably inserted into a vector and stably (for example using selection markers) inserted into the genome of a plant using the methods described hereinbelow in order to ensure permanent expression of the dsRNA.

The dsRNA can be introduced using a quantity which makes possible at least one copy per cell. Higher quantities (for example at least 5, 10, 100, 500 or 1000 copies per cell) can make, if appropriate, a more efficient reduction.

In order to bring about an efficient reduction in the subtilisin RNR9 protein expression, 100% sequence identity between dsRNA and a subtilisin RNR9 protein gene transcript or the gene transcript of a functionally equivalent gene is not necessarily required. Accordingly, there is the advantage that the method tolerates sequence deviations as they can exist as the result of genetic mutations, polymorphisms or evolutionary divergences. The large number of highly conserved amino acid residues between different subtilisin RNR9 protein sequences of different plants, as shown in FIG. 16 with reference to the consensus sequences (see FIG. 13 or 14) allows the conclusion that this polypeptide is highly conserved within plants, so that the expression of a dsRNA derived from one of the disclosed subtilisin RNR9 protein sequences as shown in FIG. 2, 4, 6, 8, 10 or 12 should also have an advantageous effect in other plant species.

As the result of the high number of conserved residues and of the homology between the individual subtilisin RNR9 polypeptides and their functional equivalents, it may also be possible to suppress the expression of further homologous subtilisin RNR9 polypeptides and/or their functional equivalents of the same organism, or else the expression of subtilisin RNR9 polypeptides in other, related species, using a single dsRNA sequence which has been generated starting from a specific subtilisin RNR9 protein sequence of an organism. For this purpose, the dsRNA preferably comprises sequence regions of subtilisin RNR9 protein gene transcripts which correspond to conserved regions. Said conserved regions can be derived readily from sequence alignments, for example as shown in the FIG. 13, 14 or 16. It is preferred to derive dsRNA sequences from the conserved regions of the consensus sequence which are shown in the FIG. 13 or 14.

A dsRNA can be synthesized chemically or enzymatically. To this end, it is possible to use cellular RNA polymerases or bacteriophage RNA-polymerases (such as, for example, T3-, T7- or SP6-RNA-polymerase). Suitable methods for the in vitro expression of RNA are described (WO 97/32016; U.S. Pat. No. 5,593,874; U.S. Pat. No. 5,698,425, U.S. Pat. No. 5,712,135, U.S. Pat. No. 5,789,214, U.S. Pat. No. 5,804,693). A dsRNA which has been synthetized chemically or enzymatically in vitro can be purified from the reaction mixture fully or in part, for example by extraction, precipitation, electrophoresis, chromatography or combinations of these methods, before it is introduced into a cell, tissue or organism. The dsRNA can be introduced into the cell directly or else applied extracellularly (for example into the interstitial space).

However, it is preferred to transform the plant stably with an expression construct which realizes the expression of the dsRNA. Suitable methods are described hereinbelow.

b) Introduction of a subtilisin RNR9 protein antisense nucleic acid sequence

Methods of suppressing a certain polypeptide by preventing the accumulation of its mRNA by means of the "antisense" technology have been described many times, including in plants (Sheehy et al. (1988) Proc Natl Acad Sci USA 85: 8805-8809; U.S. Pat. No. 4,801,340; Mol J N et al. (1990) FEBS Lett 268(2): 427-430). The antisense nucleic acid molecule hybridizes with, or binds to, the cellular mRNA and/or genomic DNA coding for the callose synthase target polypeptide to be suppressed. The transcription and/or translation of the target polypeptide is thereby suppressed. The hybridization can be accomplished in a traditional manner via the formation of a stable duplex or, in the case of genomic DNA, by binding the antisense nucleic acid molecule to the duplex of the genomic DNA as the result of specific interaction in the large groove of the DNA helix.

An antisense nucleic acid molecule suitable for reducing a subtilisin RNR9 polypeptide can be derived using the nucleic acid sequence which codes for this polypeptide, for example the nucleic acid molecule according to the invention as shown in FIG. 1, 3, 5, 7, 9 or 11 or a nucleic acid molecule coding for a functional equivalent thereof following Watson's and Crick's base-pairing rules. The antisense nucleic acid molecule can be complementary to all of the transcribed mRNA of the said polypeptide, be limited to the coding region or else only consist of an oligonucleotide which is complementary to part of the coding or noncoding sequence of the mRNA. Thus, for example, the oligonucleotide can be complementary to the region which comprises the translation start for said polypeptide. Antisense nucleic acid molecules can have a length of, for example, 20, 25, 30, 35, 40, 45 or 50 nucleotides, but they may also be longer and comprise 100, 200, 500, 1000, 2000 or 5000 nucleotides. Antisense nucleic acid molecules can be expressed recombinantly or synthesized chemically or enzymatically, using methods known to the skilled worker. In the case of chemical synthesis, natural or modified nucleotides can be used. Modified nucleotides can impart an increased biochemical stability to the antisense nucleic acid molecule and lead to an increased physical stability of the duplex formed of antisense nucleic acid sequence and sense target sequence. Examples which can be used are phosphoro-thioate derivatives and acridine-substituted nucleotides such as 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylamino-methyluracil, 5-methoxyaminomethyl-2-thiouracil, β-D-mannosylqueosine, 5'-methoxycarboxymethyluracil, 5-methoxyuracil, 2-methylthio-N-6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid, 5-methyl-2-thiouracil, 3-(3-amino-3-N-2-carboxypropyl)uracil and 2,6-diaminopurine.

In a further preferred embodiment, the expression of a subtilisin RNR9 polypeptide can be inhibited by nucleic acid molecules which are complementary to a conserved region (for example a region which has been conserved as described above) or to a regulatory region of a subtilisin RNR9 protein gene (for example a subtilisin RNR9 protein promoter and/or enhancer) and which form triple-helical structures with the DNA double helix therein, so that the transcription of the subtilisin RNR9 protein gene is reduced. Suitable methods have been described (Helene C (1991) Anticancer Drug Res 6(6): 569-84; Helene C et al. (1992) Ann N Y Acad Sci 660: 27-36; Maher L J (1992) Bioassays 14(12): 807-815).

In a further embodiment, the antisense nucleic acid molecule can be an α-anomeric nucleic acid. Such α-anomeric nucleic acid molecules form specific double-stranded hybrids with complementary RNA in which—as opposed to the conventional β-nucleic acids—the two strands run in parallel with one another (Gautier C et al. (1987) Nucleic Acids Res 15:6625-6641). The antisense nucleic acid molecule can furthermore also comprise 2'-O-methylribonucleotides (Inoue et al. (1987) Nucleic Acids Res 15:6131-6148) or chimeric RNA-DNA analogs (Inoue et al. (1987) FEBS Lett 215:327-330).

c) Introduction of a ribozyme which specifically, for example catalytically, cleaves the ribonucleic acid molecules coding for subtilisin RNR9 protein.

Catalytic RNA molecules or ribozymes can be adapted to any target RNA and cleave the phosphodiester backbone at specific positions, whereby the target RNA is functionally deactivated (Tanner N K (1999) FEMS Microbiol Rev 23(3): 257-275). As a result, the ribozyme is not modified itself, but is capable of cleaving further target RNA molecules in an analogous manner, whereby it obtains the characteristics of an enzyme.

In this manner, it is possible to use ribozymes (for example hammerhead ribozymes; Haselhoff and Gerlach (1988) Nature 334:585-591) in order to cleave the mRNA of an enzyme to be suppressed, for example callose-synthases, and to prevent translation. Methods of expressing ribozymes for reducing certain polypeptides are described in EP 0 291 533, EP 0 321 201, EP 0 360 257. A ribozyme expression has also been described in plant cells (Steinecke P et al. (1992) EMBO J. 11(4): 1525-1530; de Feyter R et al. (1996) Mol Gen Genet. 250(3): 329-338). Ribozymes can be identified from a library of various ribozymes via a selection process (Bartel D and Szostak J W (1993) Science 261: 1411-1418). Preferably, the binding regions of the ribozyme hybridize with the conserved regions of the subtilisin RNR9 protein as described above.

d) Introduction of a subtilisin RNR9 protein antisense nucleic acid sequence in combination with a ribozyme.

The above-described antisense strategy can advantageously be coupled with a ribozyme method. The incorporation of ribozyme sequences into "antisense" RNAs imparts this enzyme-like, RNA-cleaving characteristic to precisely these antisense RNAs and thus increases their efficiency in the inactivation of the target RNA. The preparation and use of suitable ribozyme "antisense" RNA molecules is described, for example, in Haselhoff et al. (1988) Nature 334: 585-591.

The ribozyme technology can increase the efficiency of an antisense strategy. Suitable target sequences and ribozymes can be determined for example as described in Steinecke P, Ribozymes, Methods in Cell Biology 50, Galbraith et al. eds, Academic Press, Inc. (1995), p. 449-460, by calculating the secondary structure of ribozyme RNA and target RNA and by their interaction (Bayley C C et al. (1992) Plant Mol. Biol. 18(2): 353-361; Lloyd A M and Davis R W et al. (1994) Mol Gen Genet. 242(6): 653-657). For example, it is possible to construct derivatives of the Tetrahymena L-19 IVS RNA which derivatives have complementary regions to the mRNA of the subtilisin RNR9 protein to be suppressed (see also U.S. Pat. No. 4,987,071 and U.S. Pat. No. 5,116,742).

e) Introduction of a subtilisin RNR9 protein sense nucleic acid sequence for inducing a cosuppression The expression of a subtilisin RNR9 protein nucleic acid sequence in sense orientation can lead to a cosuppression of the corresponding homologous, endogenous gene. The expression of sense RNA with homology to an endogenous gene can reduce or cancel the expression of the former, similar to what has been described for antisense approaches (Jorgensen et al. (1996) Plant Mol Biol 31(5): 957-973; Goring et al. (1991) Proc Natl Acad Sci USA 88: 1770-1774; Smith et al. (1990) Mol Gen Genet. 224: 447-481; Napoli et al. (1990) Plant Cell 2: 279-289; Van der Krol et al. (1990) Plant Cell 2:291-99). Here, the construct introduced can represent the homologous gene to be reduced either fully or only in part. The possibility of translation is not required. The application of this technology to plants is described for example in Napoli et al. (1990) The Plant Cell 2: 279-289 and in U.S. Pat. No. 5,034,323.

The cosuppression is preferably realized using a sequence which is essentially identical to at least part of the nucleic acid sequence coding for a subtilisin RNR9 protein or a functional equivalent thereof, for example of the nucleic acid molecule according to the invention, for example of the nucleic acid sequences as shown in FIG. 1, 3, 5, 7, 9 or 11, or of the nucleic acid sequence coding for a functional equivalent thereof.

f) Introduction of nucleic acid sequences coding for a dominant-negative subtilisin RNR9 protein.

The activity of a subtilisin RNR9 protein can probably also be realized by expression of a dominant-negative variant of this subtilisin RNR9 protein. Methods of reducing the function or activity of a polypeptide by means of coexpression of its dominant-negative form are known to the skilled worker (Lagna G and Hemmati-Brivanlou A (1998) Current Topics in Developmental Biology 36: 75-98; Perlmutter R M and Alberola-Ila J (1996) Current Opinion in Immunology 8(2): 285-90; Sheppard D (1994) American Journal of Respiratory Cell & Molecular Biology. 11(1): 1-6; Herskowitz I (1987) Nature 329 (6136): 219-22).

A dominant-negative subtilisin RNR9 protein variant can be accomplished for example by altering amino acid residues which are part of the end, as the result of their mutation, the polypeptide loses its function. Amino acid residues which are preferably to be mutated are those which are conserved in the subtilisin RNR9 proteins of different organisms. Such conserved regions can be determined for example by means of computer-aided comparison ("alignment"). These mutations for obtaining a dominant-negative subtilisin RNR9 protein variant are preferably carried out at the level of the nucleic acid sequence coding for subtilisin RNR9 proteins. A suitable mutation can be realized for example by PCR-mediated in vitro mutagenesis using suitable oligonucleotide primers, by means of which the desired mutation is introduced. Methods which are known to the skilled worker are used for this purpose. For example, the "LA PCR in vitro Mutagenesis Kit" (Takara Shuzo, Kyoto) can be used for this purpose.

g) Introduction of subtilisin RNR9 protein genes, RNAs or polypeptide-binding factors.

A reduction of a subtilisin RNR9 protein gene expression is also possible using specific DNA-binding factors, for example using factors of the zinc finger transcription factor type. These factors attach to the genomic sequence of the endogenous target gene, preferably in the regulatory regions, and bring about a repression of the endogenous gene. The use of such a method makes possible the reduction of the expression of an endogenous subtilisin RNR9 protein gene without it being necessary to recombinantly manipulate the sequence of the latter. Suitable methods for the preparation of suitable factors are described (Dreier B et al. (2001) J Biol Chem 276(31): 29466-78; Dreier B et al. (2000) J Mol Biol 303(4): 489-502; Beerli R R et al. (2000) Proc Natl Acad Sci USA 97 (4): 1495-1500; Beerli R R et al. (2000) J Biol Chem 275(42): 32617-32627; Segal D J and Barbas C F 3rd. (2000) Curr Opin Chem Biol 4(1): 34-39; Kang J S and Kim J S (2000) J Biol Chem 275(12): 8742-8748; Beerli R R et al. (1998) Proc Natl Acad Sci USA 95(25): 14628-14633; Kim J S et al. (1997) Proc Natl Acad Sci USA 94(8): 3616-3620; Klug A (1999) J Mol Biol 293(2): 215-218; Tsai S Y et al. (1998) Adv Drug Deliv Rev 30(1-3):23-31; Mapp A K et al. (2000) Proc Natl Acad Sci USA 97(8): 3930-3935; Sharrocks A D et al. (1997) Int Biochem Cell Biol 29(12): 1371-1387; Zhang L et al. (2000) J Biol Chem 275(43): 33850-33860).

The selection of these factors can be accomplished using a suitable portion of a subtilisin RNR9 protein gene. This segment is preferably located in the region of the promoter region. However, for the purpose of suppressing a gene, it may also be located in the region of the coding exons or introns. The corresponding segments are obtainable for the skilled worker by means of database search from the gene library or, starting from a subtilisin RNR9 protein cDNA whose gene is not present in the gene library, by screening a genomic library for corresponding genomic clones. The methods required for this purpose are known to the skilled worker.

Furthermore, it is possible to introduce, into a cell, factors which themselves inhibit the subtilisin RNR9 protein target polypeptide. The polypeptide-binding factors can be, for example, aptamers (Famulok M and Mayer G (1999) Curr Top Microbiol Immunol 243: 123-36) or antibodies or antibody fragments. The preparation of these factors is described and known to the skilled worker. For example, a cytoplasmic scFv antibody has been employed for modulating the activity of the phytochrome A protein in recombinantly modified tobacco plants (Owen M et al. (1992) Biotechnology (NY) 10(7): 790-794; Franken E et al. (1997) Curr Opin Biotechnol 8(4): 411-416; Whitelam (1996) Trend Plant Sci 1: 286-272).

Gene expression can also be suppressed by customized, low-molecular-weight synthetic compounds, for example of the polyamide type (Dervan P B and Burli R W (1999) Current Opinion in Chemical Biology 3: 688-693; Gottesfeld J M et al. (2000) Gene Expr 9(1-2): 77-91). These oligomers consist of the units 3-(dimethylamino)propylamine, N-methyl-3-hydroxypyrrole, N-methylimidazole and N-methylpyrrole and can be adapted to each segment of double-stranded DNA in such a way that they bind into the major group in a sequence-specific fashion and block the expression of the gene sequences therein. Suitable methods are described (see, inter alia, Bremer R E et al. (2001) Bioorg Med. Chem. 9(8): 2093-103; Ansari A Z et al. (2001) Chem. Biol. 8(6): 583-92; Gottesfeld J M et al. (2001) J Mol. Biol. 309(3): 615-29; Wurtz N R et al. (2001) Org Lett 3(8): 1201-3; Wang C C et al. (2001) Bioorg Med Chem 9(3): 653-7; Urbach A R and Dervan P B (2001) Proc Natl Acad Sci USA 98(8): 4343-8; Chiang S Y et al. (2000) J Biol. Chem. 275(32): 24246-54).

h) Introduction of the viral nucleic acid molecules and expression constructs which bring about the degradation of subtilisin RNR9 protein RNA.

The subtilisin RNR9 protein expression can also be realized efficiently by induction of the specific subtilisin RNR9 protein RNA degradation by the plant with the aid of a viral expression system (Amplikon) (Angell, S M et al. (1999) Plant J. 20(3): 357-362). These systems—also referred to as "VIGS" (viral-induced gene silencing)—introduce, by means of viral vectors, nucleic acid sequences with homology to the transcripts to be suppressed into the plant. Transcription is then cancelled, probably mediated by plant defence mechanisms against viruses. Suitable techniques and methods are described (Ratcliff F et al. (2001) Plant J 25(2): 237-45; Fagard M and Vaucheret H (2000) Plant Mol Biol 43(2-3): 285-93; Anandalakshmi R et al. (1998) Proc Natl Acad Sci USA 95(22): 13079-84; Ruiz M T (1998) Plant Cell 10(6): 937-46).

The methods of the dsRNAi, of cosuppression by means of sense RNA and of "VIGS" ("virus-induced gene silencing") are also referred to as "post-transcriptional gene silencing" (PTGS). PTGS methods are particularly advantageous because the demands for the homology between the endogenous gene to be suppressed and the recombinantly expressed sense or dsRNA nucleic acid sequence are less stringent than, for example, in a traditional antisense approach. Suitable homology criteria are mentioned in the description of the dsRNAi method and can generally be applied to PTGS methods or dominant-negative approaches. As the result of the high degree of homology between the Subtilase proteins from barley, wheat, and *Arabidopsis*, it can be concluded that this polypeptide is highly conserved in plants. Thus, it is probably also possible, using the SUB1 protein nucleic acid molecules as they are shown herein, in particular by means of the nucleic acid molecules which are derived from the consensus sequences, or else for example from the nucleic acid molecules from *Arabidopsis*, barley, maize or rice, also efficiently to suppress the expression of homologous SUB1 polypeptides in other species without the isolation and structure elucidation of the SUB1 protein homologs found in these species being compulsory. This substantially simplifies the labor required.

i) Introduction of a nucleic acid construct suitable for inducing a homologous recombination on genes coding for subtilisin RNR9 proteins, for example for the generation of knockout mutants.

To generate a homologously-recombinant organism with reduced subtilisin RNR9 protein function, one uses for example a nucleic acid construct which comprises at least part of an endogenous subtilisin RNR9 protein gene which is modified by a deletion, addition or substitution of at least one nucleotide, for example in the conserved regions, in such a way that the functionality is reduced or entirely nullified.

For example, the primary, secondary, tertiary or quaternary structure can be disrupted, for example in such a manner that the binding ability, or regulatory ability, of the cytoplasmic protein domain or the integration of the protein into the membrane no longer exists or is disrupted, in particular reduced. Such a disruption can be accomplished for example by the mutation of one or more residues which are indicated in the consensus sequence as being conserved or highly conserved.

The modification can also relate to the regulatory elements (for example the promoter) of the gene, so that the coding sequence remains unaltered, but that expression (transcription and/or translation) does not take place and/or is reduced.

In the case of conventional homologous recombination, the modified region is flanked at its 5' and 3' terminus by further nucleic acid sequences which must be of sufficient length for making possible the recombination. As a rule, the length is in the range of from several hundred or more bases up to several kilobases (Thomas K R and Capecchi M R (1987) Cell 51: 503; Strepp et al. (1998) Proc Natl Acad Sci USA 95(8): 4368-4373). To carry out the homologous recombination, the host organism—for example a plant—is transformed with the recombination construct using the methods described hereinbelow, and clones which have undergone successful recombination are selected using for example a resistance to antibiotics or herbicides.

j) Introduction of mutations into endogenous subtilisin RNR9 protein genes for generating a loss of function (for example generation of stop codons, reading-frame shifts and the like)

Further suitable methods for reducing the subtilisin RNR9 protein function are the introduction of nonsense mutations into endogenous subtilisin RNR9 protein genes, for example by means of generation of knockout mutants with the aid of, for example, T-DNA mutagenesis (Koncz et al. (1992) Plant Mol Biol 20(5): 963-976), ENU (N-ethyl-N-nitrosourea)—mutagenesis or homologous recombination (Hohn B and Puchta (1999) H Proc Natl Acad Sci USA 96: 8321-8323) or EMS mutagenesis (Birchler J A, Schwartz D. Biochem Genet. 1979 December; 17(11-12): 1173-80; Hoffmann G R. Mutat Res. 1980 January; 75(1): 63-129). Point mutations can also be generated by means of DNA-RNA hybrid oligonucleotides, which are also known as "chimeraplasty" (Zhu et al. (2000) Nat Biotechnol 18(5): 555-558, Cole-Strauss et al. (1999) Nucl Acids Res 27(5): 1323-1330; Kmiec (1999) Gene therapy American Scientist 87(3): 240-247).

The cell- or tissue-specific reduction in the activity of a subtilisin RNR9 can be effected for example by expressing a suitable construct, which, for example, an above-mentioned nucleic acid molecule, for example the antisense RNA, dsRNA, RNAi, ribozymes, with a suitable tissue-specific promoter, for example a promoter as described herein as being specific for epidermis or mesophyll.

For the purposes of the present invention, "mutations" means the modification of the nucleic acid sequence of a gene variant in a plasmid or in the genome of an organism. Mutations can arise for example as the result of errors in the replication, or they can be caused by mutagens. While the spontaneous mutation rate in the cell genome of organisms is very low, the skilled worker is familiar with a multiplicity of biological, chemical or physical mutagens.

Mutations comprise substitutions, additions, deletions of one or more nucleic acid residues. Substitutions are understood as meaning the exchange of individual nucleic acid bases; one distinguishes between transitions (substitution of a purine base for a purine base, or of a pyrimidine base for a pyrimidine base) and transversions (substitution of a pyrimidine base for a purine base (or vice versa)).

Additions or insertions are understood as meaning the incorporation of additional nucleic acid residues into the DNA, it being possible to result in reading-frame shifts. In the case of such reading-frame shifts, one distinguishes between "in-frame" insertions/additions and "out-of-frame" insertions. In the case of the "in-frame" insertions/additions, the reading frame is retained, and a polypeptide which is enlarged by the number of the amino acids encoded by the inserted nucleic acids results. In the case of "out-of-frame" insertions/additions, the original reading frame is lost, and the formation of a complete and functional polypeptide is no longer possible.

Deletions describe the loss of one or more base pairs, which likewise lead to "in-frame" or "out-of-frame" reading-frame shifts and the consequences which this entails regarding the formation of an intact protein.

The mutagenic agents (mutagens) which can be used for generating random or site-specific mutations, and the methods and techniques which can be applied, are known to the skilled worker. Such methods and mutagens are described for example in A. M. van Harten ((1998), Mutation breeding: theory and practical applications, Cambridge University Press, Cambridge, UK), E Friedberg, G Walker, W Siede ((1995), DNA Repair and Mutagenesis, Blackwell Publishing), or K. Sankaranarayanan, J. M. Gentile, L. R. Ferguson ((2000) Protocols in Mutagenesis, Elsevier Health Sciences).

Usual molecular-biological methods and processes, such as the in vitro mutagenesis kit, LA PCR in vitro Mutagenesis Kit (Takara Shuzo, Kyoto), or PCR mutagenesis using suitable primers may be employed for introducing site-specific mutations.

As has already been mentioned above, a multiplicity of chemical, physical and biological mutagens exists.

Those mentioned hereinbelow are given by way of example, but not by limitation.

Chemical mutagens can be distinguished by their mechanism of action. Thus, there are base analogs (for example 5-bromouracil, 2-aminopurine), mono- and bifunctional alkylating agents (for example monofunctional agents such as ethylmethylsulfonate, dimethyl sulfate, or bifunctional agents such as dichloroethyl sulfite, mitomycin, nitrosoguanidine-dialkylnitrosamine, N-nitrosoguanidine derivatives) or intercalating substances (for example acridine, ethidium bromide).

Physical mutagens are, for example, ionizing radiation. Ionizing radiation is electromagnetic waves or particle radiation capable of ionizing molecules, i.e. of removing electrons from the latter. The remaining ions are highly reactive in most cases, so that, if they are generated in live tissue, are capable of causing great damage, for example to the DNA, and (at low intensity) thereby inducing mutations. Ionizing radiation is, for example, gamma-radiation (photo energy of approximately one megaelectron volt (MeV)), X-rays (photo energy of a plurality of or many kiloelectron volts (keV)) or else ultraviolet light (UV light, photon energy of above 3.1 eV). UV light causes the formation of dimers between bases; with thymidine dimers, which give rise to mutations, being the most frequent here.

The traditional generation of mutants by treating the seeds with mutagenic agents such as, for example, ethylmethylsulfonate (EMS) (Birchler J A, Schwartz D. Biochem Genet. 1979 December; 17(11-12): 1173-80; Hoffmann G R. Mutat Res. 1980 January; 75(1): 63-129) or ionizing radiation has been joined by the use of biological mutagens, for example transposons (for example Tn5, Tn903, Tn916, Tn1000, Balcells et al., 1991, May B P et al. (2003) Proc Natl Acad Sci USA. September 30; 100 (20):11541-6) or molecular-biological methods such as the mutagenesis by means of T-DNA insertion (Feldman, K. A. Plant J. 1: 71-82. 1991, Koncz et al. (1992) Plant Mol Biol 20(5): 963-976).

The use of chemical or biological mutagens is preferred for the generation of mutated gene variants. In the case of chemical agents, the generation of mutants by application of EMS (ethylmethylsulfonate) mutagenesis is mentioned by particular preference. In the case of the generation of mutants using biological mutagenesis, the T-DNA mutagenesis or transposon mutagenesis may be mentioned by preference.

Thus, it is also possible to employ those polypeptides for the method according to the invention which are obtained as the result of a mutation of a polypeptide according to the invention, for example as shown in FIGS. 2, 4, 6, 8, 10, 12.

All substances and compounds which directly or indirectly bring about a reduction in the polypeptide quantity, RNA quantity, gene activity or polypeptide activity of a subtilisin RNR9 protein will hereinbelow be summarized under the term "anti-subtilisin RNR9 protein compounds". The term "anti-subtilisin RNR9 protein compound" explicitly includes the nucleic acid sequences, peptides, proteins or other factors which are employed in the above-described methods.

In a further preferred embodiment of the present invention, an increase in the resistance to pathogens from the families Blumeriaceae, Pucciniaceae, Mycosphaerellaceae and Hypocreaceae in a monocotyledonous or dicotyledonous plant or an organ, tissue or a cell thereof, is obtained by:

a) introduction, into a plant cell, of a recombinant expression cassette comprising an "anti-subtilisin RNR9 protein compound" in operable linkage with a promoter which is active in plants;
b) regeneration of the plant from the plant cell; and
c) expression of said "anti-subtilisin RNR9 protein compound" in a sufficient quantity and over a sufficiently long period to generate, or to increase, a pathogen resistance in said plant.

For example, regarding a nucleic acid sequence, an expression cassette or a vector comprising said nucleic acid sequence or an organism transformed with said nucleic acid sequence, expression cassette or vector, “transgenic” means all those constructs or organisms which are the result of recombinant methods and in which either a) the subtilisin RNR9 protein nucleic acid sequence, or b) a genetic control sequence which is operably linked with the subtilisin RNR9 protein nucleic acid sequence, for example a promoter, or c) (a) and (b)

are not in their natural genetic environment or have been modified by recombinant methods, it being possible for the modification to be for example a substitution, addition, deletion or insertion of one or more nucleotide residues. Natural genetic environment means the natural chromosomal locus in the original organism, or else the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, very especially preferably at least 5000 bp. A naturally occurring expression cassette—for example the naturally occurring combination of the subtilisin RNR9 protein promoter with the corresponding subtilisin RNR9 protein gene—becomes a transgenic expression cassette when the latter is modified by non-natural, synthetic (“artificial”) methods, such as, for example, treatment with a mutagen. Suitable methods are described in U.S. Pat. No. 5,565,350 and WO 00/15815.

For the purposes of the invention, “introduction” comprises all those methods which are suitable for introducing an “anti-subtilisin RNR9 protein compound” directly or indirectly into a plant or into a cell, compartment, tissue, organ or seeds thereof, or for generating such a compound therein. It comprises direct and indirect methods. The introduction can lead to a transient presence of one “anti-subtilisin RNR9 protein compound” (for example of a dsRNA) or else to a stable presence.

As the result of the differing nature of the above-described approaches, the “anti-subtilisin RNR9 protein compound” can exert its function directly (for example by insertion into an endogenous subtilisin RNR9 protein gene). However, the function can also be exerted indirectly after transcription into an RNA (for example in the case of antisense approaches) or after transcription and translation into a protein (for example in the case of binding factors). Both direct and indirectly acting are comprised in accordance with the invention.

“Introduction” comprises for example methods such as transfection, transduction or transformation.

Thus, “anti-subtilisin RNR9 protein compound” also comprises for example recombinant expression constructs which bring about an expression (i.e. transcription and, if appropriate, translation) of, for example, a subtilisin RNR9 protein dsRNA or a subtilisin RNR9 protein “antisense” RNA, preferably in a plant or in a part, tissue, organ or seed thereof.

In said expression constructs/expression cassettes, a nucleic acid molecule whose expression (transcription and, if appropriate, translation) generates an "anti-subtilisin RNR9 protein compound" is preferably in operable linkage with at least one genetic control element (for example a promoter) which ensures an expression in plants. If the expression construct is to be introduced directly into the plant and the "anti-subtilisin RNR9 protein compound" (for example the subtilisin RNR9 protein dsRNA) is to be generated therein in planta, plant-specific genetic control elements (for example promoters) are preferred. However, the "anti-subtilisin RNR9 protein compound" can also be generated in other organisms or in vitro and then be introduced into the plant. Here, all procaryotic or eucaryotic genetic control elements (for example promoters) which permit the expression in the respective plant which has been chosen for the generation are preferred.

An "operable" linkage is understood as meaning for example the sequential arrangement of a promoter with the nucleic acid sequence to be expressed (for example an "anti-subtilisin RNR9 protein compound") and, if appropriate, further regulatory elements such as, for example, a terminator in such a way that each of the regulatory elements is capable of fulfilling its function in the transgenic expression of the nucleic acid sequence, depending on the arrangement of the nucleic acid sequences to sense or antisense RNA. A direct linkage in the chemical sense is not necessarily required for this purpose. Genetic control sequences such as, for example, enhancer sequences, can also exert their function on the target sequence from positions which are further removed or else from other DNA molecules. Preferred arrangements are those in which the nucleic acid sequence to be expressed recombinantly is positioned behind the sequence which acts as promoter, so that the two sequences are bonded covalently with one another. In this context, the distance between the promoter sequence and nucleic acid sequence to be expressed recombinantly is preferably less than 200 base pairs, especially preferably less than 100 base pairs, very especially preferably less than 50 base pairs.

The preparation of a functional linkage and the preparation of an expression cassette can be accomplished by means of customary recombination and cloning techniques as are described for example in Maniatis T, Fritsch E F and Sambrook J ((1989) Molecular Cloning: A Laboratory Manual, Cold Spring Harbor Laboratory, Cold Spring Harbor (NY)), in Silhavy T J, Berman M L and Enquist L W ((1984) Experiments with Gene Fusions, Cold Spring Harbor Laboratory, Cold Spring Harbor (NY)), in Ausubel F M et al. ((1987) Current Protocols in Molecular Biology, Greene Publishing Assoc. and Wiley Interscience) and in Gelvin et al. ((1990) in: Plant Molecular Biology Manual). However, it is also possible to position further sequences which, for example, act as a linker with specific restriction enzyme cleavage sites or as a signal peptide between the two sequences. Moreover, the insertion of sequences can lead to the expression of fusion proteins. Preferably, the expression cassette consisting of a linkage of promoter and nucleic acid sequence to be expressed can be present in vector-integrated form and can be inserted into a plant genome, for example, by transformation.

However an expression cassette is also understood as meaning those constructs in which a promoter is placed behind an endogenous subtilisin RNR9 protein gene, for example by means of a homologous recombination, and where the expression of an antisense subtilisin RNR9 protein RNA brings about the reduction according to the invention of a subtilisin RNR9 protein. Analogously, an "anti-subtilisin RNR9 protein compound" (for example a nucleic acid sequence coding for a subtilisin RNR9 protein dsRNA or a subtilisin RNR9 protein antisense RNA) can be placed behind an endogenous promoter in such a way that the same effect occurs. Both approaches result in expression cassettes for the purposes of the invention.

Plant-specific promoters means in principle any promoter which is capable of controlling the expression of genes, in particular foreign genes, in plants or plant parts, plant cells, plant tissues, plant cultures. Here, the expression can be for example constitutional, inducible or development-dependent.

The following are preferred and thus given by way of example, but not by limitation
a) Constitutive promoters
   Preferred vectors are those which make possible a constitutive expression in plants (Benfey et al. (1989) EMBO J 8: 2195-2202). "Constitutive" promoter means those promoters which ensure expression in numerous, preferably all, tissues over a relatively large period of plant development, preferably at all times during plant development. In particular, a plant promoter or a promoter derived from a plant virus is preferably used. The promoter of the 35S transcript of the CaMV cauliflower mosaic virus (Franck et al. (1980) Cell 21: 285-294; Odell et al. (1985) Nature 313: 810-812; Shewmaker et al. (1985) Virology 140: 281-288; Gardner et al. (1986) Plant Mol Biol 6: 221-228) or the 19S CaMV Promoter (U.S. Pat. No. 5,352,605; WO 84/02913; Benfey et al. (1989) EMBO J 8: 2195-2202) is particularly preferred. A further suitable constitutive promoter is the rubisco small subunit (SSU) promoter (U.S. Pat. No. 4,962,028), the promoter of *agrobacterium* nopaline synthase, the TR double promoter, the *agrobacterium* OCS (octopine synthase) promoter, the ubiquitin promoter (Holtorf S et al. (1995) Plant Mol Biol 29: 637-649), the ubiquitin 1 promoter (Christensen et al. (1992) Plant Mol Biol 18: 675-689; Bruce et al. (1989) Proc Natl Acad Sci USA 86: 9692-9696), the Smas promoter, the cinnamyl-alcohol dehydrogenase promoter (U.S. Pat. No. 5,683,439), the promoters of vacuolar ATPase subunits or the promoter of a proline-rich protein from wheat (WO 91/13991), and further promoters of genes whose constitutive expression in plants is known to the skilled worker. Especially preferred as constitutive promoter is the promoter of nitrilase-1 (nit1) gene from *A. thaliana* (GENBANK® Accession No.: Y07648.2, Nukleotide 2456-4340, Hillebrand et al. (1996) Gene 170: 197-200).
b) Tissue-specific promoters
   One embodiment employs promoters with specificities for the anthers, ovaries, flowers, leaves, stems, roots and seeds.
   Seed-specific promoters such as, for example, the promoter of phaseolin (U.S. Pat. No. 5,504,200; Bustos M M et al. (1989) Plant Cell 1(9): 839-53), of the 2S albumin gene (Joseffson L G et al. (1987) J Biol Chem 262:12196-12201), of legumin (Shirsat A et al. (1989) Mol Gen Genet. 215(2): 326-331), of the USP (unknown seed protein; Baumlein H et al. (1991) Mol Gen Genet. 225(3): 459-67), of the napin gene (U.S. Pat. No. 5,608, 152; Stalberg K et al. (1996) L Planta 199: 515-519), of sucrose binding protein (WO 00/26388) or the legumin B4 promoter (LeB4; Baumlein H et al. (1991) Mol Gen Genet. 225: 121-128; Baeumlein et al. (1992) Plant Journal 2(2): 233-9; Fiedler U et al. (1995) Biotechnology (NY) 13(10): 1090f), the oleosin promoter from *arabidopsis* (WO 98/45461), the Bce4 promoter from *Brassica* (WO 91/13980). Further suitable seed-specific promoters are those of the genes coding for the high molecular weight glutenin (HMWG), gliadin, branching enzyme, ADP glucose pyrophosphatase (AGPase) or starch synthase. Further preferred promoters are those allowing seed-specific expression in monocotyledons such as maize, barley, wheat, rye, rice etc. It is possible and advantageous to employ the promoter of the Ipt2 or Ipt1 gene (WO 95/15389, WO 95/23230) or the promoters described in WO 99/16890 (promoters of the hordein gene, of the glutelin gene, of the oryzin gene, of the prolamin gene, of the gliadin gene, of the zein gene, of the kasirin gene or of the secalin gene).

Tuber-, storage root- or root-specific promoters, for example the patatin class I promoter (B33) or the promoter of the potato cathepsin D inhibitor.

Leaf-specific promoters, for example for example the promoter of the cytosolic FBPase from potato (WO 97/05900), the SSU promoter (small subunit) of the rubisco (ribulose-1,5-bisphosphate carboxylase) or the ST-LSI promoter from potato (Stockhaus et al. (1989) EMBO J. 8: 2445-2451). Epidermis-specific promoters, for example the promoter of the OXLP gene ("oxalate oxidase like protein"; Wei et al. (1998) Plant Mol. Biol. 36: 101-112).

Examples of other tissue-specific promoters are:

Flower-specific promoters for example the phytoen-synthase promoter (WO 92/16635) or the promoter of the P-rr gene (WO 98/22593).

Anther-specific promoters for example the 5126 promoter (U.S. Pat. No. 5,689,049, U.S. Pat. No. 5,689,051), the glob-I promoter and the alpha-zein promoter.

Or the abovementioned epidermis- or mesophyll-specific promoters which are especially preferred.

In one embodiment, the activity of RNR9, in particular of HvRNR9, in particular of the RNR9 as described herein, is lowered, blocked or prevented in the epidermis, in particular for increasing the resistance to mildew, for example by means of gene silencing, for example by means of an RNAi, antisense, cosuppression or microRNA approach as can be carried out by the skilled worker on the basis of the methods and sequences disclosed herein.

In one embodiment, the activity of RNR9, in particular of HvRNR9, in particular of RNR9 as described herein, is lowered, blocked or prevented in the mesophyll, in particular for increasing the resistance to Septoria and rusts, for example by means of gene silencing, for example by means of an RNAi, antisense, cosuppression or microRNA approach as can be carried out by the skilled worker on the basis of the methods and sequences disclosed herein.

c) Chemically inducible promoters

The expression cassettes may also comprise a chemically inducible promoter (review article: Gatz et al. (1997) Annu. Rev. Plant Physiol Plant Mol Biol 48: 89-108) through which expression of the exogenous gene in the plant can be controlled at a particular point in time. Promoters of this type, such as, for example, the PRP1 promoter (Ward et al. (1993) Plant Mol Biol 22: 361-366), a salicylic acid-inducible promoter (WO 95/19443), a benzenesulfonamide-inducible promoter (EP 0 388 186), a tetracycline-inducible promoter (Gatz et al. (1992) Plant J 2: 397-404), an abscisic acid-inducible promoter (EP 0 335 528) and an ethanol or cyclohexanone-inducible promoter (WO 93/21334) can likewise be used. Thus, for example, the expression of a molecule which reduces or inhibits the subtilisin RNR9 protein function, such as, for example, the dsRNA, ribozymes, antisense nucleic acid molecules and the like which have been listed above can be induced at suitable points in time.

d) Stress- or pathogen-inducible promoters

Very especially advantageous is the use of inducible promoters for expressing the RNAi constructs employed for reducing the callose synthase polypeptide quantity, activity or function, which, for example, when pathogen-inducible promoters are used, makes possible an expression only when required, (i.e. in the case of attack by pathogens).

In one embodiment, the method according to the invention therefore uses promoters which are active in plants which are pathogen-inducible promoters.

Pathogen-inducible promoters comprise the promoters of genes which are induced as a result of pathogen attack, such as, for example, genes of PR proteins, SAR proteins, β-1,3-glucanase, chitinase etc. (for example Redolfi et al. (1983) Neth J Plant Pathol 89: 245-254; Uknes, et al. (1992) Plant Cell 4: 645-656; Van Loon (1985) Plant Mol Viral 4: 111-116; Marineau et al. (1987) Plant Mol Biol 9: 335-342; Matton et al. (1987) Molecular Plant-Microbe Interactions 2: 325-342; Somsich et al. (1986) Proc Natl Acad Sci USA 83: 2427-2430; Somsich et al. (1988) Mol Gen Genetics 2: 93-98; Chen et al. (1996) Plant J 10: 955-966; Zhang and Sing (1994) Proc Natl Acad Sci USA 91: 2507-2511; Warner, et al. (1993) Plant J 3: 191-201; Siebertz et al. (1989) Plant Cell 1: 961-968 (1989)).

Also comprised are wound-inducible promoters such as that of the pinII gene (Ryan (1990) Ann Rev Phytopath 28: 425-449; Duan et al. (1996) Nat Biotech 14: 494-498), of the wun1 and wun2 gene (U.S. Pat. No. 5,428,148), of the win1 and win2 gene (Stanford et al. (1989) Mol Gen Genet. 215: 200-208), of the systemin gene (McGurl et al. (1992) Science 225: 1570-1573), of the WIP1 gene (Rohmeier et al. (1993) Plant Mol Biol 22: 783-792; Eckelkamp et al. (1993) FEBS Letters 323: 73-76), of the MPI gene (Corderok et al. (1994) Plant J 6(2): 141-150) and the like.

A source of further pathogen-inducible promoters is the PR gene family. A series of elements in these promoters have proved advantageous. Thus, the region −364 to −288 in the promoter of PR-2d mediates salicylate specificity (Buchel et al. (1996) Plant Mol Biol 30, 493-504). The sequence 5'-TCATCTTCTT-3' occurs repeatedly in the promoter of the barley beta 1,3-glucanase and in more than 30 other stress-induced genes. In tobacco, this region binds a nuclear protein whose abundance is increased by salicylate. The PR-1 promoters from tobacco and *Arabidopsis* (EP-A 0 332 104, WO 98/03536) are also suitable as pathogen-inducible promoters. Preferred, since particularly specifically induced by pathogens, are the "acidic PR-5"-(aPR5) promoters from barley (Schweizer et al. (1997) Plant Physiol 114: 79-88) and wheat (Rebmann et al. (1991) Plant Mol Biol 16:329-331). aPR5 proteins accumulate within approximately 4 to 6 hours after attack by pathogens and only show very little background expression (WO 99/66057). One approach for obtaining an increased pathogen-induced specificity is the generation of synthetic promoters from combinations of known pathogen-responsive elements (Rushton et al. (2002) Plant Cell 14, 749-762; WO 00/01830; WO 99/66057).

Other pathogen-inducible promoters from different species are known to the skilled worker (EP-A 1 165 794; EP-A 1 062 356; EP-A 1 041 148; EP-A 1 032 684).

Further pathogen-inducible promoters comprise the Flachs Fis1 promoter (WO 96/34949), the Vst1 promoter (Schubert et al. (1997) Plant Mol Biol 34: 417-426) and the tobacco EAS4 sesquiterpene cyclase promoter (U.S. Pat. No. 6,100,451).

Other preferred promoters are those which are induced by biotic or abiotic stress, such as, for example, the pathogen-inducible promoter of the PRP1 gene (or gst1 promoter), for example from potato (WO 96/28561; Ward et al. (1993) Plant Mol Biol 22: 361-366), the heat-inducible hsp70 or hsp80 promoter from tomato (U.S. Pat. No. 5,187,267), the chill-inducible alpha-amylase promoter from potato (WO 96/12814), the light-inducible PPDK promoter or the wounding-inducible pinII promoter (EP-A 0 375 091).

e) Mesophyll-tissue-specific promoters

In one embodiment, the method according to the invention employs mesophyll-tissue-specific promoters such as, for example, the promoter of the wheat germin 9f-3.8 gene (GENBANK® Accession No.: M63224) or the barley GerA promoter (WO 02/057412). Said promoters are particularly advantageous since they are both mesophyll-tissue-specific and pathogen-inducible. Also suitable is the mesophyll-tissue-specific *Arabidopsis* CAB-2 promoter (GENBANK® Accession No.: X15222), and the *Zea mays* PPCZm1 promoter (GENBANK® Accession No.: X63869) or homologs thereof. Mesophyll-tissue-specific means that the transcription of a gene is limited to as few as possible plant tissues which comprise the mesophyll tissue as the result of the specific interaction of cis elements present in the promoter sequence and transcription factors binding to these elements; preferably, it means a transcription which is limited to the mesophyll tissue.

As regards further promoters which are expressed essentially in the mesophyll or in the epidermis, see the enumeration inserted further above.

f) Development-dependent promoters

Examples of further suitable promoters are fruit ripening-specific promoters such as, for example, the fruit ripening-specific promoter from tomato (WO 94/21794, EP 409 625). Development-dependent promoters include some of the tissue-specific promoters because the development of individual tissues naturally takes place in a development-dependent manner.

Constitutive, and leaf- and/or stem-specific, pathogen-inducible, root-specific, mesophyll-tissue-specific promoters are particularly preferred, with constitutive, pathogen-inducible, mesophyll-tissue-specific and root-specific promoters being most preferred.

A further possibility is for further promoters which make expression possible in further plant tissues or in other organisms such as, for example, *E. coli* bacteria to be operably linked to the nucleic acid sequence to be expressed. All the promoters described above are in principle suitable as plant promoters.

Other promoters which are suitable for expression in plants are described in Rogers et al. ((1987) Meth in Enzymol 153: 253-277), Schardl et al. ((1987) Gene 61: 1-11) or Berger et al. ((1989) Proc Natl Acad Sci USA 86: 8402-8406)).

The nucleic acid sequences present in the expression cassettes or vectors of the invention may be operably linked to further genetic control sequences besides a promoter. The term genetic control sequences has a wide meaning and means all sequences which have an influence on the coming into existence or the function of the expression cassette of the invention. For example, genetic control sequences modify transcription and translation in prokaryotic or eukaryotic organisms. The expression cassettes of the invention preferably comprise a promoter with an abovementioned specificity 5'-upstream from the particular nucleic acid sequence which is to be expressed transgenically, and a terminator sequence as additional genetic control sequence 3'-downstream, and if appropriate further conventional regulatory elements, in each case operably linked to the nucleic acid sequence to be expressed transgenically.

Genetic control sequences also comprise further promoters, promoter elements or minimal promoters capable of modifying the expression-controlling properties. It is thus possible for example through genetic control sequences for tissue-specific expression to take place additionally dependent on particular stress factors. Corresponding elements are described for example for water stress, abscisic acid (Lam E and Chua N H, J Biol Chem 1991; 266(26): 17131-17135) and heat stress (Schoffl F et al., Molecular & General Genetics 217(2-3): 246-53, 1989).

It is possible in principle for all natural promoters with their regulatory sequences like those mentioned above to be used for the method of the invention. It is additionally possible also for synthetic promoters to be used advantageously.

Genetic control sequences further comprise also the 5'-untranslated regions, introns or noncoding 3' region of genes such as, for example, the actin-1 intron, or the Adh1-S introns 1, 2 and 6 (generally: The Maize Handbook, Chapter 116, Freeling and Walbot, Eds., Springer, New York (1994)). It has been shown that these may play a significant function in the regulation of gene expression. It has thus been shown that 5'-untranslated sequences are capable of enhancing transient expression of heterologous genes. An example of a translation enhancer which may be mentioned is the 5' leader sequence from the tobacco mosaic virus (Gallie et al. (1987) Nucl Acids Res 15: 8693-8711) and the like. They may in addition promote tissue specificity (Rouster J et al. (1998) Plant J 15: 435-440).

The expression cassette may advantageously comprise one or more so-called enhancer sequences in operable linkage with the promoter, which make increased transgenic expression of the nucleic acid sequence possible. Additional advantageous sequences such as further regulatory elements or terminators can also be inserted at the 3' end of the nucleic acid sequences to be expressed recombinantly. The nucleic acid sequences to be expressed recombinantly may be present in one or more copies in the gene construct.

Polyadenylation signals suitable as control sequences are plant polyadenylation signals, preferably those which correspond essentially to T-DNA polyadenylation signals from *Agrobacterium tumefaciens*, in particular to gene 3 of the T-DNA (octopine-synthase) of the Ti plasmid pTiACHS (Gielen et al. (1984) EMBO J. 3: 835 ff) or functional equivalents thereof. Examples of particularly suitable terminator sequences are the OCS (octopine-synthase) terminator and the NOS (nopaline-synthase) terminator.

Control sequences additionally mean those which make homologous recombination or insertion into the genome of a host organism possible or allow deletion from the genome. In homologous recombination, for example, the natural promoter of a particular gene can be specifically replaced by a promoter with specificity for the embryonal epidermis and/or the flower.

An expression cassette and/or the vectors derived from it may comprise further functional elements. The term functional element has a wide meaning and means all elements which have an influence on the production, replication or function of the expression cassettes, the vectors or the transgenic organisms of the invention. Non-restrictive examples which may be mentioned are:

a) Selection markers which confer a resistance to a metabolism inhibitor such as 2-deoxyglucose 6-phosphate (WO 98/45456), antibiotics or biozides, preferably herbicides, for example kanamycin, G 418, bleomycin, hygromycin or phosphinotricin and the like. Especially preferred selection markers are those which confer a resistance to herbicides. DNA sequences which code for phosphinothricin acetyl-transferases (PAT), which inactivate glutamine-synthase-inhibitors (bar and pat gene), 5-enolpyruvylshikimate-3-phosphate-synthase (EPSP-synthase genes) which confer resistance to Glyphosat® (N-(phosphonomethyl)glycine), the gox gene, which codes for the Glyphosat®-degrading enzyme (glyphosate-oxidoreductase), the deh gene (coding for a dehalogenase which inactivates dalapon), sulfo-nylurea- and imidazolinone-inactivating acetolactate-synthases and bxn genes which code for bromoxynil-degrading nitrilase enzymes, the aasa gene, which confers a resistance to the antibiotic apectinomycin, the streptomycin-phosphotransferase (SPT) gene, which makes possible a resistance to streptomycin, the neomycin-phosphotransferase (NPTII) gene, which confers a resistance to kanamycin or geneticidin, the hygromycin-phosphotransferase (HPT) gene, which mediates a resistance to hygromycin, the acetolactate-synthase gene (ALS), which mediates a resistance to sulfonylurea herbicides (for example mutated ALS variants with, for example, the S4 and/or Hra mutation).

b) Reporter genes which code for easily quantifiable proteins and ensure via an intrinsic color or enzymic activity an assessment of the transformation efficiency or of the location or timing of expression. Very particular preference is given in this connection to reporter proteins (Schenborn E, Groskreutz D. Mol. Biotechnol. 1999; 13(1): 29-44) such as the green fluorescence protein (GFP) (Sheen et al. (1995) Plant Journal 8(5): 777-784; Haselhoff et al. (1997) Proc Natl Acad Sci USA 94(6): 2122-2127; Reichel et al. (1996) Proc Natl Acad Sci USA 93(12): 5888-5893; Tian et al. (1997) Plant Cell Rep 16: 267-271; WO 97/41228; Chui W L et al. (1996) Curr Biol 6:325-330; Leffel S M et al. (1997) Biotechniques. 23(5): 912-8), the chloramphenicoltransferase, a luciferase (Ow et al. (1986) Science 234: 856-859; Millar et al. (1992) Plant Mol Biol Rep 10: 324-414), the aequorin gene (Prasher et al. (1985) Biochem Biophys Res Commun 126(3): 1259-1268), the β-galactosidase, R-locus gene (code for a protein which regulates the production of anthocyanin pigments (red coloration) in plant tissue and thus makes possible the direct analysis of the promoter activity without the addition of additional adjuvants or chromogenic substrates; Dellaporta et al., In: Chromosome Structure and Function: Impact of New Concepts, 18th Stadler Genetics Symposium, 11: 263-282, (1988), with β-glucuronidase being very especially preferred (Jefferson et al., EMBO J. 1987, 6, 3901-3907).

c) Origins of replication which ensure replication of the expression cassettes or vectors of the invention in, for example, E. coli. Examples which may be mentioned are ORI (origin of DNA replication), the pBR322 ori or the P15A ori (Sambrook et al.: Molecular Cloning. A Laboratory Manual, $2^{nd}$ ed. Cold Spring Harbor Laboratory Press, Cold Spring Harbor, N.Y., 1989).

d) Elements which are necessary for *agrobacterium*-mediated plant transformation, such as, for example, the right or left border of the T-DNA or the vir-region.

To select successfully transformed cells, it is generally required additionally to introduce a selectable marker which confers to the successfully transformed cells a resistance to a biocide (for example a herbicide), a metabolism inhibitor such as 2-deoxyglucose 6-phosphate (WO 98/45456) or an antibiotic. The selection marker permits the selection of the transformed cells from untransformed cells (McCormick et al. (1986) Plant Cell Reports 5: 81-84).

The introduction of an expression cassette according to the invention into an organism or into cells, tissues, organs, parts or seeds thereof (preferably into plants or plant cells, tissues, organs, parts or seeds) can advantageously be accomplished using vectors in which the expression cassettes are present. The expression cassette can be introduced into the vector (for example a plasmid) via a suitable restriction cleavage site. The resulting plasmid is first introduced into E. coli. Correctly transformed E. coli are selected, cultured, and the recombinant plasmid is obtained using methods known to the skilled worker. Restriction analysis and sequencing can be used for verifying the cloning step.

Examples of vectors can be plasmids, cosmids, phages, viruses or else *agrobacteria*. In an advantageous embodiment, the introduction of the expression cassette is accomplished by means of plasmid vectors. Preferred vectors are those which make possible a stable integration of the expression cassette into the host genome.

The generation of a transformed organism (or a transformed cell) requires the introduction of suitable DNA molecules, and thus of the RNA molecules or proteins formed as the result of their gene expression, into the host cell in question.

A multiplicity of methods (Keown et al. (1990) Methods in Enzymology 185: 527-537) is available for this procedure, which is referred to as transformation (or transduction or transfection). Thus, DNA or RNA can be introduced for example directly by means of microinjection or by bombardment with DNA-coated microparticles. Also, it is possible to permeabilize the cell chemically, for example with polyethylene glycol, so that the DNA can enter the cell by diffusion. Alternatively, the DNA can be introduced by protoplast fusion with other DNA-comprising units such as minicells, cells, lysosomes or liposomes. Another suitable method for introducing DNA is electroporation, where the cells are reversibly permeabilized by means of an electrical pulse. Suitable methods are described (for example in Bilang et al. (1991) Gene 100: 247-250; Scheid et al. (1991) Mol Gen Genet. 228: 104-112; Guerche et al. (1987) Plant Science 52: 111-116; Neuhause et al. (1987) Theor Appl Genet. 75: 30-36; Klein et al. (1987) Nature 327: 70-73; Howell et al. (1980) Science 208:1265; Horsch et al. (1985) Science 227: 1229-1231; DeBlock et al. (1989) Plant Physiology 91: 694-701; Methods for Plant Molecular Biology (Weissbach and Weissbach, eds.) Academic Press Inc. (1988); and Methods in Plant Molecular Biology (Schuler and Zielinski, eds.) Academic Press Inc. (1989)).

In plants, the described methods for the transformation and regeneration of plants from plant tissues or plant cells for the transient or stable transformation are used. Suitable methods are mainly the transformation of protoplasts by means of polyethylene-glycol-induced DNA uptake, the biolistic method with the gene gun, the so-called particle bombardment method, electroporation, the incubation of dry embryos in DNA-comprising solution, and Microinjection.

In addition to these "direct" transformation techniques, a transformation can also be carried out by bacterial infection by means of *Agrobacterium tumefaciens* or *Agrobacterium rhizogenes*. The methods are described for example in Horsch R B et al. (1985) Science 225: 1229f.

If *agrobacteria* are used, the expression cassette is to be integrated into specific plasmids, either into a shuttle or intermediate vector or into a binary vector. If a Ti or Ri plasmid is used for the transformation, at least the right border, but in most cases the right and the left border, of the Ti or Ri plasmid T-DNA is linked as flanking region with the expression cassette to be introduced.

It is preferred to use binary vectors. Binary vectors are capable of replicating both in *E. coli* and in *Agrobacterium*. As a rule, they comprise a selection marker gene and a linker or polylinker flanked by the right and left T-DNA border sequence. They can be transformed directly into *Agrobacterium* (Holsters et al. (1978) Mol Gen Genet. 163: 181-187). The selection marker gene permits a selection of transformed *agrobacteria* and is, for example, the nptII gene, which confers a resistance to kanamycin. The *agrobacterium* which acts as host organism in this case should already comprise a plasmid with the vir region. This is required for transferring the T-DNA to the plant cell. An *agrobacterium* thus transformed can be used for the transformation of plant cells. The use of T-DNA for the transformation of plant cells has been studied and described extensively (EP 120 516; Hoekema, in: The Binary Plant Vector System, Offsetdrukkerij Kanters B. V., Alblasserdam, Chapter V; An et al. (1985) EMBO J. 4: 277-287). Various binary vectors are known and in some cases commercially available, such as, for example, pBI101.2 or pBIN19 (Clonetech Laboratories, Inc. USA).

In the case of the injection or electroporation of DNA or RNA into plant cells, the plasmid used need not meet any particular requirements. Simple plasmids such as those from the pUC series can be used. If intact plants are to be regenerated from the transformed cells, it is necessary for an additional selectable marker gene to be located on the plasmid.

Stably transformed cells, i.e. those which comprise the introduced DNA integrated into the DNA of the host cell, can be selected from untransformed cells when a selectable marker is a component of the introduced DNA. For example, any gene which is capable of conferring a resistance to antibiotics or herbicides (such as kanamycin, G 418, bleomycin, hygromycin or phosphinothricin and the like) can act as marker (see hereinabove). Transformed cells which express such a marker gene are capable of surviving in the presence of concentrations of a suitable antibiotic or herbicide which kill an untransformed wild type. Examples are mentioned above and preferably comprise the bar gene, which confers resistance to the herbicide phosphinothricin (Rathore K S et al. (1993) Plant Mol Biol 21(5): 871-884), the nptII gene, which confers resistance to kanamycin, the hpt gene, which confers resistance to hygromycin, or the EPSP gene, which confers resistance to the herbicide glyphosate. The selection marker permits the selection of transformed cells from untransformed cells (McCormick et al. (1986) Plant Cell Reports 5: 81-84). The plants obtained can be bred and hybridized in the customary manner. Two or more generations should be grown in order to ensure that the genomic integration is stable and hereditary.

The abovementioned methods are described for example in Jenes B et al. (1993) Techniques for Gene Transfer, in: Transgenic Plants, Vol. 1, Engineering and Utilization, edited by S D Kung and R Wu, Academic Press, p. 128-143 and in Potrykus (1991) Annu Rev Plant Physiol Plant Molec Biol 42: 205-225). The construct to be expressed is preferably cloned into a vector which is suitable for transforming *Agrobacterium tumefaciens*, for example pBin19 (Bevan et al. (1984) Nucl Acids Res 12: 8711f).

As soon as a transformed plant cell has been generated, an intact plant can be obtained using methods known to the skilled worker. Here, the starting material is, for example, callus cultures. The development of shoot and root can be induced in the known manner from these as yet undifferentiated cell lumps. The plantlets obtained can be potted on and bred.

The skilled worker is also familiar with methods of regenerating plant parts and intact plants from plant cells. For example, methods described by Fennell et al. (1992) Plant Cell Rep. 11: 567-570; Stoeger et al (1995) Plant Cell Rep. 14:273-278; Jahne et al. (1994) Theor Appl Genet. 89:525-533 are used for this purpose.

The method according to the invention can advantageously be combined with other methods which bring about a pathogen resistance (for example to insects, fungi, bacteria, nematodes and the like), stress resistance or another improvement of the plant's characteristics. Examples are mentioned inter alia in Dunwell J M, Transgenic approaches to crop improvement, J Exp Bot. 2000; 51 Spec No; pages 487-96.

In a preferred embodiment, the reduction of the function of a subtilisin RNR9 protein in a plant is accomplished in combination with an increase in the activity of a Bax inhibitor 1 protein. This can be effected for example by expressing a nucleic acid sequence which codes for a Bax inhibitor 1 protein, for example in the mesophyll tissue and/or root tissue.

In the method according to the invention, the Bax inhibitor 1 proteins from *Hordeum vulgare* or *Nicotiana tabacum* are especially preferred.

Another subject matter of the invention relates to nucleic acid molecules which comprise nucleic acid molecules coding for subtilisin RNR9 proteins from wheat and barley as shown in FIGS. 1 and 3, and to the nucleic acid sequences which are complementary thereto, and to the sequences derived as the result of the degeneracy (degeneration) of the genetic code and to the nucleic acid molecules which code for functional equivalents of the polypeptides as shown in FIGS. 1 and 3 which do not consist of the sequences as shown in FIG. 5, 7, 9 or 11.

Another subject matter of the invention relates to the subtilisin RNR9 proteins from wheat and barley as shown in FIGS. 2 and 4 or to one which comprises these sequences, and to functional equivalents thereof, which do not consist of the sequences as shown in FIG. 6, 8, 10 or 12.

Another subject matter of the invention relates to doublestranded RNA nucleic acid molecules (dsRNA molecule) which, when introduced into a plant (or into a cell, tissue, organ or seed thereof), bring about the reduction of a subtilisin RNR9 protein, where the sense strand of said dsRNA molecule has at least 30%, preferably at least 40%, 50%, 60%, 70%, 75%, 80%, 85% or 90%, especially preferably at least 95%, very especially preferably 100%, homology with a nucleic acid molecule as shown in FIG. 1, 3, 5, 7, 9 or 11, or to a fragment of at least 17 base pairs, preferably at least 18, 19, 20, 21, 22, 23, 24, 25, 26, 27, 28, 29 or 30 base pairs, especially preferably at least 35, 40, 50, 60, 70, 80 or 90 base pairs, very especially preferably at least 100, 200, 300 or 400 base pairs, most preferably at least 500, 600, 700, 800, 900, at least 1000, base pairs and which has at least 50%, 60%, 70% or 80%, especially preferably at least 90%, very especially preferably 100%, homology with a nucleic acid molecule as shown in FIG. 1, 3, 5, 7, 9 or 11.

The double-stranded structure can be formed starting from a single, autocomplementary strand or starting from two complementary strands. In an especially preferred embodiment, sense and antisense sequence are linked by a linking sequence (linker) and can form for example a hairpin structure. The linking sequence can very especially preferably be an intron, which is spliced out after the dsRNA has been synthesized.

The nucleic acid sequence coding for a dsRNA can comprise further elements, such as, for example, transcription termination signals or polyadenylation signals.

A further subject matter of the invention relates to transgenic expression cassettes which comprise one of the nucleic acid sequences according to the invention. In the transgenic expression cassettes according to the invention, the nucleic acid sequence coding for the subtilisin RNR9 proteins from barley, wheat and maize is linked with at least one genetic control element as defined above in such a manner that the expression (transcription and, if appropriate, translation) can be accomplished in a desired organism, preferably monocotyledonous plants. Genetic control elements which are suitable for this purpose are described above. The transgenic expression cassettes can also comprise further functional elements as defined above.

Such expression cassettes comprise for example a nucleic acid sequence according to the invention, for example one which is essentially identical to a nucleic acid molecule as shown in FIG. 1, 3, 5, 7, 9 or 11, or a fragment thereof according to the invention, where said nucleic acid sequence is preferably arranged in sense orientation or in antisense orientation relative to a promoter and can therefore lead to the expression of sense or antisense RNA, where said promoter is a promoter which is active in plants, preferably a promoter which is inducible by pathogen attack. Also comprised according to the invention are transgenic vectors which comprise said transgenic expression cassettes.

Another subject matter of the invention relates to plants which, as the result of natural processes or of artificial induction, comprise one or more mutations in a nucleic acid molecule which comprises the nucleic acid sequence as shown in FIG. 1, 3, 5, 7, 9 or 11, where said mutation brings about a reduction in the activity, function or polypeptide quantity of a polypeptide encoded by the nucleic acid molecules as shown in FIG. 1, 3, 5, 7, 9 or 11. For example a mutation prepared and identified by tilling.

Preferred in this context are plants which belong to the family Poaceae, especially preferred are plants selected among the plant genera *Hordeum, Avena, Secale, Triticum, Sorghum, Zea, Saccharum* and *Oryza*, very especially preferably plants selected from the species *Hordeum vulgare* (barley), *Triticum aestivum* (wheat), *Triticum aestivum* subsp. *spelta* (spelt), Triticale, *Avena sativa* (oats), *Secale cereale* (rye), *Sorghum bicolor* (sorghum), *Zea mays* (maize), *Saccharum officinarum* (sugar cane) and *Oryza sativa* (rice).

One embodiment of the invention therefore relates to a monocotyledonous organism comprising a nucleic acid sequence according to the invention which comprises a mutation which brings about, in the organisms or parts thereof, a reduction in the activity of one of the proteins encoded by the nucleic acid molecules according to the invention. For example, the mutation relates to one or more amino acid residues which are identified as being conserved or highly conserved in the consensus sequence shown in FIG. 13 or 14.

In accordance with the invention, subtilisin RNR9 of different organisms, in particular of plants, especially preferably of useful plants, in particular of subtilisin of the plant genera *Hordeum, Avena, Secale, Triticum, Sorghum, Zea, Saccharum* and *Oryza* and also *Arabidopsis* generally have a so-called consensus region. FIG. 16 shows a so-called sequence alignment of different subtilisin RNR9 sequences with subtilisin RNR9 from wheat and *Arabidopsis thalina*. The color-code used in the sequence alignment mean the following:

(a) red against yellow background: all positions identical (therefore also identical to the consensus)
(b) dark blue against light blue background: this position in this sequence is identical to the consensus
(c) black against green: this position in this sequence shows strong similarity with the consensus (see hereinbelow)
(d) green against white: this position in this sequence shows weak similarity with the consensus (see hereinbelow)
(e) black against white background: this position in this sequence differs from the consensus Strong and weak similarity are allocated in accordance with the table which follows (residue consensus):

| Residue | Strong (c) | Weak (d) |
|---------|-----------|----------|
| A | G, S | C, T, V |
| C |  | A, S |
| D | E | G, H, K, N, Q, R, S |
| E | D | H, K, N, Q, R, S |
| F | W, Y | H, I, L, M |
| G | A | D, N, S |
| H | Y | D, E, F, K, N, Q, R |
| I | L, M, V | F |
| K | R | D, E, H, N, Q, S, T |
| L | I, M, V | F |
| M | I, L, V | F |
| N | Q | D, E, G, H, K, R, S, T |
| P |  | S, T |
| Q | N | D, E, H, K, R, S |
| R | K | D, E, H, N, Q |
| S | A, T | C, D, E, G, K, N, P, Q |
| T | S | A, K, N, P, V |
| V | I, L, M | A, T |
| W | F, Y |  |
| Y | F, H, W |  |

The consensus sequence derived therefrom which can be assumed to be decisive for the physiological function of the different subtilisin RNR9s is shown in FIG. 14, where X can be one or more of any amino acids, with X preferably being any 1, 2 or 3 amino acids, with X more preferably being any one amino acid (see FIG. 2, 4, 6, 8, 10 or 12). The underlined amino acids were identified as being conserved in all compared sequences.

The preferred consensus sequence is shown in FIG. 13, where X can be any one or more amino acids, with X preferably being any 1, 2 or 3 amino acids, with X more preferably being any one amino acid (see FIG. 2, 4, 6, 8, 10 or 12).

The present invention therefore also relates to nucleic acid sequences which code for the above-shown consensus sequences shown in FIG. 14, preferably shown in FIG. 13, and to their use in the methods according to the invention for the generation of transgenic plants with an increased pathogen resistance by reducing the content and/or the activity of at least one subtilisin RNR9. In this context, the consensus sequence shown is preferably characteristic of subtilisin RNR9 from barley and preferably also for subtilisin RNR9 from other plants.

Moreover, each amino acid identified in the consensus sequences according to FIG. 13 or 14 can be exchanged by any of the corresponding amino acids according to the table on page 62. Hence, the usage of the alternative amino acids identified with "Strong (c)" or "Weak (d)" in said table enables a person skilled in the art to generate sequences also comprised by the present invention showing stronger or weaker similarity on the level of amino acid properties with the sequences depicted in FIG. 13, 14 or 16.

Accordingly, another subject matter of the invention relates to transgenic plants, transformed with at least one nucleic acid sequence, which comprises the nucleic acid molecules as shown in FIG. 1, 3, 5, 7, 9 or 11, or the nucleic acid sequences complementary thereto, and the nucleic acid molecules which code for functional equivalents of the polypeptides as shown in FIG. 2, 4, 6, 8, 10 or 12;
one double-stranded RNA nucleic acid molecule (dsRNA molecule) which brings about the reduction of a subtilisin RNR9 protein, where the sense strand of said dsRNA molecule has at least 30%, preferably at least 40%, 50%, 60%, 70%, 75%, 80%, 85% or 90%, especially preferably at least 95%, very especially preferably 100%, homology with a nucleic acid molecule as shown in FIG. 1, 3, 5, 7, 9 or 11, or a fragment of at least 17 base pairs, preferably at least 18, 19, 20, 21, 22, 23, 24, 25, 26, 27, 28, 29 or 30 base pairs, especially preferably at least 35, 40, 50, 60, 70, 80 or 90 base pairs, very especially preferably at least 100, 200, 300 or 400 base pairs, most preferably at least 500, 600, 700, 800, 900 or more base pairs, which has at least 50%, 60%, 70%, 75%, 80%, 85% or 90%, especially preferably at least 95%, very especially preferably 100%, homology with a nucleic acid molecule as shown in FIG. 1, 3, 5, 7, 9 or 11;
one transgenic expression cassette which comprises one of the nucleic acid sequences according to the invention, or a vector according to the invention, and cells, cell cultures, tissues, parts—such as, for example in the case of plant organisms, leaves, roots and the like—or propagation material derived from such organisms;
where in one embodiment the nucleic acid molecules do not consist of the nucleic acid molecules as shown in FIG. 1, 3, 5, 7, 9 or 11, and in one embodiment do not consist of the polypeptide molecules as shown in FIG. 2, 4, 6, 8, 10 or 12.

In one embodiment, the plant according to the invention or the plant used in accordance with the invention is not *Arabidopsis thaliana*.

Host or starting organisms which are preferred as "transgenic organisms" are mainly plants in accordance with the above definition. In one embodiment, the transgenic organism is a mature plant, seed, shoot and seedling, and parts, propagation material and cultures derived therefrom, for example cell cultures. "Mature plants" means plants at any desired developmental stage beyond the seedling. "Seedling" means a young immature plant in an early developmental stage. Plants which are especially preferred as host organisms are plants to which the method according to the invention of obtaining a pathogen resistance in accordance with above-mentioned criteria can be applied. In one embodiment, the plant is a monocotyledonous plant such as, for example, wheat, oats, sorghum and millet, barley, rye, maize, rice, buckwheat, sorghum, triticale, spelt or sugar cane, in particular selected from the species *Hordeum vulgare* (barley), *Triticum aestivum* (wheat), *Triticum aestivum* subsp. *spelta* (spelt), Triticale, *Avena sativa* (oats), *Secale cereale* (rye), *Sorghum bicolor* (sorghum), *Zea mays* (maize), *Saccharum officinarum* (sugar cane) and *Oryza sativa* (rice).

The generation of the transgenic organisms can be accomplished with the above-described methods for the transformation or transfection of organisms.

Another subject matter of the invention relates to the transgenic plants described in accordance with the invention which additionally have an increased Bax inhibitor 1 activity, with plants which have an increased Bax inhibitor 1 activity in mesophyll cells or root cells being preferred, with transgenic plants which belong to the family Poaceae and which have an increased Bax inhibitor 1 activity in mesophyll cells or root cells being especially preferred, with transgenic plants selected among the plant genera *Hordeum, Avena, Secale, Triticum, Sorghum, Zea, Saccharum* and *Oryza* being even more preferred, and with the plant species *Hordeum vulgare* (barley), *Triticum aestivum* (wheat), *Triticum aestivum* subsp. *spelta* (spelt), Triticale, *Avena sativa* (oats), *Secale cereale* (rye), *Sorghum bicolor* (sorghum), *Zea mays* (maize), *Saccharum officinarum* (sugar cane) and *Oryza sativa* (rice) being preferred most of all.

Another subject matter of the invention relates to the use of the transgenic organisms according to the invention and of the cells, cell cultures, parts—such as, for example in the case of transgenic plant organisms, roots, leaves and the like—and transgenic propagation material such as seeds or fruits derived therefrom for the preparation of foodstuffs or feedstuffs, pharmaceuticals or fine chemicals.

In one embodiment, the invention furthermore relates to a method for the recombinant production of pharmaceuticals or fine chemicals in host organisms, where a host organism or a part thereof is transformed with one of the above-described nucleic acid molecule expression cassettes and this expression cassette comprises one or more structural genes which code for the desired fine chemical or catalyse the biosynthesis of the desired fine chemical, where the transformed host organism is grown and where the desired fine chemical is isolated from the growth medium. This method can be applied widely to fine chemicals such as enzymes, vitamins, amino acids, sugars, fatty acids, natural and synthetic flavorings, aroma substances and colorants. Especially preferred is the production of polyunsaturated fatty acids, poltocopherols, tocotrienols and carotenoids. The growing of the transformed host organisms and the isolation from the host organisms or the growth medium are accomplished by methods known to the skilled worker. The production of pharmaceuticals such as, for example, antibodies or vaccines, is described in Hood E E, Jilka J M (1999). Curr Opin Biotechnol. 10(4): 382-6; Ma J K, Vine N D (1999). Curr Top Microbiol Immunol. 236: 275-92.

In accordance with the invention, the expression of a structural gene can, of course, also take place, or be influenced, independently of carrying out the method according to the invention or using the subject matters according to the invention.

EXAMPLES

General Methods

The chemical synthesis of oligonucleotides can take place for example in a known manner by the phosphoamidite method (Voet, Voet, 2nd edition, Wiley Press New York, page 896-897). The cloning steps carried out for the purposes of the present invention, such as, for example, restriction cleavages, agarose gel electrophoresis, purification of DNA fragments, transfer of nucleic acids to nitrocellulose and nylon membranes, linkage of DNA fragments, transformation of *E. coli* cells, culturing of bacteria, replication of phages and sequence analysis of recombinant DNA are carried out as described in Sambrook et al. (1989) Cold Spring Harbour Laboratory Press; ISBN 0-87969-309-6. The sequencing of recombinant DNA molecules takes place using a laser fluorescence DNA sequencer from the company MWG-Licor by the method of Sanger (Sanger et al. (1977) Proc Natl Acad Sci USA 74:5463-5467).

Example 1

Plants, Pathogens and Inoculation

The barley variety Golden Promise is from Patrick Schweizer, Institut für Pflanzengenetik and Kulturpflanzenforschung Gatersleben. The variety Pallas and the backcrossed line BCIngrid-mlo5 was provided by Lisa Munk, Department of Plant Pathology, Royal Veterinary and Agricultural University, Copenhagen, Denmark. Its preparation is described (Kølster P et al. (1986) Crop Sci 26: 903-907).

Unless otherwise described, the seed which has been pregerminated for 12 to 36 hours in the dark on moist filter paper is placed in batches of 5 grains along the edge of a square pot (8×8 cm) in Fruhstorfer soil type P, covered with soil and watered regularly with tapwater. All plants are grown in controlled-environment cabinets or chambers at from 16 to 18° C. for 5 to 8 days, at a relative atmospheric humidity of from 50 to 60% and in a 16/8-hour photo period with 3000 and 5000 lux, respectively (50 and 60 µmols-$^1$m-$^2$ photon flux density, respectively) and employed in the experiments in the seedling stage. In the case of experiments where primary leaves are treated, the latter are fully developed.

Before the plants are subjected to the transient transfection experiments, they are grown in controlled-environment cabinets or chambers at a daytime temperature of 24° C., nighttime temperature of 20° C., relative atmospheric humidity of 50 to 60% and a 16/8-hour photo period with 30000 lux.

Powdery mildew of barley *Blumeria graminis* (DC) Speer f. sp. *hordei* Em. Marchal der Rasse A6 (Wiberg A (1974) Hereditas 77: 89-148) (BghA6) is used to inoculate barley plants. The mildew was provided by the Institut für Biometrie, JLU Gießen. The inoculum is maintained in controlled-environment cabinets under conditions which are identical to those which have been described above for the plants by transferring the conidia from infected plant material to 7-day old barley plants cv. Golden Promise which have been raised at regular intervals, at a density of 100 conidia/mm².

The inoculation with BghA6 is carried out using 7-day-old seedlings by shaking the conidia of infected plants in an inoculation tower at a density of approximately 100 conidia/mm² (unless otherwise stated).

Example 2

RNA Extraction

Total RNA is extracted from 8 to 10 primary leaf segments (5 cm in length) by means of "RNA extraction buffer" (AGS, Heidelberg, Germany).

To this end, central primary leaf segments 5 cm in length are harvested and homogenized in liquid nitrogen using a pestle and mortar. The homogenate is stored at −70° C. until the RNA is extracted.

Total RNA is extracted from the frozen leaf material with the aid of an RNA extraction kit (AGS, Heidelberg). To this end, 200 mg of the frozen leaf material is covered with 1.7 ml of RNA extraction buffer (AGS) in a microcentrifuge tube (2 ml) and immediately subjected to thorough mixing. After the addition of 200 µl of chloroform, the mixture is again mixed thoroughly and shaken for 45 minutes at room temperature on an orbital shaker at 200 rpm. Thereafter, the mixture is centrifuged for 15 minutes at 20000 g and 4° C. in order to separate the phases, the aqueous top phase is transferred into a fresh microcentrifuge tube, and the bottom phase is discarded. The aqueous phase is again purified with 900 µl of chloroform by homogenizing 3 times for 10 seconds and recentrifuging (see above) and removing the top phase. To precipitate the RNA, 850 µl of 2-propanol are then added, the mixture is homogenized and placed on ice for 30 to 60 minutes. Thereafter, the mixture is centrifuged for 20 minutes (see above), the supernatant is carefully decanted off, 2 ml of 70% strength ethanol (−20° C.) are added, using a pipette, and the batch is mixed and again centrifuged for 10 minutes. The supernatant is then again decanted off and the pellet is carefully freed from residual fluid, using a pipette, and then dried in a stream of pure air on a sterile workbench. Thereafter, the RNA is dissolved in 50 µl of DEPC water on ice, and the batch is mixed and centrifuged for 5 minutes (see above). 40 µl of the supernatant are transferred into a fresh microcentrifuge tube as RNA solution and stored at −70° C.

The RNA concentration is determined photometrically. To this end, the RNA solution is diluted 1:99 (v/v) with distilled water and the absorbance (Photometer DU 7400, Beckman) is measured at 260 nm ($E_{260\,nm}$=1 at 40 µg RNA/ml). In accordance with the calculated RNA contents, the concentrations of the RNA solutions are subsequently standardized with DEPC water to 1 µg/µl and verified in a denaturating agarose gel.

To verify the RNA concentrations in a horizontal agarose gel (1% agarose in 1×MOPS buffer with 0.2 µg/ml ethidium bromide), 1 µl of RNA solution is treated with 1 µl of 10×MOPS, 1 µl of color marker and 7 µl of DEPC water, separated according to size at a voltage of 120 V in the gel in 1×MOPS running buffer in the course of 1.5 hours and photographed under UV light. Any differences in concentration of the RNA extracts are standardized with DEPC water, and the standardization is again verified in the gel.

Example 3

Cloning the Barley Subtilisin RNR9 cDNA Sequence

A contig for subtilisin RNR9 was constructed from the publicly available EST sequences HW03O11, HO31J10 (Crop EST Database of IPK Gatersleben) and BM368585 (SCRI). The clone was subcloned into pIPKTA38 (see below) via restriction cleavage & ligation. The following approach was used for the end-to-end PCR of the full-length clone HvRNR9.

```
Upper primer (SEQ ID NO: 15, see FIG. 15):
CGGCACGAGGCTCTGGTGGT

Lower primer (SEQ ID NO: 16, see FIG. 15):
CCTTTTCCACAAAGGGAGA
```

Cycler Program:

| | | |
|---|---|---|
| 94° C. | 3 minutes | |
| 94° C. | 60 seconds | |
| 55° C. | 20 seconds | 35 cycles |
| 72° C. | 30 seconds | |
| 72° C. | 10 minutes | |
| 4° C. | Hold | |

Mix:
1 µl template (cDNA barley)
5 µl 10× buffer
20 pmol primer 1
20 pmol primer 2
1 µl dNTPs (Invitrogen, 10 mM)

1 µl cloned Pfu DNA polymerase (Stratagene, 2.5 U/µl)
H₂O to 50 µl

The end-to-end PCR yielded a product of 449 bp. The PCR product obtained was isolated via a 1% strength agarose gel, extracted from the gel, and used for ligation.

Preparation of Vector:

| pIPKTA38: | 5 µg DNA | |
|---|---|---|
| | 1 µl SwaI (10 U/µl, Roche) | |
| | 2 µl Buffer H | |
| | H₂O add 20 µl | Incubation at 37° C. over night |

Subsequently, the vector was purified with Nucleo Spin Extract II (Macherey-Nagel) and concentration was determined.

| Ligation: | 25 ng Vector | |
|---|---|---|
| | 24.3 ng Fragment | |
| | 2 µl 10x Ligase Buffer | |
| | 1 µl T4 DNA-Ligase (1 U/µl) | |
| | H₂O add 20 µl | Ligation at 4° C. over night |

The ligation product was transformed in chemocompetent *E. coli* cells (TOP10, Invitrogen), plated on LB-Kan selection medium and resulting colonies.

Example 4

Carrying Out the Transient Single-Cell RNAi Analysis

Biological Material

Barley near-isogenic lines (NILs) of the cultivars cv Ingrid (Mlo) and Ingrid BCS mlo5 or barley cv Golden Promise were grown in controlled-environment chambers in pots filled with potting compost (provenance: IPK Gatersleben) (16 hours light from metal halogen lamps; 8 hours darkness, relative atmospheric humidity of 70%, constant temperature of 18° C.). *Blumeria graminis* DC Speer f. sp. *hordei* (Bgh) (isolate 4.8 comprising AvrMla9) was grown at 22° C. and 16 hours light by weekly transfer to fresh barley leaves of the cultivar cv. Golden Promise. *Blumeria graminis* DC Speer f. sp. *tritici* Em Marchal (Bgt) of the Swiss isolate FAL (Reckenholz) was propagated at 22° C. and 16 hours light by weekly transfer to fresh leaves of wheat of the cultivar cv. Kanzler.

Plasmid Vectors

The vector pIPKTA38 was used as entry vector for the Gateway™ cloning system (Invitrogen). The vector is a pENTR1a derivative where the ccdB gene had been removed and a novel multiple cloning site had been inserted. The destination vector used was pIPKTA30N, which is based on a pUC18 background and which comprises a constitutive promoter, terminator and two Gateway cassettes comprising attR sites, ccdB gene and a chloramphenicol resistance gene. The two cassettes are arranged in opposite directions and separated from one another by a spacer from the wheat RGA2 gene (accession number AF326781). This vector system permits a one-step transfer of two copies of a PCR fragment via entry vector into the dsRNAi vector by means of Gateway LR clonase reaction (Invitrogen).

PCR and Primer Design

EST sequences of the target gene were amplified via PCR. Purified DNA from the selected cDNA clones was used as template for the PCR reaction. The primers were derived with the aid of the software package "Primer3" in the batch-file mode using the 5'-EST sequences. The EST sequences were typically amplified with a universal forward primer and a reverse EST-specific primer. The amplificates were in the range of from 400-700 bp. The primers were 20-22 bp in length and had a $T_m$ of approx. 65° C. The PCR reactions were carried out in 96-well microtiter plates using a DNA polymerase which produces blunt ends (ThermalAce; Invitrogen). The PCR products were purified with the aid of the MinElute UF Kit (Qiagen, Hilden, Germany) and eluted with 25 µl of water.

Ligation into the Entry Vector

The PCR fragments were cloned into the Swa I cleavage site of this vector pIPKTA38. The ligation was carried out at 25° C. in the presence of the N U T4 DNA ligase (MBI Fermentas) and 5 U of Swa I per reaction. To optimize the reaction conditions for Swa I, the buffer was supplemented with NaCl to a final concentration of 0.05 M. After 1 h, the reaction was terminated by heating for 15 minutes at 65° C. Thereafter, an additional 5 U of Swa I were added in order to suppress a religation of the plasmid. The Swa I buffer was supplemented with additional NaCl to a final concentration of 0.1 M. The reaction mixtures were incubated for a further hour at 25° C.

The resulting recombinant pIPKTA38-EST clones were employed for the transformation of chemically competent *E. coli* DH10B cells in 96-well PCR microtiter plates (5 µl of ligation mixture per 20 µl of competent cells) and plated onto LB agar plates with kanamycin. One colony of each cloning reaction was picked and taken up in 1.2 ml of LB+kanamycin liquid culture and distributed in 96-deep-well plates. The plates were covered with an air-permeable film and incubated for 18 hours at 37° C. on a shaker. Thereupon, the deep-well plates were centrifuged for 10 minutes at 750 g, and the pellets were used for isolating the plasmid by means of the NucleoSpin Robot-96 plasmid kit (Macherey-Nagel). The presence of the pIPKTA38 plasmid was verified via restriction digest with EcoRI. The positive pIPKTA38 clones were employed as donor vector in the LR reaction.

LR Reaction and Preparation of RNAi Constructs

EST fragments in pIPKTA38 were cloned as inverted repeats into the RNAi destination vector pIPKTA30N via a single LR recombination reaction. The reaction volume was reduced to 6 µl and comprised 1 µl of the pIPKTA38 donor clone, 1 µl pIPKTA30N destination vector (150 ng/µl), 0.8 µL LR clonase enzyme mix and 3.2 µl of H₂O. The reaction was incubated overnight at room temperature, and 5 µl of it were transformed into 20 µl of chemically competent *E. coli* cells in 96-well PCR plates. Two 96-deep-well plates with LB+ampicillin were half-filled with half the volume of the transformation mix, sealed with an air-permeable film and incubated for 24 hours at 37° C. on a plate shaker. Thereafter, the deep-well plates were centrifuged for 10 minutes at 750 g, and the pellets of two duplicates of each clone were combined and subjected to the plasmid preparation. The NucleoSpin Robot-96 plasmid kit (Macherey-Nagel) was used for this purpose. The DNA quantity was on average 20-30 µg of DNA per clone.

Particle Bombardment and Inoculation with Fungal Spores

Segments of primary leaves of 7-day-old barley seedlings were placed on 0.5% w/v Phytoagar (Ducheva) in water comprising 20 ppm of benzimidazole and bombarded with gold particles (diameter 1 µm) in a PDS-1000/He system (Bio-Rad, Munich, Germany) using the Hepta adaptor with a helium pressure of 900 psi. Seven leaf segments were employed per bombardment. The particle coating with 0.5 M Ca(NO$_3$)$_2$ was carried out as described by Schweizer et al., 1999, except that the stock solution comprised 25 mg ml$^{-1}$ gold. After the coating, all of the supernatant was removed, and the particles were resuspended in 30 μl of pure ethanol. 2.18 mg of gold microcarrier were employed per bombardment. Four hours after the bombardment, the leaf segments were placed on 1% w/v Phytoagar (Ducheva) in water comprising 20 ppm of benzimidazole in 20×20 cm plates and weighted down at both ends.

The leaf segments were inoculated with spores of Bgt and Bgh 48 hours or 96 hours after the particle bombardment. The plasmid pUbiGUS, which comprises the β-glucuronidase (GUS) gene under the control of the maize ubiquitin promoter, was employed as reporter construct for transformed epidermal cells. 40 hours after the inoculation, the leaf segments were stained on GUS activity and destained for 5 minutes with 7.5% w/v trichloroacetic acid and 50% methanol. The GUS staining solution has been described in Schweizer et al. 1999.

To evaluate the interaction of phenotypes, GUS-stained cells were counted under an optical microscope, and the number of haustoria in these transformed cells was determined, whereby the haustorial index is derived. As an alternative, the number of GUS-stained cells which comprised at least one haustorium was determined, and the susceptibility index was calculated thereby.

see FIG. 17: Increasing the host resistance by subtilisin RNR9 RNAi.

We claim:

1. A method for increasing resistance to a fungal pathogen in a plant, plant cell or in a part of a plant relative to a corresponding control plant, plant cell, or plant part, comprising:
   1) reducing the activity of a subtilisin (RNR9) polypeptide in a plant, plant cell or plant part by introducing into said plant, plant cell or plant part a nucleic acid molecule encoding a dsRNA, an antisense RNA, or a RNAi that targets a mRNA encoding the RNR9 polypeptide, and
   2) selecting for a plant, plant cell, or plant part having increased resistance to a fungal pathogen as compared to a corresponding control plant, plant cell, or plant part;
   wherein the RNR9 polypeptide is encoded by a polynucleotide comprising at least one nucleic acid molecule selected from the group consisting of:
   a) a nucleic acid molecule which encodes a polypeptide comprising the amino acid sequence of SEQ ID NO: 2;
   b) a nucleic acid molecule which comprises the polynucleotide sequence of SEQ ID NO: 1;
   c) a nucleic acid molecule which encodes a polypeptide comprising an amino acid sequence having at least 90% sequence identity to the amino acid sequence of SEQ ID NO: 2; and
   d) a nucleic acid molecule which hybridizes with the complement of the nucleic acid molecule of (a) or (b) under stringent conditions comprising hybridization in 4×SSC at 65° C. followed by washing in 0.2×SSC at 65° C., wherein the nucleic acid molecule codes for a polypeptide having essentially identical properties to the polypeptide of SEQ ID NO: 2.

2. The method of claim 1, wherein the activity of the RNR9 polypeptide in mesophyll cells and/or epidermal cells is reduced.

3. The method of claim 1, wherein the activity of the RNR9 polypeptide in the lemma, palea, and/or glume is reduced.

4. The method of claim 1, wherein the fungal pathogen is selected from the group consisting of the families Pucciniaceae, Mycosphaerellaceae and Hypocreaceae.

5. The method of claim 1, wherein
   a) the nucleic acid molecule encoding a dsRNA comprises a sense strand having a nucleotide sequence selected from the group consisting of:
   i) a nucleotide sequence which encodes a polypeptide comprising the amino acid sequence of SEQ ID NO: 2;
   ii) the polynucleotide sequence of SEQ ID NO: 1;
   iii) a nucleotide sequence which encodes a polypeptide comprising an amino acid sequence having at least 90% sequence identity to the amino acid sequence of SEQ ID NO: 2;
   iv) a nucleotide sequence which hybridizes with the complement of the nucleotide sequence of i) or ii) under stringent conditions comprising hybridization in 4×SSC at 65° C. followed by washing in 0.2×SSC at 65° C.; and
   v) a nucleotide sequence which comprises a fragment of about 19 to about 24 bases of the nucleotide sequence of i) or ii);
   or
   b) the nucleic acid molecule encoding an antisense RNA comprises:
   i) a sequence having at least 90% sequence identity with the complementary sequence of a nucleotide sequence which encodes a polypeptide comprising the amino acid sequence of SEQ ID NO: 2; or
   ii) a sequence having at least 90% sequence identity with the complementary sequence of the polynucleotide sequence of SEQ ID NO: 1; or
   iii) a nucleotide sequence which comprises a fragment of about 19 to about 24 bases of the nucleotide sequence of b) i) or b) ii).

6. The method of claim 5, wherein the nucleic acid molecule is introduced into the plant cell in a recombinant expression cassette comprising said nucleic acid molecule in operable linkage with a promoter which is active in plants, the method further comprises:
   a) regenerating a plant from the plant cell, and
   b) expressing said nucleic acid molecule in a sufficient amount and over a sufficient period of time to generate, or to increase, resistance to a fungal pathogen in said plant relative to a corresponding wild-type control plant.

7. The method according to claim 6, wherein the promoter which is active in plants is selected from the group consisting of:
   (a) a pathogen-inducible promoter;
   (b) an epidermis- or mesophyll-specific promoter;
   (c) a lemma-, palea- and/or gluma-specific promoter;
   (d) a pathogen-inducible epidermis- or mesophyll-specific promoter;
   (e) an epidermis- or mesophyll-specific lemma-, palea- and/or gluma-specific promoter; and
   a pathogen-inducible epidermis- or mesophyll-specific lemma-, palea- and/or glumae-specific promoter.

8. The method of claim 1, further wherein Bax inhibitor 1, ROR2, SnAP34 and/or Lumenal Binding protein BiP is transgenically overexpressed in the plant, plant cell, or plant part.

9. The method of claim 1, further wherein the activity of ARM1, RacB, CSLI, HvNaOX and/or MLO is decreased in the plant, plant cell, or plant part by transgenically expressing a nucleotide sequence encoding a dsRNA, antisense RNA, or RNAi that targets a mRNA encoding ARM1, RacB, CSL1, HvNaOX and/or MLO.

10. The method according to claim 8, wherein the Bax inhibitor 1 is expressed under the control of a mesophyll- and/or a root-specific promoter.

11. The method according to claim 1, wherein the fungal pathogen is selected from the group consisting of the species *Puccinia triticina, Puccinia striiformis, Mycosphaerella graminicola, Stagonospora nodorum, Fusarium graminearum, Fusarium culmorum, Fusarium avenaceum, Fusarium poae* or *Microdochium nivale*.

12. The method according to claim 1, wherein the plant is from a plant genus selected from the group consisting of *Hordeum, Avena, Secale, Triticum, Sorghum, Zea, Saccharum* and *Oryza*.

13. A transgenic plant cell, plant, or part of the plant produced by the method of claim 1, wherein the transgenic plant cell, plant, or part of the plant has increased resistance to a fungal pathogen relative to a corresponding wild type control plant cell, plant or part thereof.

14. A method for the generation of a plant which is resistant to a mesophyll-cell-penetrating pathogen or to an epidermis-penetrating pathogen, comprising generating a plant from the plant cell of claim 13, wherein the plant is resistant to a mesophyll-cell-penetrating pathogen or an epidermis-penetrating pathogen.

15. The method of claim 14, where the mesophyll-cell-penetrating, pathogen is *Septoria* or rusts, and wherein the epidermis-penetrating pathogen is mildew.

16. The method of claim 1, wherein the RNR9 polypeptide comprises an amino acid sequence having at least 95% sequence identity to the amino acid sequence of SEQ ID NO: 2.

* * * * *

```
                       SEQUENCE LISTING

<160> NUMBER OF SEQ ID NOS: 16

<210> SEQ ID NO 1
<211> LENGTH: 3737
<212> TYPE: DNA
<213> ORGANISM: Triticum aestivum
<220> FEATURE:
<221> NAME/KEY: misc_feature
<222> LOCATION: (87)..(89)
<223> OTHER INFORMATION: transcription start

<400> SEQUENCE: 1
tatcgtcgac ccacgcgtcc gccacccatc gctcatttcc ggcgagccac cgcgcggggg      60
ccgccgatct ccggcgaatc gcgccgatgc cgccgcccgc gatggcggcc gagaagagga     120
gggccgcgta cgcggccttc ctcccgctcc tcctcctcct cgcgctccgc gccctcctcc     180
cctcctccga ccccccggcc cggggcgggg aggaaaccct agccagcagc aggtacgtcg     240
tgcggttcct cgagtaccgc cccgccgacg accaccggga gtacctggag gacggcctcc     300
cccgcgaggc cgggccgtgg cggtgggtgg agcggcggaa ccccgcggcc gcgcacccga     360
ccgacttcgc cgtgctcgag atccgcgacg cgcaccggga cgccgtctcc gaggccctcc     420
gcgcgctcgc ccgcgtccgg gacgtgcacc ccgacaccag ccactcgcgg gccgccctgt     480
ccgcagatcg ggcgcggggc aagcgcttca ccgccatgtc gttcgaggag gagggacgcg     540
gcggcgacga cgacgcggtt cccagcaata atgctagttc ctcttctggt ggtccgaggc     600
ggaagcttca aatgcggaga ccacatgtga catctctatt tggagctgca caactatggg     660
aaagaggctt cactggtagg aaagtcaaaa tggccatttt tgacactggt attcgggcag     720
atcacccaca ttttcgcaat attaaggagc gcacaaattg gacaaatgaa gacacattaa     780
atgacaacct tggacatgga acatttgtag ctggagtgat tgctggtcaa gatccagaat     840
gtcctggatt tgcaccaaac actgagatat atgcatttcg agtgttcaca gatgctcaga     900
tatcctacac atcatggttc ttggatgcat ttaattatgc gatggcaact ggtatggatg     960
tattgaattt gagtattggt ggacctgatt acctggatct cccctttgtg gaaaaggtct    1020
gggagctcac agcaaacaac attattatgg tatcagctat tggaaatgat ggtcctctct    1080
atggcacatt aaataaccca gcggaccaaa gcgacgtcat tggcgttggt ggtattgatt    1140
acaataacca catagcttca ttttcctcta gaggcatgac tacctgggaa cttccccatg    1200
gatatggccg tgtaaaacct gatgttgtcg catacagtcg tgatataatg ggttctaaga    1260
ccagcacagg ctgcaagact cttttcaggta caagtgttgc aagcccggtg gttgctggag    1320
cagtatgctt gcttgttagt gttataccag aagacaagcg gaaatccatc cttaatcctg    1380
```

```
ctagtatgaa acaggccctt gttgagggtg cttctaagct tgtggggccg aatatatatg      1440
agcagggtgc aggcaagcct gatctatggc aatcatatga aatattgaaa aattaccaac      1500
cacgagcaag tgtatttcct aacatgcttg acttcaccga ctgtccctac ttctggcctt      1560
tttgtcggca acctttgtat gctggagcca tgccagtagt attcaatgct acaattctta      1620
atgggatggg ggtgattggt tatgttaagg atccacctgt atggcagcca tctgaagatg      1680
tgggcaatct tctcactgtt cacttcacct actcggacac catctggcct tggacagggt      1740
accttgccct gcacatgcaa gttaaagacg aaggttctca gttttcaggc ataattagtg      1800
gcaatgttac cctgtcgatt tacagcccag ctactgaggg ggaaagcagc ccacggagta      1860
gtacgtgtgt tctttacctg aaggtcaggg tggttcaaac acctgttagg tcaagaagaa      1920
tactgtggga ccaatttcat aacatcaagt acccatctgg atatgttccg agggattcac      1980
ttaatgtgaa taatgatatc cttgattggc atggtgacca cttacacaca aattttcaca      2040
tactgttcaa catgctgaga gatgcaggat actatgttga dacccttggg tcaccactta      2100
cctgctttga cgctagcaat tatggtacac tgctcatggt tgatcttgag dacgagtact      2160
tcagtgaaga gattcagaaa ctcagggatg atgttgtaca caaggggctc ggccttgctg      2220
tttttgctga atggtatcat gttgatacca tggtgaagat gacattcttt gatgaaaata      2280
cccgcagttg gtggagtccg cttactggtg gtgcaaatat tcctgcgctt aatgaacttt      2340
tggccccatt tggcattgct tttggggaca aaatattgag tggtgatttc tcaatcaatg      2400
gtgagcagtc ccactatgct tctgggactg atatagtgca attcccagca ggaggttttt      2460
tgcatggctt cgaactccag gaagaccca aaactgcaca gaatagctca actccagata      2520
cacagaactc ccagtcccag gagaagagca aggcgaaggg cgaattgcag tatatgggga      2580
ttcaaattgt cttgacagta gtcacatggt aacaaactgt tattggcttt tgagaaaaat      2640
tgtggagttt gctggcaatg gactcagaga tcctgtcctt ttctcagaag caactcggtt      2700
aaaatttcca gtttttgaga acatccagaa acccttgcgt agacccgatg taaattttc      2760 aatgttttca tctgtcattg gcaaggaatt gatatgtcac caggattccc gatttgaagt      2820
ttggggtacg aaaggttatg gtatccaact aacaggcaca acaagaaagc tgccagaata      2880
ccaaaagaat gaagtttcta gtagtcccaa tcgattaata aaatcttctt acaagagaca      2940
agatgaagct ggcttgcaaa aatccatttt agcaccgagt gctaataaat ttgatgataa      3000
tagagattat tttggcttta tcagccatga agaggtcgca agccaatgga tggtacctgc      3060
ttgctttgct gtcactactt gcattctggt gtacctcagt tgcagagcgc aacaaaggcg      3120
ccgtcgacca aggaaagggt ccgcaaccgg tcgtctgtca agttcggtat aacatggaaa      3180
cttgtgtggg gccaaagaag gttttggctc agcgtgtct ggccatctgc catggtacat      3240
gatataactg aagttacatc ggtccactga ctggacataa aaaagctcgc aatggatgtc      3300
aatcgaggtc caagtcgtgg tggctcatgt ttagaatgtg cgaagagagc ccagtcaaac      3360
acctctgcaa ctgcgtggct atgttccaac attttgtgtc atgcgccatc gccatcgcca      3420
tcgccatcca gttgtaacaa actctgtgtc tataataata atagactgct ttgggacata      3480
ataggcgaga gctaattcag taggaagagg ctagggttga cgtctttctt tctttctttc      3540
tttttcatct cttcttcttc ttccttttt cttttcttt gtgaaaggat gacttgcttc      3600
ttgtaggtca gtaagccatt ctagttttca gggtggctat gcttcagctt gtaagtactg      3660
gacgagctca tctgaaaaca gaggaaggcc tcagcagttt atgagggttt ttttctggag      3720
taaaaaaaaa aaaaaaa                                                     3737
```

-continued

```
<210> SEQ ID NO 2
<211> LENGTH: 1038
<212> TYPE: PRT
<213> ORGANISM: Triticum aestivum

<400> SEQUENCE: 2

Met Pro Pro Ala Met Ala Ala Glu Lys Arg Arg Ala Tyr Ala
1               5                   10                  15

Ala Phe Leu Pro Leu Leu Leu Leu Ala Leu Arg Ala Leu Leu Pro
            20                  25                  30

Ser Ser Asp Pro Pro Ala Arg Gly Gly Glu Glu Thr Leu Ala Ser Ser
        35                  40                  45

Arg Tyr Val Val Arg Phe Leu Glu Tyr Arg Pro Ala Asp Asp His Arg
    50                  55                  60

Glu Tyr Leu Glu Asp Gly Leu Pro Arg Glu Ala Gly Pro Trp Arg Trp
65                  70                  75                  80

Val Glu Arg Arg Asn Pro Ala Ala His Pro Thr Asp Phe Ala Val
                85                  90                  95

Leu Glu Ile Arg Asp Ala His Arg Asp Ala Val Ser Glu Ala Leu Arg
                100                 105                 110

Ala Leu Ala Arg Val Arg Asp Val His Pro Asp Thr Ser His Ser Arg
            115                 120                 125

Ala Ala Leu Ser Ala Asp Arg Ala Arg Gly Lys Arg Phe Thr Ala Met
        130                 135                 140

Ser Phe Glu Glu Glu Gly Arg Gly Gly Asp Asp Ala Val Pro Ser
145                 150                 155                 160

Asn Asn Ala Ser Ser Ser Gly Gly Pro Arg Arg Lys Leu Gln Met
                165                 170                 175

Arg Arg Pro His Val Thr Ser Leu Phe Gly Ala Ala Gln Leu Trp Glu
            180                 185                 190

Arg Gly Phe Thr Gly Arg Lys Val Lys Met Ala Ile Phe Asp Thr Gly
        195                 200                 205

Ile Arg Ala Asp His Pro His Phe Arg Asn Ile Lys Glu Arg Thr Asn
    210                 215                 220

Trp Thr Asn Glu Asp Thr Leu Asn Asp Asn Leu Gly His Gly Thr Phe
225                 230                 235                 240

Val Ala Gly Val Ile Ala Gly Gln Asp Pro Glu Cys Pro Gly Phe Ala
                245                 250                 255

Pro Asn Thr Glu Ile Tyr Ala Phe Arg Val Phe Thr Asp Ala Gln Ile
            260                 265                 270

Ser Tyr Thr Ser Trp Phe Leu Asp Ala Phe Asn Tyr Ala Met Ala Thr
        275                 280                 285

Gly Met Asp Val Leu Asn Leu Ser Ile Gly Gly Pro Asp Tyr Leu Asp
    290                 295                 300

Leu Pro Phe Val Glu Lys Val Trp Glu Leu Thr Ala Asn Asn Ile Ile
305                 310                 315                 320

Met Val Ser Ala Ile Gly Asn Asp Gly Pro Leu Tyr Gly Thr Leu Asn
                325                 330                 335

Asn Pro Ala Asp Gln Ser Asp Val Ile Gly Val Gly Gly Ile Asp Tyr
            340                 345                 350

Asn Asn His Ile Ala Ser Phe Ser Ser Arg Gly Met Thr Thr Trp Glu
        355                 360                 365

Leu Pro His Gly Tyr Gly Arg Val Lys Pro Asp Val Val Ala Tyr Ser
    370                 375                 380
```

-continued

Arg Asp Ile Met Gly Ser Lys Thr Ser Thr Gly Cys Lys Thr Leu Ser
385                 390                 395                 400

Gly Thr Ser Val Ala Ser Pro Val Val Ala Gly Ala Val Cys Leu Leu
                405                 410                 415

Val Ser Val Ile Pro Glu Asp Lys Arg Lys Ser Ile Leu Asn Pro Ala
            420                 425                 430

Ser Met Lys Gln Ala Leu Val Glu Gly Ala Ser Lys Leu Val Gly Pro
        435                 440                 445

Asn Ile Tyr Glu Gln Gly Ala Gly Lys Pro Asp Leu Trp Gln Ser Tyr
    450                 455                 460

Glu Ile Leu Lys Asn Tyr Gln Pro Arg Ala Ser Val Phe Pro Asn Met
465                 470                 475                 480

Leu Asp Phe Thr Asp Cys Pro Tyr Phe Trp Pro Phe Cys Arg Gln Pro
                485                 490                 495

Leu Tyr Ala Gly Ala Met Pro Val Val Phe Asn Ala Thr Ile Leu Asn
            500                 505                 510

Gly Met Gly Val Ile Gly Tyr Val Lys Asp Pro Pro Val Trp Gln Pro
        515                 520                 525

Ser Glu Asp Val Gly Asn Leu Leu Thr Val His Phe Thr Tyr Ser Asp
    530                 535                 540

Thr Ile Trp Pro Trp Thr Gly Tyr Leu Ala Leu His Met Gln Val Lys
545                 550                 555                 560

Asp Glu Gly Ser Gln Phe Ser Gly Ile Ile Ser Gly Asn Val Thr Leu
                565                 570                 575

Ser Ile Tyr Ser Pro Ala Thr Glu Gly Glu Ser Ser Pro Arg Ser Ser
            580                 585                 590

Thr Cys Val Leu Tyr Leu Lys Val Arg Val Gln Thr Pro Val Arg
        595                 600                 605

Ser Arg Arg Ile Leu Trp Asp Gln Phe His Asn Ile Lys Tyr Pro Ser
    610                 615                 620

Gly Tyr Val Pro Arg Asp Ser Leu Asn Val Asn Asn Asp Ile Leu Asp
625                 630                 635                 640

Trp His Gly Asp His Leu His Thr Asn Phe His Ile Leu Phe Asn Met
                645                 650                 655

Leu Arg Asp Ala Gly Tyr Tyr Val Glu Thr Leu Gly Ser Pro Leu Thr
            660                 665                 670

Cys Phe Asp Ala Ser Asn Tyr Gly Thr Leu Leu Met Val Asp Leu Glu
        675                 680                 685

Asp Glu Tyr Phe Ser Glu Glu Ile Gln Lys Leu Arg Asp Asp Val Val
    690                 695                 700

His Lys Gly Leu Gly Leu Ala Val Phe Ala Glu Trp Tyr His Val Asp
705                 710                 715                 720

Thr Met Val Lys Met Thr Phe Phe Asp Glu Asn Thr Arg Ser Trp Trp
                725                 730                 735

Ser Pro Leu Thr Gly Gly Ala Asn Ile Pro Ala Leu Asn Glu Leu Leu
            740                 745                 750

Ala Pro Phe Gly Ile Ala Phe Gly Asp Lys Ile Leu Ser Gly Asp Phe
        755                 760                 765

Ser Ile Asn Gly Glu Gln Ser His Tyr Ala Ser Gly Thr Asp Ile Val
    770                 775                 780

Gln Phe Pro Ala Gly Gly Phe Leu His Gly Phe Glu Leu Gln Glu Asp
785                 790                 795                 800

Pro Lys Thr Ala Gln Asn Ser Ser Thr Pro Asp Thr Gln Asn Ser Gln
                805                 810                 815

Ser Gln Glu Lys Ser Lys Leu Ser Ser Ile Leu Gly Met Leu Glu Ala
            820                 825                 830

Gly Glu Gly Arg Ile Ala Val Tyr Gly Asp Ser Asn Cys Leu Asp Ser
        835                 840                 845

Ser His Met Val Thr Asn Cys Tyr Trp Leu Leu Arg Lys Ile Val Glu
    850                 855                 860

Phe Ala Gly Asn Gly Leu Arg Asp Pro Val Leu Phe Ser Glu Ala Thr
865                 870                 875                 880

Arg Leu Lys Phe Pro Val Phe Glu Asn Ile Gln Lys Pro Leu Arg Arg
            885                 890                 895

Pro Asp Val Asn Phe Ser Met Phe Ser Ser Val Ile Gly Lys Glu Leu
        900                 905                 910

Ile Cys His Gln Asp Ser Arg Phe Glu Val Trp Gly Thr Lys Gly Tyr
    915                 920                 925

Gly Ile Gln Leu Thr Gly Thr Thr Arg Lys Leu Pro Glu Tyr Gln Lys
    930                 935                 940

Asn Glu Val Ser Ser Ser Pro Asn Arg Leu Ile Lys Ser Ser Tyr Lys
945                 950                 955                 960

Arg Gln Asp Glu Ala Gly Leu Gln Lys Ser Ile Leu Ala Pro Ser Ala
            965                 970                 975

Asn Lys Phe Asp Asp Asn Arg Asp Tyr Phe Gly Phe Ile Ser His Glu
        980                 985                 990

Glu Val Ala Ser Gln Trp Met Val Pro Ala Cys Phe Ala Val Thr Thr
    995                 1000                1005

Cys Ile Leu Val Tyr Leu Ser Cys Arg Ala Gln Gln Arg Arg Arg
    1010                1015                1020

Arg Pro Arg Lys Gly Ser Ala Thr Gly Arg Leu Ser Ser Ser Val
    1025                1030                1035

<210> SEQ ID NO 3
<211> LENGTH: 449
<212> TYPE: DNA
<213> ORGANISM: Hordeum vulgare

<400> SEQUENCE: 3
cggcacgagg ctctggtggt cggaggcgga agcttcaaat gcggagatca catgtgacat    60
ctctttttgg agctgcacag ctatgggaaa gaggcttcac tggtaggaaa gtcaaaatgg   120
ccatttttga cactggtatt cgggcggacc acccacactt ccgtaatatt aaggagcgca   180
caaattggac aaatgaagac acattaaatg acaaccttgg tcatgaaca ttcgtagctg    240 gagtgattgc tggtcaagat ccagaatgtc ttggatttgc accagacact gagatatatg   300
catttcgagt gttcacagat gctcagtgca gatatcctac acatcatggt tcttggatgc   360
atttaattat gctatggcta ctggtatgga tgtattgaat ttgagtattg gtggacctga   420
ttacctggat ctccccttg tggaaaagg                                      449

<210> SEQ ID NO 4
<211> LENGTH: 147
<212> TYPE: PRT
<213> ORGANISM: Hordeum vulgare
<220> FEATURE:
<221> NAME/KEY: MISC_FEATURE
<222> LOCATION: (132)..(132)
<223> OTHER INFORMATION: A frameshift may occur immediately before or
      immediately after position 132, resulting in an alternatively
      translated, shifted amino acid sequence.

<400> SEQUENCE: 4

```
Ala Arg Gly Ser Gly Gly Arg Arg Lys Leu Gln Met Arg Ser
1               5                   10                  15

His Val Thr Ser Leu Phe Gly Ala Ala Gln Leu Trp Glu Arg Gly Phe
            20                  25                  30

Thr Gly Arg Lys Val Lys Met Ala Ile Phe Asp Thr Gly Ile Arg Ala
        35                  40                  45

Asp His Pro His Phe Arg Asn Ile Lys Glu Arg Thr Asn Trp Thr Asn
    50                  55                  60

Glu Asp Thr Leu Asn Asp Asn Leu Gly His Gly Thr Phe Val Ala Gly
65                  70                  75                  80

Val Ile Ala Gly Gln Asp Pro Glu Cys Leu Gly Phe Ala Pro Asp Thr
                85                  90                  95

Glu Ile Tyr Ala Phe Arg Val Phe Thr Asp Ala Gln Cys Arg Tyr Pro
            100                 105                 110

Thr His His Gly Ser Trp Met His Leu Ile Met Leu Trp Leu Leu Val
        115                 120                 125

Trp Met Tyr Ile Val Leu Val Asp Leu Ile Thr Trp Ile Ser
130                 135                 140

Pro Leu Trp Lys Arg
145

<210> SEQ ID NO 5
<211> LENGTH: 2211
<212> TYPE: DNA
<213> ORGANISM: Arabidopsis thaliana

<400> SEQUENCE: 5
atggggatga ccgtcgtaat tattctggtg ttctcatttt tcgtagcgat tgtaacggcg      60
gagacctctc cttacatcat ccacatggac ttatccgcta aaccgttgcc attttccgat     120
catcggagct ggttttccac aactcttact tcagttataa ccaatagaaa accaaagatt     180
atctacgctt ataccgattc ggttcacggg tttagcgcgg ttctcaccaa ctctgagctc     240
caacgtctta aacacaaacc cgggtatgtc tcgttcacca agatttaccg gttaagcttc     300
cataccactt tctctccaaa gtttatcggt ttaaattcga catccggtac atggccggtc     360
tcgaattatg gagctggtat agtaatcggt attatagata ccggaatttg gcccgatagt     420
cccagctttc acgacgatgg ggttggttcg gttccgtcta atggaaagg agcatgtgaa      480 ttcaattctt cttccttgtg caacaagaaa ctaatcggtg ctaaggtatt caacaagggt     540
ttgttcgcca caaccctga tttgagagaa accaagattg ccaatactc ttcaccgtac       600 gatacaatcg acacggcac tcatgttgca gccattgcag ctgggaatca tgttaagaac      660
gcgtcttact tctcttacgc ccaaggaacc gcctcaggaa tcgcaccaca cgcgcatcta     720
gcaatctaca aagccgcgtg gaagaaggg atttactcat cagatgtaat cgcagcgatt      780
gatcaagcga ttcgagatgg agtccatgtg atatctctgt cgctaggatt gagttttgag     840
gatgatgacg acaatgatgg tttcggtcta gaaaatgatc caatcgcagt cgcatctttt     900
gcagcgattc aaaaaggcgt tttcgtggtt acttccggcg gtaacgacgg gccatattac     960
tggagtttga ttaacggagc gccgtggatt atgacggttg agcgggaac aattggtagg    1020 caatttcaag gaaccctaac gtttggaaac agagttagtg tcagttttcc atctctgttt   1080
cctggagagt tcccttcggt tcagtttcca gtaacttaca tcgaatctgg cagcgttgaa    1140
aacaagactc tcgcaaacag aattgttgtc tgtaacgaaa catataacat cggtagcaaa    1200
cttcatcaaa tcagatccac cggagctgca gcagtagttt taataacaga taagttactt    1260
```

```
gaggagcaag acacaataaa attccagttt ccagtagcat tcatcggctc aaaacaccga    1320
gaaactattg aaagctacgc atcaagcaac aaaaacaacg cgaccgcaaa gctggagttt    1380
cgtaaaacgg taatcgggac aaaaccagcg ccagaagttg cacatacag ctcaaggggt    1440 ccattcacaa gcttccctca aatcctgaaa ccagacattc tagctcctgg gacacttata    1500
ctctctgctt ggccgtcggt tgagcaaatc accggaactc gagcactacc gttattcagc    1560
ggattcaatc tcttaaccgg gacatcaatg gctgcacctc atgtagctgg agtcgctgcg    1620
cttataaagc aagtccatcc aaattggagt ccatcggcta aaaatctgc aattatgaca    1680 acggctttga ctttagacaa cccattagcc gttggagcag gcatgtgag tacgaacaaa    1740 gtcttaaacc ctggcctaat ctatgataca actccacaag atttcataaa cttcctttgt    1800
cacgaggcaa aacaatcaag aaaattgatc aatatcatca cgagatcgaa tatctccgac    1860
gcttgtaaaa agccatctcc atatctcaat taccctctcaa tcattgccta cttcacgtct    1920
gatcaaagca gtcccaagat ctttaagagg acattgacaa acgtgggaga agcaaagaga    1980
agctacatcg tgagagtgag aggcttgaag ggtctaaacg tcgtcgtaga gccaaagaaa    2040
ctaatgttca gcgagaaaaa cgagaagcta agctacactg tgagattgga gagtccaaga    2100
gggttacaag agaacgtggc ttatggattg gtgagttggg ttgatgaaga tgaagctgag    2160
tttgaagtga gctgttctgt ggtggccacg agccttgtcc aagagtcttg a            2211
```

<210> SEQ ID NO 6
<211> LENGTH: 736
<212> TYPE: PRT
<213> ORGANISM: Arabidopsis thaliana

<400> SEQUENCE: 6

```
Met Gly Met Thr Val Ile Ile Leu Val Phe Ser Phe Phe Val Ala
1               5                   10                  15

Ile Val Thr Ala Glu Thr Ser Pro Tyr Ile Ile His Met Asp Leu Ser
                20                  25                  30

Ala Lys Pro Leu Pro Phe Ser Asp His Arg Ser Trp Phe Ser Thr Thr
            35                  40                  45

Leu Thr Ser Val Ile Thr Asn Arg Lys Pro Lys Ile Ile Tyr Ala Tyr
        50                  55                  60

Thr Asp Ser Val His Gly Phe Ser Ala Val Leu Thr Asn Ser Glu Leu
65                  70                  75                  80

Gln Arg Leu Lys His Lys Pro Gly Tyr Val Ser Phe Thr Lys Asp Leu
                85                  90                  95

Pro Val Lys Leu His Thr Thr Phe Ser Pro Lys Phe Ile Gly Leu Asn
            100                 105                 110

Ser Thr Ser Gly Thr Trp Pro Val Ser Asn Tyr Gly Ala Gly Ile Val
        115                 120                 125

Ile Gly Ile Ile Asp Thr Gly Ile Trp Pro Asp Ser Pro Ser Phe His
    130                 135                 140

Asp Asp Gly Val Gly Ser Val Pro Ser Lys Trp Lys Gly Ala Cys Glu
145                 150                 155                 160

Phe Asn Ser Ser Ser Leu Cys Asn Lys Lys Leu Ile Gly Ala Lys Val
                165                 170                 175

Phe Asn Lys Gly Leu Phe Ala Asn Asn Pro Asp Leu Arg Glu Thr Lys
            180                 185                 190

Ile Gly Gln Tyr Ser Ser Pro Tyr Asp Thr Ile Gly His Gly Thr His
        195                 200                 205
```

-continued

Val Ala Ala Ile Ala Ala Gly Asn His Val Lys Asn Ala Ser Tyr Phe
      210                 215                 220

Ser Tyr Ala Gln Gly Thr Ala Ser Gly Ile Ala Pro His Ala His Leu
225                 230                 235                 240

Ala Ile Tyr Lys Ala Ala Trp Glu Glu Gly Ile Tyr Ser Ser Asp Val
                245                 250                 255

Ile Ala Ala Ile Asp Gln Ala Ile Arg Asp Gly Val His Val Ile Ser
              260                 265                 270

Leu Ser Leu Gly Leu Ser Phe Glu Asp Asp Asp Asn Asp Gly Phe
    275                 280                 285

Gly Leu Glu Asn Asp Pro Ile Ala Val Ala Ser Phe Ala Ala Ile Gln
    290                 295                 300

Lys Gly Val Phe Val Val Thr Ser Gly Gly Asn Asp Gly Pro Tyr Tyr
305                 310                 315                 320

Trp Ser Leu Ile Asn Gly Ala Pro Trp Ile Met Thr Val Gly Ala Gly
                325                 330                 335

Thr Ile Gly Arg Gln Phe Gln Gly Thr Leu Thr Phe Gly Asn Arg Val
              340                 345                 350

Ser Phe Ser Phe Pro Ser Leu Phe Pro Gly Glu Phe Pro Ser Val Gln
    355                 360                 365

Phe Pro Val Thr Tyr Ile Glu Ser Gly Ser Val Glu Asn Lys Thr Leu
    370                 375                 380

Ala Asn Arg Ile Val Val Cys Asn Glu Asn Ile Asn Ile Gly Ser Lys
385                 390                 395                 400

Leu His Gln Ile Arg Ser Thr Gly Ala Ala Val Val Leu Ile Thr
                405                 410                 415

Asp Lys Leu Leu Glu Glu Gln Asp Thr Ile Lys Phe Gln Phe Pro Val
              420                 425                 430

Ala Phe Ile Gly Ser Lys His Arg Glu Thr Ile Glu Ser Tyr Ala Ser
    435                 440                 445

Ser Asn Lys Asn Asn Ala Thr Ala Lys Leu Glu Phe Arg Lys Thr Val
    450                 455                 460

Ile Gly Thr Lys Pro Ala Pro Glu Val Gly Thr Tyr Ser Ser Arg Gly
465                 470                 475                 480

Pro Phe Thr Ser Phe Pro Gln Ile Leu Lys Pro Asp Ile Leu Ala Pro
                485                 490                 495

Gly Thr Leu Ile Leu Ser Ala Trp Pro Ser Val Glu Gln Ile Thr Gly
              500                 505                 510

Thr Arg Ala Leu Pro Leu Phe Ser Gly Phe Asn Leu Thr Gly Thr
    515                 520                 525

Ser Met Ala Ala Pro His Val Ala Gly Val Ala Ala Leu Ile Lys Gln
    530                 535                 540

Val His Pro Asn Trp Ser Pro Ser Ala Ile Lys Ser Ala Ile Met Thr
545                 550                 555                 560

Thr Ala Leu Thr Leu Asp Asn Pro Leu Ala Val Gly Ala Gly His Val
                565                 570                 575

Ser Thr Asn Lys Val Leu Asn Pro Gly Leu Ile Tyr Asp Thr Thr Pro
              580                 585                 590

Gln Asp Phe Ile Asn Phe Leu Cys His Glu Ala Lys Gln Ser Arg Lys
    595                 600                 605

Leu Ile Asn Ile Ile Thr Arg Ser Asn Ile Ser Asp Ala Cys Lys Lys
    610                 615                 620

Pro Ser Pro Tyr Leu Asn Tyr Pro Ser Ile Ile Ala Tyr Phe Thr Ser
625                 630                 635                 640

Asp Gln Ser Ser Pro Lys Ile Phe Lys Arg Thr Leu Thr Asn Val Gly
            645                 650                 655

Glu Ala Lys Arg Ser Tyr Ile Val Arg Val Arg Gly Leu Lys Gly Leu
        660                 665                 670

Asn Val Val Glu Pro Lys Lys Leu Met Phe Ser Glu Lys Asn Glu
        675                 680                 685

Lys Leu Ser Tyr Thr Val Arg Leu Glu Ser Pro Arg Gly Leu Gln Glu
    690                 695                 700

Asn Val Val Tyr Gly Leu Val Ser Trp Val Asp Glu Asp Glu Ala Glu
705                 710                 715                 720

Phe Glu Val Ser Cys Ser Val Val Ala Thr Ser Leu Val Gln Glu Ser
                725                 730                 735

<210> SEQ ID NO 7
<211> LENGTH: 2523
<212> TYPE: DNA
<213> ORGANISM: Arabidopsis thaliana

<400> SEQUENCE: 7

| | |
|---|---:|
| atggttagag taatgttggt gaggtttggg tttttattac ttatgatctc ttttgtgttt | 60 |
| ttgtctaata acactttggg acaacaacaa gacgatgatg atgattctgc tgtgtacatt | 120 |
| gtcacactta acaacctcc tattgtccat ctctttgaag aacaagagct taaacacaaa | 180 |
| aagtcaaagt ttacaccaaa attgcgacca aggaacaatt caaggaaacg tcatgggaag | 240 |
| tcaaagatac catctgttgt tcaatctcat gactcttct tgagaaagac tctaaaagga | 300 |
| gagaagtata taaagcttta tagttaccat tatcttatca atggatttgc tctgtttatt | 360 |
| aactcacaac aggctgagaa gctttcaatg agaaaagaag tagcaaacat agtgttggat | 420 |
| tactctgtta ggacagcaac aacttatact ccacagttta tgggtttacc acaaggagca | 480 |
| tgggtcaaag aagtggatt tgagattgct ggagaaggga ttataatcgg ttttatcgat | 540 |
| actgggatcg atccgaatca tcctagtttc aatgacaatg actctaagcg ttcatatcca | 600 |
| atccctaagc atttctcagg tgtttgtgaa gttacaccgg attttccatc aggatcttgc | 660 |
| aataagaagc ttattggagc acggcatttc gcgcaatccg ctgtaaccag aggaatctt | 720 |
| aactcatctg aagattacgc ttctcctttc gatggagatg gacatggaac acacacagct | 780 |
| tcggttgcag cgggtaacca cggagttcca gtgatagttt ctaaccataa ctttggatac | 840 |
| gctagtggaa tcgctcctcg tgcatttatt tctgtttaca aggcattgta taagagtttt | 900 |
| ggaggttttg ctgcagatgt tgtagcagct atagatcagg cagctcaaga tggagtagat | 960 |
| atattaagcc tatcaattac accgaatcgg aaacctcccg tgttgccac tttctttaat | 1020 |
| cctatcgaca tggcattact ttccgctgta aaagccggaa tcttcgtagt ccaagctgcg | 1080 |
| ggaaataccg gtccagcgcc taaaaccatg tcttcttta gtccttggat attcaccgtt | 1140 |
| ggtgcttctt ctcatgatag agtttactct aattctttaa ccttaggaaa caatgtaact | 1200 |
| attccaggca tgggattcgc aattcctaca gatagtggaa aaatgtacaa gatgatatct | 1260 |
| gcttttcatg ccttgaacaa tagtacttct gtagataaag atatgtatgt aggtgaatgt | 1320 |
| caagattatg aaaacttcga tcaagatcgt gtctcaggga acttttgat atgtagctac | 1380 |
| tctgctcgtt ttgttctcgg gctttcgact ataaaacaag ctttagatgt tgccaagaat | 1440 |
| ctatccgcga ctggtgtgat attctatata gaccccgtatg ttcttggttt tgagatcaat | 1500 |
| ccaacaccga tggatatgcc cgggatcata attccatctg tagaagattc caagactta | 1560 |
| ctcaagtact ataactcttc tattcaaaga gatgtaacca ctaaagaaat tgttagtttt | 1620 |

```
ggagcggttg cagccataga aggcggttta aatgctaact ttagtaacag agctcctaag    1680
gtaatgtatt actcagcaag aggacctgat cctgaagaca actcttttaa cgacgcagac    1740
gtattaaaac cgaacctcgt agcacctgga aactctattt ggggtgcttg gagttctgct    1800
tcaacggatt ctaccgagtt tgaaggtgag aaatttgcga tgatgtccgg tacaagtatg    1860
gctgctcctc atgtagctgg tgtggctgca ttaatcaaac aaagttatcc acagtttact    1920
ccttcaacaa tctcatccgc gctttcaaca acggctctcc taaatgataa taaaggcagt    1980
ccgataatgg ctcagcgaac ttattccaat cccgatcaaa gcctctatac cgcaacaccg    2040
tctgatatgg ggagcggttt tgttaacgca acggcagctt tagaccctgg tctagttttt    2100
gatacaagtt ttgaagatta tatatcattt ctttgtggga tcaacggctc ggatacggtg    2160
gtattcaact acaccggatt ccgctgtccc gctaacaaca caccagtcag tggttttgac    2220
ctcaatttgc catcaattac agtatcgaca cttagtggca cacaaacttt ccaaagatcg    2280
atgagaaaca tagccggcaa tgagacatac aatgttggtt ggagtcctcc ttatggtgtt    2340
tcaatgaaag tatcacctac tcaatttttct attgctatgg gagaaaatca agtacttagc    2400
gtaaccctca cggtgacaaa gaacagttcc agttctagtt ttggcagaat cggattgttt    2460
ggaaatacag gacacattgt taatattcct gtaactgtca tagcgaaaat cgcttcgagc    2520
tga                                                                  2523

<210> SEQ ID NO 8
<211> LENGTH: 798
<212> TYPE: PRT
<213> ORGANISM: Arabidopsis thaliana

<400> SEQUENCE: 8

Met Val Arg Val Met Leu Val Arg Phe Gly Phe Leu Leu Leu Met Ile
1               5                   10                  15

Ser Phe Val Phe Leu Ser Asn Asn Thr Leu Gly Gln Gln Gln Asp Asp
            20                  25                  30

Asp Asp Asp Ser Ala Val Tyr Ile Val Thr Leu Lys Gln Pro Pro Ile
        35                  40                  45

Val His Leu Phe Glu Glu Gln Glu Leu Lys His Lys Ser Lys Phe
    50                  55                  60

Thr Pro Lys Leu Arg Pro Arg Asn Asn Ser Lys Arg His Gly Lys
65                  70                  75                  80

Ser Lys Ile Pro Ser Val Val Gln Ser His Asp Ser Phe Leu Arg Lys
                85                  90                  95

Thr Leu Lys Gly Glu Lys Tyr Ile Lys Leu Tyr Ser Tyr His Tyr Leu
            100                 105                 110

Ile Asn Gly Phe Ala Leu Phe Ile Asn Ser Gln Gln Ala Glu Lys Leu
        115                 120                 125

Ser Met Arg Lys Glu Val Ala Asn Ile Val Leu Asp Tyr Ser Val Arg
    130                 135                 140

Thr Ala Thr Thr Tyr Thr Pro Gln Phe Met Gly Leu Pro Gln Gly Ala
145                 150                 155                 160

Trp Val Lys Glu Gly Gly Phe Glu Ile Ala Gly Glu Gly Val Ile Ile
                165                 170                 175

Gly Phe Ile Asp Thr Gly Ile Asp Pro Asn His Pro Ser Phe Asn Asp
            180                 185                 190

Asn Asp Ser Lys Arg Ser Tyr Pro Ile Pro Lys His Phe Ser Gly Val
        195                 200                 205
```

-continued

```
Cys Glu Val Thr Pro Asp Phe Pro Ser Gly Ser Cys Asn Lys Lys Leu
    210                 215                 220

Ile Gly Ala Arg His Phe Ala Gln Ser Ala Val Thr Arg Gly Ile Phe
225                 230                 235                 240

Asn Ser Ser Glu Asp Tyr Ala Ser Pro Phe Asp Gly Asp Gly His Gly
                245                 250                 255

Thr His Thr Ala Ser Val Ala Ala Gly Asn His Gly Val Pro Val Ile
            260                 265                 270

Val Ser Asn His Asn Phe Gly Tyr Ala Ser Gly Ile Ala Pro Arg Ala
        275                 280                 285

Phe Ile Ser Val Tyr Lys Ala Leu Tyr Lys Ser Phe Gly Gly Phe Ala
290                 295                 300

Ala Asp Val Val Ala Ala Ile Asp Gln Ala Ala Gln Asp Gly Val Asp
305                 310                 315                 320

Ile Leu Ser Leu Ser Ile Thr Pro Asn Arg Lys Pro Pro Gly Val Ala
                325                 330                 335

Thr Phe Phe Asn Pro Ile Asp Met Ala Leu Leu Ser Ala Val Lys Ala
            340                 345                 350

Gly Ile Phe Val Gln Ala Ala Gly Asn Thr Gly Pro Ala Pro Lys
        355                 360                 365

Thr Met Ser Ser Phe Ser Pro Trp Ile Phe Thr Val Gly Ala Ser Ser
    370                 375                 380

His Asp Arg Val Tyr Ser Asn Ser Leu Thr Leu Gly Asn Asn Val Thr
385                 390                 395                 400

Ile Pro Gly Met Gly Phe Ala Ile Pro Thr Asp Ser Gly Lys Met Tyr
                405                 410                 415

Lys Met Ile Ser Ala Phe His Ala Leu Asn Asn Ser Thr Ser Val Asp
            420                 425                 430

Lys Asp Met Tyr Val Gly Glu Cys Gln Asp Tyr Glu Asn Phe Asp Gln
        435                 440                 445

Asp Arg Val Ser Gly Lys Leu Leu Ile Cys Ser Tyr Ser Ala Arg Phe
450                 455                 460

Val Leu Gly Leu Ser Thr Ile Lys Gln Ala Leu Asp Val Ala Lys Asn
465                 470                 475                 480

Leu Ser Ala Thr Gly Val Ile Phe Tyr Ile Asp Pro Tyr Val Leu Gly
                485                 490                 495

Phe Glu Ile Asn Pro Thr Pro Met Asp Met Pro Gly Ile Ile Ile Pro
            500                 505                 510

Ser Val Glu Asp Ser Lys Thr Leu Leu Lys Tyr Tyr Asn Ser Ser Ile
        515                 520                 525

Gln Arg Asp Val Thr Thr Lys Glu Ile Val Ser Phe Gly Ala Val Ala
530                 535                 540

Ala Ile Glu Gly Gly Leu Asn Ala Asn Phe Ser Asn Arg Ala Pro Lys
545                 550                 555                 560

Val Met Tyr Tyr Ser Ala Arg Gly Pro Asp Pro Glu Asp Asn Ser Phe
                565                 570                 575

Asn Asp Ala Asp Val Leu Lys Pro Asn Leu Val Ala Pro Gly Asn Ser
            580                 585                 590

Ile Trp Gly Ala Trp Ser Ser Ala Ser Thr Asp Ser Thr Glu Phe Glu
        595                 600                 605

Gly Glu Lys Phe Ala Met Met Ser Gly Thr Ser Met Ala Ala Pro His
610                 615                 620

Val Ala Gly Val Ala Ala Leu Ile Lys Gln Ser Tyr Pro Gln Phe Thr
625                 630                 635                 640
```

```
Pro Ser Thr Ile Ser Ser Ala Leu Ser Thr Thr Ala Leu Leu Asn Asp
            645                 650                 655

Asn Lys Gly Ser Pro Ile Met Ala Gln Arg Thr Tyr Ser Asn Pro Asp
            660                 665                 670

Gln Ser Leu Tyr Thr Ala Thr Pro Ser Asp Met Gly Ser Gly Phe Val
            675                 680                 685

Asn Ala Thr Ala Ala Leu Asp Pro Gly Leu Val Phe Asp Thr Ser Phe
            690                 695                 700

Glu Asp Tyr Ile Ser Phe Leu Cys Gly Ile Asn Gly Ser Asp Thr Val
705                 710                 715                 720

Val Phe Asn Tyr Thr Gly Phe Arg Cys Pro Ala Asn Asn Thr Pro Val
                725                 730                 735

Ser Gly Phe Asp Leu Asn Leu Pro Ser Ile Thr Val Ser Thr Leu Ser
            740                 745                 750

Gly Thr Gln Thr Phe Gln Arg Ser Met Arg Asn Ile Ala Gly Asn Glu
            755                 760                 765

Thr Tyr Asn Val Gly Trp Ser Pro Pro Tyr Gly Val Ser Met Lys Val
            770                 775                 780

Ser Pro Thr Gln Phe Ser Ile Ala Met Gly Glu Asn Gln Val
785                 790                 795

<210> SEQ ID NO 9
<211> LENGTH: 276
<212> TYPE: DNA
<213> ORGANISM: Zea mays
<220> FEATURE:
<221> NAME/KEY: MISC_FEATURE
<222> LOCATION: (132)..(132)
<223> OTHER INFORMATION: n is a, c, g, or t

<400> SEQUENCE: 9
gatatatcca acaaccacgc agtgcataca tgcttgattt tcctgcccat cgatcatatc     60
gtcaactggt ccggcagttc tccgacacca tgagctcctc ggagtgcggc ggcggcggcg    120
gtcggcgcca anacgtcgtg gccggaggtg gtcgggctga gcgtggagga cgccaagaag    180
gtgatcctca aggacaagcc ggacgccgac atcgtggtgc tgcccgtcgg ctccgtggtg    240
accgtggatt atcgccctaa ccgtgtccgc atcttc                              276

<210> SEQ ID NO 10
<211> LENGTH: 91
<212> TYPE: PRT
<213> ORGANISM: Zea mays
<220> FEATURE:
<221> NAME/KEY: MISC_FEATURE
<222> LOCATION: (31)..(31)
<223> OTHER INFORMATION: A frameshift may occur immediately before
      position 31, resulting in an alternatively translated, shifted
      amino acid sequence.
<220> FEATURE:
<221> NAME/KEY: MISC_FEATURE
<222> LOCATION: (43)..(43)
<223> OTHER INFORMATION: Xaa is any amino acid

<400> SEQUENCE: 10

Asp Ile Ser Asn Asn His Ala Val His Thr Cys Leu Ile Phe Leu Pro
1               5                   10                  15

Ile Asp His Ile Val Asn Trp Ser Gly Ser Ser Pro Thr Pro Ala
            20                  25                  30

Pro Arg Ser Ala Ala Ala Ala Val Gly Ala Xaa Thr Ser Trp Pro
        35                  40                  45
```

```
            Glu Val Val Gly Leu Ser Val Glu Asp Ala Lys Lys Val Ile Leu Lys
             50                  55                  60

Asp Lys Pro Asp Ala Asp Ile Val Val Leu Pro Val Gly Ser Val Val
             65                  70                  75

Thr Val Asp Tyr Arg Pro Asn Arg Val Arg Ile Phe
             80                  85                  90

<210> SEQ ID NO 11
<211> LENGTH: 3792
<212> TYPE: DNA
<213> ORGANISM: Oryza sativa

<400> SEQUENCE: 11
atggcgccag atgagggcga cggctatcga tctacaccag catacgtcgg gttacagatc        60
gaactggcaa ccggcggcgc tgcgtgcaga caacggttgc taccgatcta catcaacaaa       120
tatcgtcggg ctacggatca gatcggcgac cggcggcctc acggtgcggt ctccgccccg       180
gactccggga ttgcaccgtg gattagggtt ctgggaggtg tgatggacaa aggggggaaag      240 aagaaggggg tggacctgga aggcctcttc ctaggtctta agctgtcccg ggaggaattg       300
agaggcatga aaggatcttg gtgccttgga gagaaggatg gcggaaaagt tcaacaggca       360
gtggggaagt tattctctcc acgagcaggg gtgtacaatc tgccgttcgg cttgatgaat       420
gtggatactg gccgggtaat tgggaataaa attgggaaag cattggaggt tgatacggat       480
gaggatgggt cagccgtggg aggttatctg ctggtgaagg tgctcatgga tgcccgcaaa       540
gccctaatcg gcggggtgat gatggagggt gtcgccggtg agaaggagaa ttggtgtgga       600
gtgaagtacg agttcctgcc aaatttttgt tattcctgcg gcgttctggg tcatgtggag       660
gagtgtgatg ataaggtatg gaaggaggaa gagcagcaat cggggactg gttgcgagtc       720 ctaccgatga acagcgggga tgtgcgaggc tggagctcgg aagggggcag ttctgggggt       780
tcgtttcagc acaggagtgt cgtatcctgg aggaaaagtg gagttgagaa ggaggtagc        840 agcggtgtag gtggaaaatc tgctagccgg gatgaccctg aactaaggga tgatgctgaa       900
agcccgggta aagggcatcc caagatccgg atgggcggtg ctccgaagaa gctgaccttt       960
gtcggtgatg gtagttcggg gagtttgact gaggagagag ggcataaaaa gctgctggag      1020
attacggctc cctcggagcc gcaactagtt ccgaccacgg tgaagtagc tagtgggtta       1080 gatggagagg acgctcgggg gaaggagcac agtaccatgc aggttcctgt gggggggagga      1140 gtaaaggaca acacactct cccgttggct gctgaaagtg gtactttgga tactgggcac      1200
tcggggacgg gagataagag gaaggccact ttcaagcggc gtccgcgagt gatggataag      1260
gaagtcggcg ccaaggagag cgcgattgct gatactcgaa agtgctctgt aacggaggag      1320
atggttgtga ccgaagaacg gaagaaacag aatgctcagg tggctgtgag tgatgacgct      1380
tccaagttcg tggccttctg gatatccaga gggaggagga tcccgatgtt ctgtttattt      1440
cggagacgaa aaaggtgga aggggagct cctcggtccg aaagttgtat ggccaagttt       1500
cgacaggctt tggaggactg ccagctgcat gatctgggtt ttgttgggga tgccttcacg      1560
tggaggaatc accatcacct ggcgtccaac tacataaagg aaagacttga tagagcagtg      1620
gccaatggtg cctggcgagc acgcttcccg cttgttcgcg taatcaatgg ggatccgcgc      1680
cactcagaca tcgttcggtc attgtggaaa ccggtgccac tgaaaaacaa caatgggggc      1740
aacctttgga gattatgcag aagtttgagg ctcgttggct ggaggaagaa gaatgccagg      1800
ccagagtgga ggaagcgtgg gagaatgcat tggaaggtgg tcaaactcgg ctaatgagaa      1860
tccaaagccg ggtcctgaag gaattatggg cttgggaccg cactgtcctg ggtgagttga      1920
```

```
agaagagggt taaaaatcta aggaaggaat tggagaagtg caggagggag ccaatctcta    1980
accggcaagt taacagagaa catttgttgc ggtacaagtt agagcggctg ctggatcaac    2040
aacatattta ctggaagcag cgagcacatt ctacctggtt aaccaagggc gaccggaaca    2100
caaagttttc catgcccaag catcggagaa gaagaaaaga aatacaatac agaagttgca    2160
ggatggccac ggtggtttgg ttgctggaaa tcaactaaaa agcttcattt cgaaccagta    2220
ccaacaactc tttaggtcga atgggtgctc tcagatggat gcagtattac aatgtgtcca    2280
agcgcgtgtg accccggaga tgagagaagg ccttgctgct ccttatcaga gagaggaagt    2340
ttgggtggct ttgaaggata tgggggattt aaaagcacca ggcgcagatg gtattccagc    2400
aatcttctac aaaaaatttt tgtcactagc tggcgataag gtgaaggatg aggtgctggc    2460
ggttcttaat ggtggggata tgccacaggg atggaacgat acagttgtgg tattaatacc    2520
aaagacgaaa cagccggaca cattgaaaga cttgagaccg ataagtttat gcaatgtggc    2580
atataaactg atctccaagg tgatagtcaa tcggttgaaa gttgtgctgc tggaaataat    2640
ctctccgtcc caaagtgcgt ttgtcccgag gaggttgatc acatacaatg tattactggc    2700
atatgagctc acacactact tgaatcaaag gaagaagggg aagaatggag tggctgcgat    2760
caagctggac atgagcaaag cttacgatag ggtggaatgg gatttcctgc gacacatgat    2820
gctgaggttg ggcttccatg atcagtgggt taacttagtc atgaagtgtg taacttctgt    2880
gacttaccgg atcaagatca atggggagca ctcagatcaa atatacccac agagggggct    2940
gaggcaggga gatccacttt cccttactt gttcattatt tgtgcggaag cctttcagc     3000
gctattacag aaagcacaag ctgatggaaa gatagagggt attaaagttt gcagggacac    3060
gccaagaata aaccatctct tttcgccga tgattccctt gtcctgatgc gagctggcca    3120
gaatgatgcg caagagttga aagggttct taacatatac gaagtggcat caggccaagt    3180
cataaacaag gacaaatcat ctgtcctctt cagcccaaac acacttcaga gtgataggat    3240
ggaagttaga tcagcgctat gtattaatca ggaggcaaaa aatgaaagat atcttggcct    3300
gcctgtctct attgggaagt caaggaggaa agcttttgag tatattaaga ggaaggtgtg    3360
gctccggatc cagggttggc aggagaaatt actatcaaaa gcagggaagg aaatccttgt    3420
caaagctgtg gcccaagcta ttcctaccta tgcgatgtca tgttttgatt tgactaaagg    3480
tttatgtgat gaaatcaatt ccatgattag caagtggtgg tggagccaga atgacaagga    3540
aaataaaata cactggctgt cgtgggagaa gatgacgctc cctaaaaagc ttggcgggcc    3600
aggattccgg gatcttcatc tgttcaacat ggcgatgctt gctcggcagg catggcggct    3660
cctcctaaat gtagactcgc tctgtgggca agtctttgtt gacgaaaaaa tcgaacacac    3720
cggcctggga gatctgctta gctcctgtgc aagtccaaag attgatgaga tgcgggcgtg    3780
ccagtcgttt ga                                                       3792
```

<210> SEQ ID NO 12
<211> LENGTH: 1264
<212> TYPE: PRT
<213> ORGANISM: Oryza sativa

<400> SEQUENCE: 12

Met Ala Pro Asp Glu Gly Asp Gly Tyr Arg Ser Thr Pro Ala Tyr Val
1               5                   10                  15

Gly Leu Gln Ile Glu Leu Ala Thr Gly Gly Ala Ala Cys Arg Gln Arg
            20                  25                  30

Leu Leu Pro Ile Tyr Ile Asn Lys Tyr Arg Arg Ala Thr Asp Gln Ile

```
                 35                  40                  45
Gly Asp Arg Arg Pro His Gly Ala Val Ser Ala Pro Asp Ser Gly Ile
 50                  55                  60

Ala Pro Trp Ile Arg Val Leu Gly Gly Val Met Asp Lys Gly Gly Lys
 65                  70                  75                  80

Lys Lys Gly Val Asp Leu Glu Gly Leu Phe Leu Gly Leu Lys Leu Ser
                 85                  90                  95

Arg Glu Glu Leu Arg Gly Met Lys Gly Ser Trp Cys Leu Glu Glu Lys
                100                 105                 110

Asp Gly Gly Lys Val Gln Gln Ala Val Gly Lys Leu Phe Ser Pro Arg
                115                 120                 125

Ala Gly Val Tyr Asn Leu Pro Phe Gly Leu Met Asn Val Asp Thr Gly
                130                 135                 140

Arg Val Ile Gly Asn Lys Ile Gly Lys Ala Leu Glu Val Asp Thr Asp
145                 150                 155                 160

Glu Asp Gly Ser Ala Val Gly Gly Tyr Leu Leu Val Lys Val Leu Met
                165                 170                 175

Asp Ala Arg Lys Ala Leu Ile Gly Gly Val Met Met Glu Gly Val Ala
                180                 185                 190

Gly Glu Lys Glu Asn Trp Cys Gly Val Lys Tyr Glu Phe Leu Pro Asn
                195                 200                 205

Phe Cys Tyr Ser Cys Gly Val Leu Gly His Val Glu Glu Cys Asp Asp
                210                 215                 220

Lys Val Trp Lys Glu Glu Gln Gln Phe Gly Asp Trp Leu Arg Val
225                 230                 235                 240

Leu Pro Met Lys Gln Arg Asp Val Arg Gly Trp Ser Glu Gly Gly
                245                 250                 255

Ser Ser Gly Gly Ser Phe Gln His Arg Ser Val Val Ser Trp Arg Lys
                260                 265                 270

Ser Gly Val Glu Lys Gly Ser Ser Val Gly Gly Lys Ser Ala
                275                 280                 285

Ser Arg Asp Asp Pro Glu Leu Arg Asp Asp Ala Glu Ser Pro Gly Lys
290                 295                 300

Gly His Pro Lys Ile Arg Met Gly Gly Ala Pro Lys Lys Leu Thr Phe
305                 310                 315                 320

Val Gly Asp Gly Ser Ser Gly Ser Leu Thr Glu Glu Arg Gly His Lys
                325                 330                 335

Lys Leu Leu Glu Ile Thr Ala Pro Ser Glu Pro Gln Leu Val Pro Thr
                340                 345                 350

Thr Gly Glu Val Ala Ser Gly Leu Asp Gly Glu Asp Ala Arg Gly Lys
                355                 360                 365

Glu His Ser Thr Met Gln Val Pro Val Gly Gly Val Lys Asp Lys
                370                 375                 380

His Thr Leu Pro Leu Ala Ala Glu Ser Gly Thr Leu Asp Thr Gly His
385                 390                 395                 400

Ser Gly Thr Gly Asp Lys Arg Lys Ala Thr Phe Lys Arg Arg Pro Arg
                405                 410                 415

Val Met Asp Lys Glu Val Gly Ala Lys Glu Ser Ala Ile Ala Asp Thr
                420                 425                 430

Arg Lys Cys Ser Val Thr Glu Glu Met Val Val Thr Glu Glu Arg Lys
                435                 440                 445

Lys Gln Asn Ala Gln Val Ala Val Ser Asp Asp Ala Ser Lys Phe Val
450                 455                 460
```

```
Ala Phe Trp Ile Ser Arg Gly Arg Arg Ile Pro Met Phe Cys Leu Phe
465                 470                 475                 480

Arg Arg Arg Lys Lys Val Glu Gly Gly Ala Pro Arg Ser Glu Ser Cys
                485                 490                 495

Met Ala Lys Phe Arg Gln Ala Leu Glu Asp Cys Gln Leu His Asp Leu
            500                 505                 510

Gly Phe Val Gly Asp Ala Phe Thr Trp Arg Asn His His Leu Ala
        515                 520                 525

Ser Asn Tyr Ile Lys Glu Arg Leu Asp Arg Ala Val Ala Asn Gly Ala
530                 535                 540

Trp Arg Ala Arg Phe Pro Leu Val Arg Val Ile Asn Gly Asp Pro Arg
545                 550                 555                 560

His Ser Asp His Arg Ser Val Ile Val Glu Thr Gly Ala Thr Glu Lys
                565                 570                 575

Gln Gln Trp Gly Gln Pro Leu Glu Ile Met Gln Lys Phe Glu Ala Arg
            580                 585                 590

Trp Leu Glu Glu Glu Cys Gln Ala Arg Val Glu Ala Trp Glu
        595                 600                 605

Asn Ala Leu Glu Gly Gly Gln Thr Arg Leu Met Glu Ile Gln Ser Arg
610                 615                 620

Val Leu Lys Glu Leu Trp Ala Trp Asp Arg Thr Val Leu Gly Glu Leu
625                 630                 635                 640

Lys Lys Arg Val Lys Asn Leu Arg Lys Glu Leu Lys Cys Arg Arg
                645                 650                 655

Glu Pro Ile Ser Asn Arg Gln Val Asn Arg Gly His Leu Leu Arg Tyr
            660                 665                 670

Lys Leu Glu Arg Leu Leu Asp Gln Gln His Ile Tyr Trp Lys Gln Arg
        675                 680                 685

Ala His Ser Thr Trp Leu Thr Lys Gly Asp Arg Asn Thr Lys Phe Phe
        690                 695                 700

His Ala Gln Ala Ser Glu Lys Lys Arg Asn Thr Ile Gln Lys Leu
705                 710                 715                 720

Gln Asp Gly His Gly Gly Leu Val Ala Gly Asn Gln Leu Lys Ser Phe
            725                 730                 735

Ile Ser Asn Gln Tyr Gln Gln Leu Phe Arg Ser Asn Gly Cys Ser Gln
            740                 745                 750

Met Asp Ala Val Leu Gln Cys Val Gln Ala Arg Val Thr Pro Glu Met
        755                 760                 765

Arg Glu Gly Leu Ala Ala Pro Tyr Gln Arg Glu Val Trp Val Ala
770                 775                 780

Leu Lys Asp Met Gly Asp Leu Lys Ala Pro Gly Ala Asp Gly Ile Pro
785                 790                 795                 800

Ala Ile Phe Tyr Lys Lys Phe Leu Ser Leu Ala Gly Asp Lys Val Lys
                805                 810                 815

Asp Glu Val Leu Ala Val Leu Asn Gly Gly Asp Met Pro Gln Gly Trp
            820                 825                 830

Asn Asp Thr Val Val Leu Ile Pro Lys Thr Lys Gln Pro Asp Thr
            835                 840                 845

Leu Lys Asp Leu Arg Pro Ile Ser Leu Cys Asn Val Ala Tyr Lys Leu
850                 855                 860

Ile Ser Lys Val Ile Val Asn Arg Leu Lys Val Val Leu Glu Ile
865                 870                 875                 880

Ile Ser Pro Ser Gln Ser Ala Phe Val Pro Arg Arg Leu Ile Thr Tyr
                885                 890                 895
```

```
Asn Val Leu Leu Ala Tyr Glu Leu Thr His Tyr Leu Asn Gln Arg Lys
            900                 905                 910
Lys Gly Lys Asn Gly Val Ala Ala Ile Lys Leu Asp Met Ser Lys Ala
        915                 920                 925
Tyr Asp Arg Val Glu Trp Asp Phe Leu Arg His Met Met Leu Arg Leu
    930                 935                 940
Gly Phe His Asp Gln Trp Val Asn Leu Val Met Lys Cys Val Thr Ser
945                 950                 955                 960
Val Thr Tyr Arg Ile Lys Ile Asn Gly Glu His Ser Asp Gln Ile Tyr
                965                 970                 975
Pro Gln Arg Gly Leu Arg Gln Gly Asp Pro Leu Ser Pro Tyr Leu Phe
            980                 985                 990
Ile Ile Cys Ala Glu Gly Leu Ser Ala Leu Leu Gln Lys Ala Gln Ala
        995                 1000                1005
Asp Gly Lys Ile Glu Gly Ile Lys Val Cys Arg Asp Thr Pro Arg
        1010                1015                1020
Ile Asn His Leu Phe Phe Ala Asp Asp Ser Leu Val Leu Met Arg
        1025                1030                1035
Ala Gly Gln Asn Asp Ala Gln Glu Leu Arg Arg Val Leu Asn Ile
        1040                1045                1050
Tyr Glu Val Ala Ser Gly Gln Val Ile Asn Lys Asp Lys Ser Ser
        1055                1060                1065
Val Leu Phe Ser Pro Asn Thr Leu Gln Ser Asp Arg Met Glu Val
        1070                1075                1080
Arg Ser Ala Leu Cys Ile Asn Gln Glu Ala Lys Asn Glu Arg Tyr
        1085                1090                1095
Leu Gly Leu Pro Val Ser Ile Gly Lys Ser Arg Arg Lys Ala Phe
        1100                1105                1110
Glu Tyr Ile Lys Arg Lys Val Trp Leu Arg Ile Gln Gly Trp Gln
        1115                1120                1125
Glu Lys Leu Leu Ser Lys Ala Gly Lys Glu Ile Leu Val Lys Ala
        1130                1135                1140
Val Ala Gln Ala Ile Pro Thr Tyr Ala Met Ser Cys Phe Asp Leu
        1145                1150                1155
Thr Lys Gly Leu Cys Asp Glu Ile Asn Ser Met Ile Ser Lys Trp
        1160                1165                1170
Trp Trp Ser Gln Asn Asp Lys Glu Asn Lys Ile His Trp Leu Ser
        1175                1180                1185
Trp Glu Lys Met Thr Leu Pro Lys Lys Leu Gly Gly Pro Gly Phe
        1190                1195                1200
Arg Asp Leu His Leu Phe Asn Met Ala Met Leu Ala Arg Gln Ala
        1205                1210                1215
Trp Arg Leu Leu Leu Asn Val Asp Ser Leu Cys Gly Gln Val Phe
        1220                1225                1230
Val Asp Glu Lys Ile Glu His Thr Gly Leu Gly Asp Leu Leu Ser
        1235                1240                1245
Ser Cys Ala Ser Pro Lys Ile Asp Glu Met Arg Ala Cys Gln Ser
        1250                1255                1260
Val

<210> SEQ ID NO 13
<211> LENGTH: 823
<212> TYPE: PRT
<213> ORGANISM: Artificial Sequence
```

```
<220> FEATURE:
<223> OTHER INFORMATION: Description of Artificial Sequence: Consensus
      Sequence
<220> FEATURE:
<221> NAME/KEY: misc_feature
<222> LOCATION: (1)..(10)
<223> OTHER INFORMATION: Xaa can be any amino acid
<220> FEATURE:
<221> NAME/KEY: misc_feature
<222> LOCATION: (12)..(49)
<223> OTHER INFORMATION: Xaa can be any amino acid
<220> FEATURE:
<221> NAME/KEY: misc_feature
<222> LOCATION: (51)..(91)
<223> OTHER INFORMATION: Xaa can be any amino acid
<220> FEATURE:
<221> NAME/KEY: misc_feature
<222> LOCATION: (93)..(112)
<223> OTHER INFORMATION: Xaa can be any amino acid
<220> FEATURE:
<221> NAME/KEY: misc_feature
<222> LOCATION: (114)..(115)
<223> OTHER INFORMATION: Xaa can be any amino acid
<220> FEATURE:
<221> NAME/KEY: misc_feature
<222> LOCATION: (117)..(124)
<223> OTHER INFORMATION: Xaa can be any amino acid
<220> FEATURE:
<221> NAME/KEY: misc_feature
<222> LOCATION: (126)..(165)
<223> OTHER INFORMATION: Xaa can be any amino acid
<220> FEATURE:
<221> NAME/KEY: misc_feature
<222> LOCATION: (167)..(193)
<223> OTHER INFORMATION: Xaa can be any amino acid
<220> FEATURE:
<221> NAME/KEY: misc_feature
<222> LOCATION: (195)..(196)
<223> OTHER INFORMATION: Xaa can be any amino acid
<220> FEATURE:
<221> NAME/KEY: misc_feature
<222> LOCATION: (201)..(202)
<223> OTHER INFORMATION: Xaa can be any amino acid
<220> FEATURE:
<221> NAME/KEY: misc_feature
<222> LOCATION: (204)..(206)
<223> OTHER INFORMATION: Xaa can be any amino acid
<220> FEATURE:
<221> NAME/KEY: misc_feature
<222> LOCATION: (209)..(225)
<223> OTHER INFORMATION: Xaa can be any amino acid
<220> FEATURE:
<221> NAME/KEY: misc_feature
<222> LOCATION: (227)..(227)
<223> OTHER INFORMATION: Xaa can be any amino acid
<220> FEATURE:
<221> NAME/KEY: misc_feature
<222> LOCATION: (230)..(252)
<223> OTHER INFORMATION: Xaa can be any amino acid
<220> FEATURE:
<221> NAME/KEY: misc_feature
<222> LOCATION: (254)..(256)
<223> OTHER INFORMATION: Xaa can be any amino acid
<220> FEATURE:
<221> NAME/KEY: misc_feature
<222> LOCATION: (258)..(260)
<223> OTHER INFORMATION: Xaa can be any amino acid
<220> FEATURE:
<221> NAME/KEY: misc_feature
<222> LOCATION: (262)..(266)
<223> OTHER INFORMATION: Xaa can be any amino acid
<220> FEATURE:
<221> NAME/KEY: misc_feature
<222> LOCATION: (269)..(303)
<223> OTHER INFORMATION: Xaa can be any amino acid
<220> FEATURE:
<221> NAME/KEY: misc_feature
<222> LOCATION: (305)..(307)
<223> OTHER INFORMATION: Xaa can be any amino acid
<220> FEATURE:
```

```
<221> NAME/KEY: misc_feature
<222> LOCATION: (310)..(310)
<223> OTHER INFORMATION: Xaa can be any amino acid
<220> FEATURE:
<221> NAME/KEY: misc_feature
<222> LOCATION: (313)..(327)
<223> OTHER INFORMATION: Xaa can be any amino acid
<220> FEATURE:
<221> NAME/KEY: misc_feature
<222> LOCATION: (329)..(517)
<223> OTHER INFORMATION: Xaa can be any amino acid
<220> FEATURE:
<221> NAME/KEY: misc_feature
<222> LOCATION: (519)..(525)
<223> OTHER INFORMATION: Xaa can be any amino acid
<220> FEATURE:
<221> NAME/KEY: misc_feature
<222> LOCATION: (527)..(545)
<223> OTHER INFORMATION: Xaa can be any amino acid
<220> FEATURE:
<221> NAME/KEY: misc_feature
<222> LOCATION: (547)..(578)
<223> OTHER INFORMATION: Xaa can be any amino acid
<220> FEATURE:
<221> NAME/KEY: misc_feature
<222> LOCATION: (580)..(582)
<223> OTHER INFORMATION: Xaa can be any amino acid
<220> FEATURE:
<221> NAME/KEY: misc_feature
<222> LOCATION: (584)..(586)
<223> OTHER INFORMATION: Xaa can be any amino acid
<220> FEATURE:
<221> NAME/KEY: misc_feature
<222> LOCATION: (588)..(660)
<223> OTHER INFORMATION: Xaa can be any amino acid
<220> FEATURE:
<221> NAME/KEY: misc_feature
<222> LOCATION: (662)..(755)
<223> OTHER INFORMATION: Xaa can be any amino acid
<220> FEATURE:
<221> NAME/KEY: misc_feature
<222> LOCATION: (757)..(795)
<223> OTHER INFORMATION: Xaa can be any amino acid
<220> FEATURE:
<221> NAME/KEY: misc_feature
<222> LOCATION: (797)..(823)
<223> OTHER INFORMATION: Xaa can be any amino acid

<400> SEQUENCE: 13

Xaa Xaa Xaa Xaa Xaa Xaa Xaa Xaa Xaa Arg Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Phe Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Leu Xaa Xaa Xaa Xaa
            85                  90                  95

Xaa Xaa Xaa Xaa Xaa Xaa Xaa Xaa Xaa Xaa Xaa Xaa Xaa Xaa Xaa
        100                 105                 110

Gly Xaa Xaa Asp Xaa Xaa Xaa Xaa Xaa Xaa Xaa Ser Xaa Xaa Xaa
    115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa
145                 150                 155                 160
```

-continued

```
Xaa Xaa Xaa Xaa Xaa Phe Xaa Xaa Xaa Xaa Xaa Xaa Xaa Xaa
                165             170             175

Xaa Xaa Xaa Xaa Xaa Xaa Xaa Xaa Xaa Xaa Xaa Xaa Xaa Xaa
            180             185             190

Xaa Asp Xaa Xaa Gly His Gly Thr Xaa Xaa Ala Xaa Xaa Xaa Ala Gly
        195             200             205

Xaa Xaa Xaa Xaa Xaa Xaa Xaa Xaa Xaa Xaa Xaa Xaa Xaa Xaa
    210             215             220

Xaa Gly Xaa Ala Pro Xaa Xaa Xaa Xaa Xaa Xaa Xaa Xaa Xaa
225             230             235             240

Xaa Xaa Xaa Xaa Xaa Xaa Xaa Xaa Xaa Xaa Xaa Ala Xaa Xaa Xaa
                245             250             255

Ala Xaa Xaa Xaa Gly Xaa Xaa Xaa Xaa Xaa Leu Ser Xaa Xaa Xaa Xaa
        260             265             270

Xaa Xaa Xaa Xaa Xaa Xaa Xaa Xaa Xaa Xaa Xaa Xaa Xaa Xaa
            275             280             285

Xaa Xaa Xaa Xaa Xaa Xaa Xaa Xaa Xaa Xaa Xaa Xaa Xaa Val
        290             295             300

Xaa Xaa Xaa Gly Asn Xaa Gly Pro Xaa Xaa Xaa Xaa Xaa Xaa
305             310             315             320

Xaa Xaa Xaa Xaa Xaa Xaa Xaa Gly Xaa Xaa Xaa Xaa Xaa Xaa
                325             330             335

Xaa Xaa Xaa Xaa Xaa Xaa Xaa Xaa Xaa Xaa Xaa Xaa Xaa Xaa
            340             345             350

Xaa Xaa Xaa Xaa Xaa Xaa Xaa Xaa Xaa Xaa Xaa Xaa Xaa Xaa
        355             360             365

Xaa Xaa Xaa Xaa Xaa Xaa Xaa Xaa Xaa Xaa Xaa Xaa Xaa Xaa
    370             375             380

Xaa Xaa Xaa Xaa Xaa Xaa Xaa Xaa Xaa Xaa Xaa Xaa Xaa Xaa Xaa
385             390             395             400

Xaa Xaa Xaa Xaa Xaa Xaa Xaa Xaa Xaa Xaa Xaa Xaa Xaa Xaa
                405             410             415

Xaa Xaa Xaa Xaa Xaa Xaa Xaa Xaa Xaa Xaa Xaa Xaa Xaa Xaa
            420             425             430

Xaa Xaa Xaa Xaa Xaa Xaa Xaa Xaa Xaa Xaa Xaa Xaa Xaa Xaa
        435             440             445

Xaa Xaa Xaa Xaa Xaa Xaa Xaa Xaa Xaa Xaa Xaa Xaa Xaa Xaa
    450             455             460

Xaa Xaa Xaa Xaa Xaa Xaa Xaa Xaa Xaa Xaa Xaa Xaa Xaa Xaa Xaa
465             470             475             480

Xaa Xaa Xaa Xaa Xaa Xaa Xaa Xaa Xaa Xaa Xaa Xaa Xaa Xaa
                485             490             495

Xaa Xaa Xaa Xaa Xaa Xaa Xaa Xaa Xaa Xaa Xaa Xaa Xaa Xaa
            500             505             510

Xaa Xaa Xaa Xaa Xaa Val Xaa Xaa Xaa Xaa Xaa Pro Xaa Xaa
        515             520             525

Xaa Xaa Xaa Xaa Xaa Xaa Xaa Xaa Xaa Xaa Xaa Xaa Xaa Xaa
    530             535             540

Xaa Pro Xaa Xaa Xaa Xaa Xaa Xaa Xaa Xaa Xaa Xaa Xaa Xaa Xaa
545             550             555             560

Xaa Xaa Xaa Xaa Xaa Xaa Xaa Xaa Xaa Xaa Xaa Xaa Xaa Xaa
                565             570             575

Xaa Xaa Ser Xaa Xaa Xaa Pro Xaa Xaa Xaa Gly Xaa Xaa Xaa Xaa Xaa
        580             585             590
```

Xaa Xaa Xaa Xaa Xaa Xaa Xaa Xaa Xaa Xaa Xaa Xaa Xaa Xaa Xaa
        595                 600                 605

Xaa Xaa Xaa Xaa Xaa Xaa Xaa Xaa Xaa Xaa Xaa Xaa Xaa Xaa Xaa
        610                 615                 620

Xaa Xaa Xaa Xaa Xaa Xaa Xaa Xaa Xaa Xaa Xaa Xaa Xaa Xaa Xaa
625                 630                 635                 640

Xaa Xaa Xaa Xaa Xaa Xaa Xaa Xaa Xaa Xaa Xaa Xaa Xaa Xaa Xaa
        645                 650                 655

Xaa Xaa Xaa Xaa Asp Xaa Xaa Xaa Xaa Xaa Xaa Xaa Xaa Xaa Xaa
        660                 665                 670

Xaa Xaa Xaa Xaa Xaa Xaa Xaa Xaa Xaa Xaa Xaa Xaa Xaa Xaa Xaa
        675                 680                 685

Xaa Xaa Xaa Xaa Xaa Xaa Xaa Xaa Xaa Xaa Xaa Xaa Xaa Xaa Xaa
        690                 695                 700

Xaa Xaa Xaa Xaa Xaa Xaa Xaa Xaa Xaa Xaa Xaa Xaa Xaa Xaa Xaa
705                 710                 715                 720

Xaa Xaa Xaa Xaa Xaa Xaa Xaa Xaa Xaa Xaa Xaa Xaa Xaa Xaa Xaa
        725                 730                 735

Xaa Xaa Xaa Xaa Xaa Xaa Xaa Xaa Xaa Xaa Xaa Xaa Xaa Xaa Xaa
        740                 745                 750

Xaa Xaa Xaa Pro Xaa Xaa Xaa Xaa Xaa Xaa Xaa Xaa Xaa Xaa Xaa
        755                 760                 765

Xaa Xaa Xaa Xaa Xaa Xaa Xaa Xaa Xaa Xaa Xaa Xaa Xaa Xaa Xaa
        770                 775                 780

Xaa Xaa Xaa Xaa Xaa Xaa Xaa Xaa Xaa Xaa Gly Xaa Xaa Xaa Xaa
785                 790                 795                 800

Xaa Xaa Xaa Xaa Xaa Xaa Xaa Xaa Xaa Xaa Xaa Xaa Xaa Xaa Xaa
        805                 810                 815

Xaa Xaa Xaa Xaa Xaa Xaa Xaa
        820

<210> SEQ ID NO 14
<211> LENGTH: 822
<212> TYPE: PRT
<213> ORGANISM: Artificial Sequence
<220> FEATURE:
<223> OTHER INFORMATION: Description of Artificial Sequence: Consensus
      Sequence
<220> FEATURE:
<221> NAME/KEY: misc_feature
<222> LOCATION: (2)..(2)
<223> OTHER INFORMATION: Xaa can be any amino acid
<220> FEATURE:
<221> NAME/KEY: misc_feature
<222> LOCATION: (6)..(6)
<223> OTHER INFORMATION: Xaa can be any amino acid
<220> FEATURE:
<221> NAME/KEY: misc_feature
<222> LOCATION: (11)..(13)
<223> OTHER INFORMATION: Xaa can be any amino acid
<220> FEATURE:
<221> NAME/KEY: misc_feature
<222> LOCATION: (15)..(16)
<223> OTHER INFORMATION: Xaa can be any amino acid
<220> FEATURE:
<221> NAME/KEY: misc_feature
<222> LOCATION: (18)..(19)
<223> OTHER INFORMATION: Xaa can be any amino acid
<220> FEATURE:
<221> NAME/KEY: misc_feature
<222> LOCATION: (21)..(39)
<223> OTHER INFORMATION: Xaa can be any amino acid
<220> FEATURE:
<221> NAME/KEY: misc_feature

```
<222> LOCATION: (41)..(41)
<223> OTHER INFORMATION: Xaa can be any amino acid
<220> FEATURE:
<221> NAME/KEY: misc_feature
<222> LOCATION: (43)..(47)
<223> OTHER INFORMATION: Xaa can be any amino acid
<220> FEATURE:
<221> NAME/KEY: misc_feature
<222> LOCATION: (51)..(60)
<223> OTHER INFORMATION: Xaa can be any amino acid
<220> FEATURE:
<221> NAME/KEY: misc_feature
<222> LOCATION: (62)..(62)
<223> OTHER INFORMATION: Xaa can be any amino acid
<220> FEATURE:
<221> NAME/KEY: misc_feature
<222> LOCATION: (65)..(66)
<223> OTHER INFORMATION: Xaa can be any amino acid
<220> FEATURE:
<221> NAME/KEY: misc_feature
<222> LOCATION: (68)..(72)
<223> OTHER INFORMATION: Xaa can be any amino acid
<220> FEATURE:
<221> NAME/KEY: misc_feature
<222> LOCATION: (75)..(75)
<223> OTHER INFORMATION: Xaa can be any amino acid
<220> FEATURE:
<221> NAME/KEY: misc_feature
<222> LOCATION: (77)..(80)
<223> OTHER INFORMATION: Xaa can be any amino acid
<220> FEATURE:
<221> NAME/KEY: misc_feature
<222> LOCATION: (84)..(84)
<223> OTHER INFORMATION: Xaa can be any amino acid
<220> FEATURE:
<221> NAME/KEY: misc_feature
<222> LOCATION: (87)..(87)
<223> OTHER INFORMATION: Xaa can be any amino acid
<220> FEATURE:
<221> NAME/KEY: misc_feature
<222> LOCATION: (89)..(89)
<223> OTHER INFORMATION: Xaa can be any amino acid
<220> FEATURE:
<221> NAME/KEY: misc_feature
<222> LOCATION: (92)..(105)
<223> OTHER INFORMATION: Xaa can be any amino acid
<220> FEATURE:
<221> NAME/KEY: misc_feature
<222> LOCATION: (109)..(110)
<223> OTHER INFORMATION: Xaa can be any amino acid
<220> FEATURE:
<221> NAME/KEY: misc_feature
<222> LOCATION: (113)..(113)
<223> OTHER INFORMATION: Xaa can be any amino acid
<220> FEATURE:
<221> NAME/KEY: misc_feature
<222> LOCATION: (119)..(119)
<223> OTHER INFORMATION: Xaa can be any amino acid
<220> FEATURE:
<221> NAME/KEY: misc_feature
<222> LOCATION: (122)..(122)
<223> OTHER INFORMATION: Xaa can be any amino acid
<220> FEATURE:
<221> NAME/KEY: misc_feature
<222> LOCATION: (126)..(126)
<223> OTHER INFORMATION: Xaa can be any amino acid
<220> FEATURE:
<221> NAME/KEY: misc_feature
<222> LOCATION: (128)..(128)
<223> OTHER INFORMATION: Xaa can be any amino acid
<220> FEATURE:
<221> NAME/KEY: misc_feature
<222> LOCATION: (130)..(131)
<223> OTHER INFORMATION: Xaa can be any amino acid
<220> FEATURE:
<221> NAME/KEY: misc_feature
<222> LOCATION: (133)..(136)
<223> OTHER INFORMATION: Xaa can be any amino acid
<220> FEATURE:
<221> NAME/KEY: misc_feature
```

```
<222> LOCATION: (138)..(141)
<223> OTHER INFORMATION: Xaa can be any amino acid
<220> FEATURE:
<221> NAME/KEY: misc_feature
<222> LOCATION: (143)..(143)
<223> OTHER INFORMATION: Xaa can be any amino acid
<220> FEATURE:
<221> NAME/KEY: misc_feature
<222> LOCATION: (146)..(154)
<223> OTHER INFORMATION: Xaa can be any amino acid
<220> FEATURE:
<221> NAME/KEY: misc_feature
<222> LOCATION: (163)..(164)
<223> OTHER INFORMATION: Xaa can be any amino acid
<220> FEATURE:
<221> NAME/KEY: misc_feature
<222> LOCATION: (166)..(167)
<223> OTHER INFORMATION: Xaa can be any amino acid
<220> FEATURE:
<221> NAME/KEY: misc_feature
<222> LOCATION: (169)..(170)
<223> OTHER INFORMATION: Xaa can be any amino acid
<220> FEATURE:
<221> NAME/KEY: misc_feature
<222> LOCATION: (172)..(178)
<223> OTHER INFORMATION: Xaa can be any amino acid
<220> FEATURE:
<221> NAME/KEY: misc_feature
<222> LOCATION: (180)..(189)
<223> OTHER INFORMATION: Xaa can be any amino acid
<220> FEATURE:
<221> NAME/KEY: misc_feature
<222> LOCATION: (192)..(192)
<223> OTHER INFORMATION: Xaa can be any amino acid
<220> FEATURE:
<221> NAME/KEY: misc_feature
<222> LOCATION: (194)..(195)
<223> OTHER INFORMATION: Xaa can be any amino acid
<220> FEATURE:
<221> NAME/KEY: misc_feature
<222> LOCATION: (203)..(203)
<223> OTHER INFORMATION: Xaa can be any amino acid
<220> FEATURE:
<221> NAME/KEY: misc_feature
<222> LOCATION: (210)..(220)
<223> OTHER INFORMATION: Xaa can be any amino acid
<220> FEATURE:
<221> NAME/KEY: misc_feature
<222> LOCATION: (222)..(222)
<223> OTHER INFORMATION: Xaa can be any amino acid
<220> FEATURE:
<221> NAME/KEY: misc_feature
<222> LOCATION: (229)..(229)
<223> OTHER INFORMATION: Xaa can be any amino acid
<220> FEATURE:
<221> NAME/KEY: misc_feature
<222> LOCATION: (231)..(231)
<223> OTHER INFORMATION: Xaa can be any amino acid
<220> FEATURE:
<221> NAME/KEY: misc_feature
<222> LOCATION: (233)..(234)
<223> OTHER INFORMATION: Xaa can be any amino acid
<220> FEATURE:
<221> NAME/KEY: misc_feature
<222> LOCATION: (238)..(244)
<223> OTHER INFORMATION: Xaa can be any amino acid
<220> FEATURE:
<221> NAME/KEY: misc_feature
<222> LOCATION: (246)..(246)
<223> OTHER INFORMATION: Xaa can be any amino acid
<220> FEATURE:
<221> NAME/KEY: misc_feature
<222> LOCATION: (250)..(250)
<223> OTHER INFORMATION: Xaa can be any amino acid
<220> FEATURE:
<221> NAME/KEY: misc_feature
<222> LOCATION: (257)..(258)
<223> OTHER INFORMATION: Xaa can be any amino acid
<220> FEATURE:
<221> NAME/KEY: misc_feature
```

```
<222> LOCATION: (270)..(274)
<223> OTHER INFORMATION: Xaa can be any amino acid
<220> FEATURE:
<221> NAME/KEY: misc_feature
<222> LOCATION: (276)..(280)
<223> OTHER INFORMATION: Xaa can be any amino acid
<220> FEATURE:
<221> NAME/KEY: misc_feature
<222> LOCATION: (282)..(284)
<223> OTHER INFORMATION: Xaa can be any amino acid
<220> FEATURE:
<221> NAME/KEY: misc_feature
<222> LOCATION: (286)..(286)
<223> OTHER INFORMATION: Xaa can be any amino acid
<220> FEATURE:
<221> NAME/KEY: misc_feature
<222> LOCATION: (289)..(290)
<223> OTHER INFORMATION: Xaa can be any amino acid
<220> FEATURE:
<221> NAME/KEY: misc_feature
<222> LOCATION: (292)..(294)
<223> OTHER INFORMATION: Xaa can be any amino acid
<220> FEATURE:
<221> NAME/KEY: misc_feature
<222> LOCATION: (296)..(298)
<223> OTHER INFORMATION: Xaa can be any amino acid
<220> FEATURE:
<221> NAME/KEY: misc_feature
<222> LOCATION: (304)..(304)
<223> OTHER INFORMATION: Xaa can be any amino acid
<220> FEATURE:
<221> NAME/KEY: misc_feature
<222> LOCATION: (306)..(306)
<223> OTHER INFORMATION: Xaa can be any amino acid
<220> FEATURE:
<221> NAME/KEY: misc_feature
<222> LOCATION: (312)..(312)
<223> OTHER INFORMATION: Xaa can be any amino acid
<220> FEATURE:
<221> NAME/KEY: misc_feature
<222> LOCATION: (314)..(314)
<223> OTHER INFORMATION: Xaa can be any amino acid
<220> FEATURE:
<221> NAME/KEY: misc_feature
<222> LOCATION: (317)..(317)
<223> OTHER INFORMATION: Xaa can be any amino acid
<220> FEATURE:
<221> NAME/KEY: misc_feature
<222> LOCATION: (319)..(319)
<223> OTHER INFORMATION: Xaa can be any amino acid
<220> FEATURE:
<221> NAME/KEY: misc_feature
<222> LOCATION: (324)..(324)
<223> OTHER INFORMATION: Xaa can be any amino acid
<220> FEATURE:
<221> NAME/KEY: misc_feature
<222> LOCATION: (330)..(330)
<223> OTHER INFORMATION: Xaa can be any amino acid
<220> FEATURE:
<221> NAME/KEY: misc_feature
<222> LOCATION: (334)..(338)
<223> OTHER INFORMATION: Xaa can be any amino acid
<220> FEATURE:
<221> NAME/KEY: misc_feature
<222> LOCATION: (341)..(341)
<223> OTHER INFORMATION: Xaa can be any amino acid
<220> FEATURE:
<221> NAME/KEY: misc_feature
<222> LOCATION: (344)..(344)
<223> OTHER INFORMATION: Xaa can be any amino acid
<220> FEATURE:
<221> NAME/KEY: misc_feature
<222> LOCATION: (347)..(354)
<223> OTHER INFORMATION: Xaa can be any amino acid
<220> FEATURE:
<221> NAME/KEY: misc_feature
<222> LOCATION: (356)..(360)
<223> OTHER INFORMATION: Xaa can be any amino acid
<220> FEATURE:
<221> NAME/KEY: misc_feature
```

```
<222> LOCATION: (362)..(367)
<223> OTHER INFORMATION: Xaa can be any amino acid
<220> FEATURE:
<221> NAME/KEY: misc_feature
<222> LOCATION: (369)..(373)
<223> OTHER INFORMATION: Xaa can be any amino acid
<220> FEATURE:
<221> NAME/KEY: misc_feature
<222> LOCATION: (376)..(391)
<223> OTHER INFORMATION: Xaa can be any amino acid
<220> FEATURE:
<221> NAME/KEY: misc_feature
<222> LOCATION: (393)..(396)
<223> OTHER INFORMATION: Xaa can be any amino acid
<220> FEATURE:
<221> NAME/KEY: misc_feature
<222> LOCATION: (400)..(403)
<223> OTHER INFORMATION: Xaa can be any amino acid
<220> FEATURE:
<221> NAME/KEY: misc_feature
<222> LOCATION: (405)..(407)
<223> OTHER INFORMATION: Xaa can be any amino acid
<220> FEATURE:
<221> NAME/KEY: misc_feature
<222> LOCATION: (409)..(414)
<223> OTHER INFORMATION: Xaa can be any amino acid
<220> FEATURE:
<221> NAME/KEY: misc_feature
<222> LOCATION: (416)..(416)
<223> OTHER INFORMATION: Xaa can be any amino acid
<220> FEATURE:
<221> NAME/KEY: misc_feature
<222> LOCATION: (418)..(419)
<223> OTHER INFORMATION: Xaa can be any amino acid
<220> FEATURE:
<221> NAME/KEY: misc_feature
<222> LOCATION: (422)..(428)
<223> OTHER INFORMATION: Xaa can be any amino acid
<220> FEATURE:
<221> NAME/KEY: misc_feature
<222> LOCATION: (431)..(431)
<223> OTHER INFORMATION: Xaa can be any amino acid
<220> FEATURE:
<221> NAME/KEY: misc_feature
<222> LOCATION: (433)..(436)
<223> OTHER INFORMATION: Xaa can be any amino acid
<220> FEATURE:
<221> NAME/KEY: misc_feature
<222> LOCATION: (438)..(438)
<223> OTHER INFORMATION: Xaa can be any amino acid
<220> FEATURE:
<221> NAME/KEY: misc_feature
<222> LOCATION: (440)..(441)
<223> OTHER INFORMATION: Xaa can be any amino acid
<220> FEATURE:
<221> NAME/KEY: misc_feature
<222> LOCATION: (443)..(446)
<223> OTHER INFORMATION: Xaa can be any amino acid
<220> FEATURE:
<221> NAME/KEY: misc_feature
<222> LOCATION: (448)..(455)
<223> OTHER INFORMATION: Xaa can be any amino acid
<220> FEATURE:
<221> NAME/KEY: misc_feature
<222> LOCATION: (457)..(459)
<223> OTHER INFORMATION: Xaa can be any amino acid
<220> FEATURE:
<221> NAME/KEY: misc_feature
<222> LOCATION: (461)..(461)
<223> OTHER INFORMATION: Xaa can be any amino acid
<220> FEATURE:
<221> NAME/KEY: misc_feature
<222> LOCATION: (463)..(479)
<223> OTHER INFORMATION: Xaa can be any amino acid
<220> FEATURE:
<221> NAME/KEY: misc_feature
<222> LOCATION: (481)..(481)
<223> OTHER INFORMATION: Xaa can be any amino acid
<220> FEATURE:
<221> NAME/KEY: misc_feature
```

```
<222> LOCATION: (484)..(488)
<223> OTHER INFORMATION: Xaa can be any amino acid
<220> FEATURE:
<221> NAME/KEY: misc_feature
<222> LOCATION: (490)..(490)
<223> OTHER INFORMATION: Xaa can be any amino acid
<220> FEATURE:
<221> NAME/KEY: misc_feature
<222> LOCATION: (492)..(493)
<223> OTHER INFORMATION: Xaa can be any amino acid
<220> FEATURE:
<221> NAME/KEY: misc_feature
<222> LOCATION: (495)..(496)
<223> OTHER INFORMATION: Xaa can be any amino acid
<220> FEATURE:
<221> NAME/KEY: misc_feature
<222> LOCATION: (498)..(513)
<223> OTHER INFORMATION: Xaa can be any amino acid
<220> FEATURE:
<221> NAME/KEY: misc_feature
<222> LOCATION: (516)..(516)
<223> OTHER INFORMATION: Xaa can be any amino acid
<220> FEATURE:
<221> NAME/KEY: misc_feature
<222> LOCATION: (518)..(519)
<223> OTHER INFORMATION: Xaa can be any amino acid
<220> FEATURE:
<221> NAME/KEY: misc_feature
<222> LOCATION: (522)..(522)
<223> OTHER INFORMATION: Xaa can be any amino acid
<220> FEATURE:
<221> NAME/KEY: misc_feature
<222> LOCATION: (526)..(537)
<223> OTHER INFORMATION: Xaa can be any amino acid
<220> FEATURE:
<221> NAME/KEY: misc_feature
<222> LOCATION: (542)..(543)
<223> OTHER INFORMATION: Xaa can be any amino acid
<220> FEATURE:
<221> NAME/KEY: misc_feature
<222> LOCATION: (548)..(548)
<223> OTHER INFORMATION: Xaa can be any amino acid
<220> FEATURE:
<221> NAME/KEY: misc_feature
<222> LOCATION: (551)..(551)
<223> OTHER INFORMATION: Xaa can be any amino acid
<220> FEATURE:
<221> NAME/KEY: misc_feature
<222> LOCATION: (554)..(554)
<223> OTHER INFORMATION: Xaa can be any amino acid
<220> FEATURE:
<221> NAME/KEY: misc_feature
<222> LOCATION: (557)..(562)
<223> OTHER INFORMATION: Xaa can be any amino acid
<220> FEATURE:
<221> NAME/KEY: misc_feature
<222> LOCATION: (564)..(564)
<223> OTHER INFORMATION: Xaa can be any amino acid
<220> FEATURE:
<221> NAME/KEY: misc_feature
<222> LOCATION: (566)..(570)
<223> OTHER INFORMATION: Xaa can be any amino acid
<220> FEATURE:
<221> NAME/KEY: misc_feature
<222> LOCATION: (572)..(575)
<223> OTHER INFORMATION: Xaa can be any amino acid
<220> FEATURE:
<221> NAME/KEY: misc_feature
<222> LOCATION: (594)..(595)
<223> OTHER INFORMATION: Xaa can be any amino acid
<220> FEATURE:
<221> NAME/KEY: misc_feature
<222> LOCATION: (597)..(599)
<223> OTHER INFORMATION: Xaa can be any amino acid
<220> FEATURE:
<221> NAME/KEY: misc_feature
<222> LOCATION: (602)..(602)
<223> OTHER INFORMATION: Xaa can be any amino acid
<220> FEATURE:
<221> NAME/KEY: misc_feature
```

-continued

```
<222> LOCATION: (604)..(604)
<223> OTHER INFORMATION: Xaa can be any amino acid
<220> FEATURE:
<221> NAME/KEY: misc_feature
<222> LOCATION: (607)..(608)
<223> OTHER INFORMATION: Xaa can be any amino acid
<220> FEATURE:
<221> NAME/KEY: misc_feature
<222> LOCATION: (613)..(613)
<223> OTHER INFORMATION: Xaa can be any amino acid
<220> FEATURE:
<221> NAME/KEY: misc_feature
<222> LOCATION: (617)..(620)
<223> OTHER INFORMATION: Xaa can be any amino acid
<220> FEATURE:
<221> NAME/KEY: misc_feature
<222> LOCATION: (622)..(626)
<223> OTHER INFORMATION: Xaa can be any amino acid
<220> FEATURE:
<221> NAME/KEY: misc_feature
<222> LOCATION: (628)..(630)
<223> OTHER INFORMATION: Xaa can be any amino acid
<220> FEATURE:
<221> NAME/KEY: misc_feature
<222> LOCATION: (632)..(638)
<223> OTHER INFORMATION: Xaa can be any amino acid
<220> FEATURE:
<221> NAME/KEY: misc_feature
<222> LOCATION: (642)..(642)
<223> OTHER INFORMATION: Xaa can be any amino acid
<220> FEATURE:
<221> NAME/KEY: misc_feature
<222> LOCATION: (644)..(644)
<223> OTHER INFORMATION: Xaa can be any amino acid
<220> FEATURE:
<221> NAME/KEY: misc_feature
<222> LOCATION: (648)..(648)
<223> OTHER INFORMATION: Xaa can be any amino acid
<220> FEATURE:
<221> NAME/KEY: misc_feature
<222> LOCATION: (651)..(652)
<223> OTHER INFORMATION: Xaa can be any amino acid
<220> FEATURE:
<221> NAME/KEY: misc_feature
<222> LOCATION: (654)..(654)
<223> OTHER INFORMATION: Xaa can be any amino acid
<220> FEATURE:
<221> NAME/KEY: misc_feature
<222> LOCATION: (658)..(659)
<223> OTHER INFORMATION: Xaa can be any amino acid
<220> FEATURE:
<221> NAME/KEY: misc_feature
<222> LOCATION: (662)..(664)
<223> OTHER INFORMATION: Xaa can be any amino acid
<220> FEATURE:
<221> NAME/KEY: misc_feature
<222> LOCATION: (666)..(666)
<223> OTHER INFORMATION: Xaa can be any amino acid
<220> FEATURE:
<221> NAME/KEY: misc_feature
<222> LOCATION: (668)..(668)
<223> OTHER INFORMATION: Xaa can be any amino acid
<220> FEATURE:
<221> NAME/KEY: misc_feature
<222> LOCATION: (672)..(681)
<223> OTHER INFORMATION: Xaa can be any amino acid
<220> FEATURE:
<221> NAME/KEY: misc_feature
<222> LOCATION: (683)..(708)
<223> OTHER INFORMATION: Xaa can be any amino acid
<220> FEATURE:
<221> NAME/KEY: misc_feature
<222> LOCATION: (710)..(714)
<223> OTHER INFORMATION: Xaa can be any amino acid
<220> FEATURE:
<221> NAME/KEY: misc_feature
<222> LOCATION: (716)..(717)
<223> OTHER INFORMATION: Xaa can be any amino acid
<220> FEATURE:
<221> NAME/KEY: misc_feature
```

```
<222> LOCATION: (719)..(721)
<223> OTHER INFORMATION: Xaa can be any amino acid
<220> FEATURE:
<221> NAME/KEY: misc_feature
<222> LOCATION: (724)..(724)
<223> OTHER INFORMATION: Xaa can be any amino acid
<220> FEATURE:
<221> NAME/KEY: misc_feature
<222> LOCATION: (726)..(728)
<223> OTHER INFORMATION: Xaa can be any amino acid
<220> FEATURE:
<221> NAME/KEY: misc_feature
<222> LOCATION: (730)..(737)
<223> OTHER INFORMATION: Xaa can be any amino acid
<220> FEATURE:
<221> NAME/KEY: misc_feature
<222> LOCATION: (740)..(740)
<223> OTHER INFORMATION: Xaa can be any amino acid
<220> FEATURE:
<221> NAME/KEY: misc_feature
<222> LOCATION: (743)..(747)
<223> OTHER INFORMATION: Xaa can be any amino acid
<220> FEATURE:
<221> NAME/KEY: misc_feature
<222> LOCATION: (751)..(752)
<223> OTHER INFORMATION: Xaa can be any amino acid
<220> FEATURE:
<221> NAME/KEY: misc_feature
<222> LOCATION: (754)..(754)
<223> OTHER INFORMATION: Xaa can be any amino acid
<220> FEATURE:
<221> NAME/KEY: misc_feature
<222> LOCATION: (756)..(759)
<223> OTHER INFORMATION: Xaa can be any amino acid
<220> FEATURE:
<221> NAME/KEY: misc_feature
<222> LOCATION: (761)..(762)
<223> OTHER INFORMATION: Xaa can be any amino acid
<220> FEATURE:
<221> NAME/KEY: misc_feature
<222> LOCATION: (764)..(773)
<223> OTHER INFORMATION: Xaa can be any amino acid
<220> FEATURE:
<221> NAME/KEY: misc_feature
<222> LOCATION: (775)..(794)
<223> OTHER INFORMATION: Xaa can be any amino acid
<220> FEATURE:
<221> NAME/KEY: misc_feature
<222> LOCATION: (796)..(800)
<223> OTHER INFORMATION: Xaa can be any amino acid
<220> FEATURE:
<221> NAME/KEY: misc_feature
<222> LOCATION: (802)..(804)
<223> OTHER INFORMATION: Xaa can be any amino acid
<220> FEATURE:
<221> NAME/KEY: misc_feature
<222> LOCATION: (806)..(812)
<223> OTHER INFORMATION: Xaa can be any amino acid
<220> FEATURE:
<221> NAME/KEY: misc_feature
<222> LOCATION: (814)..(814)
<223> OTHER INFORMATION: Xaa can be any amino acid
<220> FEATURE:
<221> NAME/KEY: misc_feature
<222> LOCATION: (816)..(821)
<223> OTHER INFORMATION: Xaa can be any amino acid

<400> SEQUENCE: 14

Leu Xaa Pro Arg Pro Xaa Ser Asp His Arg Xaa Xaa Xaa Ser Xaa Xaa
 1               5                  10                  15

Leu Xaa Xaa Val Xaa Xaa Xaa Xaa Xaa Xaa Xaa Xaa Xaa Xaa Xaa Xaa
                20                  25                  30

Xaa Xaa Xaa Xaa Xaa Xaa Xaa Tyr Xaa Tyr Xaa Xaa Xaa Xaa Xaa Gly
            35                  40                  45

Phe Ala Xaa Xaa Xaa Xaa Xaa Xaa Xaa Xaa Xaa Xaa Leu Xaa His Arg
 50                  55                  60
```

-continued

```
Xaa Xaa Val Xaa Xaa Xaa Xaa Xaa Asp Leu Xaa Val Xaa Xaa Xaa Xaa
65                  70                  75                  80

His Thr Thr Xaa Ser Pro Xaa Phe Xaa Gly Leu Xaa Xaa Xaa Xaa Xaa
                85                  90                  95

Xaa Xaa Xaa Xaa Xaa Xaa Xaa Xaa Xaa Gly Glu Gly Xaa Xaa Ile Gly
            100                 105                 110

Xaa Ile Asp Thr Gly Ile Xaa Pro Asn Xaa Pro Ser Phe Xaa Asp Xaa
        115                 120                 125

Gly Xaa Xaa Arg Xaa Xaa Xaa Xaa Pro Xaa Xaa Xaa Xaa Gly Xaa Cys
    130                 135                 140

Glu Xaa Xaa Xaa Xaa Xaa Xaa Xaa Xaa Xaa Cys Asn Lys Lys Leu Ile
145                 150                 155                 160

Gly Ala Xaa Xaa Phe Xaa Xaa Gly Xaa Xaa Ala Xaa Xaa Xaa Xaa Xaa
                165                 170                 175

Xaa Xaa Ile Xaa Xaa Xaa Xaa Xaa Xaa Xaa Xaa Xaa Xaa Ser Pro Xaa
            180                 185                 190

Asp Xaa Xaa Gly His Gly Thr His Val Ala Xaa Val Ala Ala Gly Asn
        195                 200                 205

His Xaa Xaa Xaa Xaa Xaa Xaa Xaa Xaa Xaa Xaa Xaa Gly Xaa Ala Ser
    210                 215                 220

Gly Ile Ala Pro Xaa Ala Xaa Ile Xaa Xaa Tyr Lys Ala Xaa Xaa Xaa
225                 230                 235                 240

Xaa Xaa Xaa Xaa Tyr Xaa Ser Asp Val Xaa Ala Ala Ile Asp Gln Ala
                245                 250                 255

Xaa Xaa Asp Gly Val Asp Val Leu Ser Leu Ser Ile Gly Xaa Xaa Xaa
            260                 265                 270

Xaa Xaa Asp Xaa Xaa Xaa Xaa Xaa Phe Xaa Xaa Xaa Asn Xaa Pro Ile
        275                 280                 285

Xaa Xaa Ala Xaa Xaa Xaa Ala Xaa Xaa Xaa Gly Ile Phe Val Val Xaa
    290                 295                 300

Ala Xaa Gly Asn Asp Gly Pro Xaa Tyr Xaa Thr Leu Xaa Asn Xaa Ala
305                 310                 315                 320

Pro Trp Ile Xaa Thr Val Gly Ala Gly Xaa Ile Asp Arg Xaa Xaa Xaa
                325                 330                 335

Xaa Xaa Leu Thr Xaa Gly Asn Xaa Val Thr Xaa Xaa Xaa Xaa Xaa Xaa
            340                 345                 350

Xaa Xaa Gly Xaa Xaa Xaa Xaa Xaa Val Xaa Xaa Xaa Xaa Xaa Xaa Ile
        355                 360                 365

Xaa Xaa Xaa Xaa Xaa Ser Thr Xaa Xaa Xaa Xaa Xaa Xaa Xaa Xaa Xaa
    370                 375                 380

Xaa Xaa Xaa Xaa Xaa Xaa Xaa Val Xaa Xaa Xaa Xaa Val Ala Gly Xaa
385                 390                 395                 400

Xaa Xaa Xaa Cys Xaa Xaa Xaa Ile Xaa Xaa Xaa Xaa Xaa Xaa Ser Xaa
                405                 410                 415

Ile Xaa Xaa Ala Leu Xaa Xaa Xaa Xaa Xaa Xaa Xaa Ala Ala Xaa Val
            420                 425                 430

Xaa Xaa Xaa Xaa Asp Xaa Tyr Xaa Xaa Gly Xaa Xaa Xaa Xaa Glu Xaa
        435                 440                 445

Xaa Xaa Xaa Xaa Xaa Xaa Xaa Pro Xaa Xaa Xaa Ile Xaa Ser Xaa Xaa
    450                 455                 460

Xaa Xaa Xaa Xaa Xaa Xaa Xaa Xaa Xaa Xaa Xaa Xaa Xaa Xaa Xaa Tyr
465                 470                 475                 480

Xaa Ser Ser Xaa Xaa Xaa Xaa Xaa Thr Xaa Lys Xaa Xaa Phe Xaa Xaa
```

```
                    485                 490                 495
Thr Xaa Xaa Xaa Xaa Xaa Xaa Xaa Xaa Xaa Xaa Xaa Xaa Xaa
                500                 505                 510

Xaa Ala Pro Xaa Val Xaa Xaa Tyr Ser Xaa Arg Gly Pro Xaa Xaa Xaa
            515                 520                 525

Xaa Xaa Xaa Xaa Xaa Xaa Xaa Xaa Leu Lys Pro Asp Xaa Xaa Ala
        530                 535                 540

Pro Gly Thr Xaa Ile Leu Xaa Ala Trp Xaa Ser Val Xaa Xaa Xaa
545                 550                 555                 560

Xaa Xaa Phe Xaa Gly Xaa Xaa Xaa Xaa Xaa Phe Xaa Xaa Xaa Xaa Gly
            565                 570                 575

Thr Ser Met Ala Ala Pro His Val Ala Gly Val Ala Ala Leu Ile Lys
            580                 585                 590

Gln Xaa Xaa Pro Xaa Xaa Xaa Pro Ser Xaa Ile Xaa Ser Ala Xaa Xaa
        595                 600                 605

Thr Thr Ala Leu Xaa Leu Asp Asn Xaa Xaa Xaa Xaa Ile Xaa Xaa Xaa
            610                 615                 620

Xaa Xaa Tyr Xaa Xaa Xaa Asp Xaa Xaa Xaa Xaa Xaa Xaa Xaa Pro Leu
625                 630                 635                 640

Asp Xaa Gly Xaa Gly His Val Xaa Thr Asn Xaa Xaa Leu Xaa Pro Gly
            645                 650                 655

Leu Xaa Xaa Asp Thr Xaa Xaa Asp Xaa Ile Xaa Phe Leu Cys Xaa
        660                 665                 670

Xaa Xaa Xaa Xaa Xaa Xaa Xaa Xaa Asn Xaa Xaa Xaa Xaa Xaa Xaa
            675                 680                 685

Xaa Xaa Xaa Xaa Xaa Xaa Xaa Xaa Xaa Xaa Xaa Xaa Xaa Xaa Xaa
            690                 695                 700

Xaa Xaa Xaa Xaa Leu Xaa Xaa Xaa Xaa Ser Xaa Xaa Ser Xaa Xaa
705                 710                 715                 720

Xaa Thr Phe Xaa Arg Xaa Xaa Xaa Asn Xaa Xaa Xaa Xaa Xaa Xaa
            725                 730                 735

Xaa Ser Tyr Xaa Val Gly Xaa Xaa Xaa Xaa Gly Leu Asn Xaa Xaa
            740                 745                 750

Val Xaa Pro Xaa Xaa Xaa Xaa Phe Xaa Xaa Lys Xaa Xaa Xaa Xaa Xaa
        755                 760                 765

Xaa Xaa Xaa Xaa Xaa Glu Xaa Xaa Xaa Xaa Xaa Xaa Xaa Xaa Xaa
        770                 775                 780

Xaa Xaa Xaa Xaa Xaa Xaa Xaa Xaa Gly Xaa Xaa Xaa Xaa Xaa
785                 790                 795                 800

Asp Xaa Xaa Xaa Ala Xaa Xaa Xaa Xaa Xaa Xaa Val Xaa Ala Xaa
            805                 810                 815

Xaa Xaa Xaa Xaa Xaa Ser
            820

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 15
cggcacgagg ctctggtggt                                               20

<210> SEQ ID NO 16
<211> LENGTH: 20
```

```
<212> TYPE: DNA
<213> ORGANISM: Artificial Sequence
<220> FEATURE:
<223> OTHER INFORMATION: Description of Artificial Sequence: primer

<400> SEQUENCE: 16 cctttccac aaaggggaga                                            20
```